(12) United States Patent  
Piotrowski et al.

(10) Patent No.: US 7,485,641 B2
(45) Date of Patent: Feb. 3, 2009

(54) SUBSTITUTED 3-AMINO-PYRROLIDINO-4-LACTAMS

(75) Inventors: David W. Piotrowski, Waterford, CT (US); Yu Hui, Groton, CT (US); John W. Benbow, Norwich, CT (US)

(73) Assignee: Pfizer, Inc., New York, NY (US)

( * ) Notice: Subject to any disclaimer, the term of this patent is extended or adjusted under 35 U.S.C. 154(b) by 51 days.

(21) Appl. No.: 11/764,445

(22) Filed: Jun. 18, 2007

(65) Prior Publication Data

US 2007/0299076 A1 Dec. 27, 2007

Related U.S. Application Data

(60) Provisional application No. 60/805,371, filed on Jun. 21, 2006, provisional application No. 60/871,482, filed on Dec. 22, 2006.

(51) Int. Cl.
*C07D 401/14* (2006.01)
*C07D 403/14* (2006.01)
*C07D 405/14* (2006.01)
*C07D 407/14* (2006.01)
*C07D 409/14* (2006.01)
*A61K 31/4025* (2006.01)
*A61K 31/404* (2006.01)
*A61K 31/445* (2006.01)
*A61K 31/506* (2006.01)
*A61K 31/53* (2006.01)
*A61P 3/10* (2006.01)

(52) U.S. Cl. ............... 514/245; 514/248; 514/256; 514/266.2; 514/335; 514/415; 514/424; 514/426; 544/209; 544/237; 544/283; 544/326; 546/208; 548/469; 548/518

(58) Field of Classification Search ............... 514/245, 514/248, 256, 266.2, 335, 415, 424, 426; 544/209, 237, 283, 326; 546/208; 548/469, 548/518
See application file for complete search history.

(56) References Cited

U.S. PATENT DOCUMENTS

| 6,849,622 B2 | 2/2005 | Yasuda et al. ......... 514/217.08 |
| 7,138,397 B2 | 11/2006 | Yasuda et al. ......... 514/254.01 |
| 7,160,877 B2 | 1/2007 | Yasuda et al. ......... 514/217.08 |
| 2004/0259903 A1 | 12/2004 | Boehringer et al. ......... 514/290 |
| 2006/0135512 A1 | 6/2006 | Boehringer et al. ....... 514/222.2 |
| 2006/0241146 A1 | 10/2006 | Yasuda et al. ............. 514/326 |
| 2006/0264433 A1 | 11/2006 | Backes et al. ............ 514/235.2 |
| 2007/0037785 A1 | 2/2007 | Ansorge et al. ............. 514/183 |

FOREIGN PATENT DOCUMENTS

| WO | WO03080633 | 10/2003 |
| WO | WO2005116029 | 12/2005 |
| WO | WO2006097175 | 9/2006 |
| WO | WO2006104356 | 10/2006 |
| WO | WO2007024993 | 3/2007 |

OTHER PUBLICATIONS

Liang et al., 30th National Medicinal Chemistry Symposium, Jun. 28, 2006, "Design of Novel DPP-4 Inhibitors Using Structural Biology and Molecular Modeling", #126.

*Primary Examiner*—Venkataraman Balasubramanian
(74) *Attorney, Agent, or Firm*—Gregg C. Benson; Arlene K. Musser

(57) ABSTRACT

The invention provides compounds of formula (1),

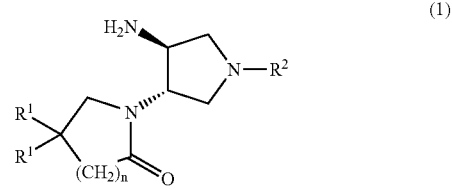

and the pharmaceutically acceptable salt thereof, wherein $R^1$, n and $R^2$ are as described herein; compositions thereof; and uses thereof.

19 Claims, No Drawings

SUBSTITUTED 3-AMINO-PYRROLIDINO-4-LACTAMS

FIELD OF THE INVENTION

The invention relates to substituted 3-amino-pyrrolidine-4-lactam derivatives, pharmaceutical formulations thereof, and uses thereof.

BACKGROUND OF THE INVENTION

DPP-IV (EC 3.4.14.5) is a serine protease that preferentially hydrolyzes an N-terminal dipeptide from proteins having proline or alanine in the 2-position. DPP-IV is believed to be involved in diabetes, glucose tolerance, obesity, appetite regulation, lipidemia, osteoporosis, neuropeptide metabolism and T-cell activation, among others. Accordingly, administration of DPP-IV inhibitors in vivo prevents N-terminal degradation of substrate peptides, thereby resulting in higher circulating concentrations of such peptides, and therapeutic benefits associated with such elevated concentrations.

DPP-IV has been implicated in the control of glucose homeostasis because its substrates include the incretin peptides glucagon-like peptide 1 (GLP-1) and gastric inhibitory polypeptide (GIP). Cleavage of the N-terminal amino acids from these peptides renders them functionally inactive. GLP-1 has been shown to be an effective anti-diabetic therapy in Type 2 diabetic patients and to reduce the meal-related insulin requirement in Type 1 diabetic patients. GLP-1 and/or GIP are believed to regulate satiety, lipidemia and osteogenesis. Exogenous GLP-1 has been proposed as a treatment for patients suffering from acute coronary syndrome, angina and ischemic heart disease.

Administration of DPP-IV inhibitors in vivo prevents N-terminal degradation of GLP-1 and GIP, resulting in higher circulating concentrations of these peptides, increased insulin secretion and improved glucose tolerance. On the basis of these observations, DPP-IV inhibitors are regarded as agents for the treatment of Type 2 diabetes, a disease in which glucose tolerance is impaired. In addition, treatment with DPP-IV inhibitors prevents degradation of Neuropeptide Y (NPY), a peptide associated with a variety of central nervous system disorders, and Peptide YY which has been linked to gastrointestinal conditions such as ulcers, irritable bowel disease, and inflammatory bowel disease.

In spite of the early discovery of insulin and its subsequent widespread use in the treatment of diabetes, and the later discovery of and use of sulfonylureas (e.g. chlorpropamide, tolbutamide, acetohexamide), biguanides (e.g., phenformin), metformin, and thiazolidinediones (e.g., rosiglitazone, pioglitazone) as oral hypoglycemic agents, the treatment of diabetes remains less than satisfactory.

The use of insulin, necessary in Type 1 diabetic patients and about 10% of Type 2 diabetic patients in whom currently available oral hypoglycemic agents are ineffective, requires multiple daily doses, usually by self-injection. Determination of the appropriate dosage of insulin necessitates frequent estimations of the glucose concentration in urine or blood. The administration of an excess dose of insulin causes hypoglycemia, with consequences ranging from mild abnormalities in blood glucose to coma, or even death.

Treatment of Type 2 diabetes usually comprises a combination of diet, exercise, oral agents, and in more severe cases, insulin. However, the clinically available hypoglycemics can have side effects that limit their use.

Further, poorly controlled hyperglycemia is a direct cause of the multiplicity of complications (cataracts, neuropathy, nephropathy, retinopathy, and cardiomyopathy) that characterize advanced Type 2 diabetes.

Therefore, there is a continuing need for new oral hypoglycemic agents which control blood glucose levels in patients in need thereof.

SUMMARY OF THE INVENTION

The present invention relates to compounds having the structure of formula (1)

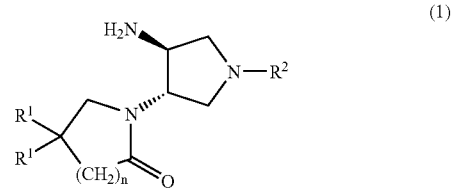

or a pharmaceutically acceptable salt thereof, wherein each $R^1$ is independently selected from H or F and n is 1 or 2.

$R^2$ is either

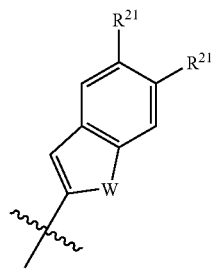

wherein W is O, N or S and $R^{21}$ is halo, —$(C_1-C_6)$alkyl, or —$(C_1-C_6)$alkoxy, or $R^2$ is a heteroaryl, wherein said heteroaryl is optionally substituted with one $R^3$ and optionally substituted with one to two $R^4$.

$R^3$ is heterocycloalkyl, heteroaryl, benzyl-O—, phenyl, phenyl-O—, phenyl-S— or phenyl-S(O)$_2$O—. $R^3$ is optionally, independently substituted independently with one to four hydroxy, cyano, halo, nitro, —$(C_1-C_6)$alkyl, —$(C_1-C_6)$haloalkyl, —$(C_1-C_6)$haloalkoxy, —$(C_1-C_6)$alkoxy, —NH(CO)$(C_1-C_6)$alkyl, —S(O)$_T$$(C_1-C_6)$alkyl, —S(O)$_2$—NR$^5$R$^6$, —NH(CO)$(C_1-C_6)$haloalkyl, oxo or $R^7$-E-.

$R^7$ is phenyl or pyridinyl and E is —O— or a covalent bond and $R^7$ is optionally, independently substituted with —$(C_1-C_3)$alkyl, halo, cyano, OH or methoxy.

T is 0 or 2.

Each $R^4$ is independently cyano, halo, nitro, —$(C_1-C_6)$alkyl, —$(C_1-C_6)$alkyl-OH, —$(C_1-C_6)$haloalkyl, —$(C_3-C_6)$cycloalkyl, —$(C_1-C_6)$alkyl-CN, —OR$^5$, —SR$^5$, —OS(O)$_2$R$^5$ or —NR$^5$R$^6$.

$R^5$ and $R^6$ are each independently hydrogen, —$(C_1-C_6)$alkyl, —$(C_1-C_6)$haloalkyl, or —$(C_3-C_6)$cycloalkyl.

The present invention also relates to a pharmaceutical composition comprising a compound of the present invention, or a pharmaceutically acceptable salt of the compound, or a solvate of the compound or salt, and a pharmaceutically acceptable carrier, vehicle, diluent or excipient.

The present invention further relates to a method of treating diabetes, such as Type 1 or Type 2 diabetes, comprising administering to a mammal in need of such treatment a therapeutically effective amount of a compound of the present invention, or a pharmaceutically acceptable salt of the compound, or a solvate of the compound or salt. Preferably, the type of diabetes treated is Type 2 diabetes.

The present invention additionally relates to a method of inhibiting dipeptidyl peptidase-IV in a mammal comprising administering to said mammal an inhibitory amount of a compound of the present invention, or a pharmaceutically acceptable salt of said compound, or a solvate of said compound or salt.

The compounds, salts, solvates and pharmaceutical compositions of the present invention are useful for the treatment of Type 2 diabetes, Type 1 diabetes, impaired glucose tolerance, hyperglycemia, metabolic syndrome (also known as Syndrome X or insulin resistance syndrome), and diabetic complications such as sugar cataracts, diabetic neuropathy, diabetic nephropathy, diabetic retinopathy and diabetic cardiomyopathy; and also the prevention or mitigation of disease progression in Type 1 and Type 2 diabetes.

The compounds, salts, solvates and pharmaceutical compositions of the present invention are also useful for the treatment of diabetes-related atherosclerosis; obesity, conditions exacerbated by obesity, hypertension, hyperlipidemia, osteoporosis, osteopenia, frailty, bone loss, bone fracture, acute coronary syndrome, infertility due to polycystic ovary syndrome, short stature due to growth hormone deficiency, anxiety, depression, insomnia, chronic fatigue, epilepsy, eating disorders, chronic pain, alcohol addiction, diseases associated with intestinal motility, ulcers, irritable bowel syndrome, inflammatory bowel syndrome, short bowel syndrome, and cancer.

DETAILED DESCRIPTION OF THE INVENTION

The terms used to describe the present invention have the following meanings herein.

The compounds and intermediates of the present invention may be named according to either the IUPAC (International Union for Pure and Applied Chemistry) or CAS (Chemical Abstracts Service) nomenclature systems.

The carbon atom content of the various hydrocarbon-containing moieties herein may be indicated by a prefix designating the minimum and maximum number of carbon atoms in the moiety, for example, the prefixes $(C_a-C_b)$alkyl, and $C_{a-b}$alkyl, indicate an alkyl moiety of the integer "a" to "b" carbon atoms, inclusive. Thus, for example, $(C_1-C_6)$alkyl and $C_{1-6}$alkyl refer to an alkyl group of one to six carbon atoms inclusive.

The symbol "—" represents a covalent bond.

The term "alkyl" denotes a straight or branched chain of carbon atoms, wherein the alkyl group optionally incorporates one or more double or triple bonds, or a combination of double bonds and triple bonds. Examples of alkyl groups include methyl, ethyl, propyl, isopropyl, thinly, and the like.

The term "alkoxy" refers to straight or branched, monovalent, saturated aliphatic chains of carbon atoms bonded to an oxygen atom that is attached to a core structure. Examples of alkoxy groups include methoxy, ethoxy and iso-propoxy.

The term "cycloalkyl" denotes a saturated monocyclic or bicyclic cycloalkyl group. Cycloalkyl groups may be optionally fused to aromatic hydrocarbons such as benzene to form fused cycloalkyl groups, such as indanyl and the like. Examples of cycloalkyl groups include cyclopropyl, cyclobutyl and cyclopentyl.

The term "heterocycloalkyl" refers to a three to eight-membered non-aromatic heterocyclic ring system, optionally fused to a five- or six-membered aromatic or heteroaromatic ring system, wherein at least one carbon atom is replaced with a heteroatom selected from oxygen, nitrogen, —NH—, or —S(O)$_m$— wherein m is zero, 1, or 2, optionally containing from one to three double bonds, and wherein the ring attachment can occur at either a ring carbon or ring nitrogen atom. Examples of heterocycloalkyl groups include, but are not limited to, azetidyl, dihydro-imidazo[4,5-c]pyridyl, dihydroisoquinolyl, dihydroisoindolyl, dihydro-isoxazolo[4,3-c]pyridyl, dihydro-pyrazolo[4,3-c]pyridyl, dihydro-pyrido[4,3-a]pyrimidyl, dihydro-pyrido[4,3-d]pyrimidyl, dihydro-pyrido[3,4-d]pyrimidyl, dihydro-4-thiazolo[5,4-c]pyridyl, dihydro-thieno[3,2-c]pyridyl, dihydrotriazolo[1,2,4][4,3-a]pyrazinyl, homopiperazinyl, morpholinyl, piperazinyl, piperidinyl, pyrrolidinyl, tetrahydrobenzo[d]azepinyl, tetrahydro-imidazo[4,5-c]pyridyl, tetrahydroisoquinolyl, tetrahydropyrazolo[4,3-c]pyridyl, tetrahydropyrido[3,4-d]pyrimidyl, tetrahydropyrido[4,3-d]pyrimidyl, thiomorpholinyl, and the like.

The term "heteroaryl" means a radical of a monocyclic aromatic ring containing five or six ring atoms consisting of carbon and 1 to 4 heteroatoms each selected from the group consisting of non-peroxide O, S, N, with appropriate bonding to satisfy valence requirements, wherein the attachment may be via a ring carbon or ring nitrogen where a nitrogen is present. The term "heteroaryl" also includes a radical of a fused bicyclic heteroaromatic ring having eight to ten ring atoms consisting of carbon and 1 to 6 heteroatoms each selected from non-peroxide O, S, N, with appropriate bonding to satisfy valence requirements, wherein the attachment may be via a ring carbon or ring nitrogen where a nitrogen is present. Examples of heteroaryl groups include, but are not limited to, benzimidazolyl, benzoisothiazolyl, benzisoxazolyl, benzoxazolyl, benzothiazolyl, benzofuranyl, benzofurazanyl, benzothiazolyl, benzothienyl, benzothiophenyl, cinnolinyl, furanyl, furazanyl furopyridyl, furopyridinyl, imidazolopyrimidyl, imidazolyl, indolizinyl, indazolyl, indolyl, isoindolyl, isoquinolyl, isothiazolyl, isoxadiazolyl, isoxazolyl, naphthridinyl, oxazolopyridyl, oxadiazolyl, oxazolyl, phthalazinyl, pteridinyl, purinyl, pyrazinyl, pyridazinyl, pyrrolopyrimidyl, pyrrolopyridyl, pyrazolopyrimidyl, pyrazolyl, pyridyl, pyrimidinyl, pyrrolyl, quinazolinyl, quinazolyl, quinolyl, quinoxalinyl, tetrazolyl, thiazolyl, thiadiazolyl, thiazolopyridyl, thienopyridyl, thienyl, triazinyl, triazolyl, 1,1-dioxo-1H-1,2-benzoisothiazolyl, oxazolopyridyl, and the like.

The term "halo" means chloro, bromo, fluoro, or iodo. Preferably, the halo is a fluoro group.

The term "haloalkyl" is defined herein as an alkyl group substituted with one or more halo substituents, independently selected from fluoro, chloro, bromo, and iodo. Examples of haloalkyl groups include, but are not limited to, trifluoromethyl, trichloromethyl, and the like.

The term "haloalkoxy" is defined herein as an alkoxy group substituted with one or more halo substituents, independently selected from fluoro, chloro, bromo, and iodo.

The term "substituted" means that a hydrogen atom on a molecule has been replaced with a different atom or molecule. The atom or molecule replacing the hydrogen atom is denoted as a "substituent."

The term "radical" denotes a group of atoms that behaves as a single reactant in a chemical reaction, e.g., an organic radical is a group of atoms that imparts characteristic properties to a compound containing it, or which remains unchanged during a series of reactions, or transformations.

The terms "treating", "treated", or "treatment" as employed herein includes preventing (e.g., prophylaxis), palliating, slowing progression and curing a disease, such as Type I or II diabetes, or a disease-related condition such as a diabetic complication.

The phrase "therapeutically effective amount" means an amount of a compound of the present invention that (i) treats or prevents the particular disease, condition, or disorder, (ii) attenuates, ameliorates, or eliminates one or more symptoms of the particular disease, condition, or disorder, or (iii) prevents or delays the onset of one or more symptoms of the particular disease, condition, or disorder described herein. The phrase "pharmaceutically acceptable" indicates that the designated carrier, vehicle, diluent, excipient(s), and/or salt is generally chemically and/or physically compatible with the other ingredients comprising the formulation, and physiologically compatible with the recipient thereof.

The term "mammal" relates to an individual animal that is a member of the taxonomic class Mammalia. Examples of mammals include, but are not limited to, humans, dogs, cats, horses and cattle. In the present invention, the preferred mammals are humans, dogs and cats. More preferably, the mammal is a human.

The phrase "inert solvent" refers to a solvent, or mixture of solvents, that does not interact with starting materials, reagents, intermediates, or products in a manner that adversely affects their desired properties.

The term "related salts" as used herein means pharmaceutically acceptable salts of compounds of the present invention.

In the present invention, it is preferred, for the compounds of formula (1), and for related salts, that n is 2.

It is more preferred for the compounds of formula (1), and for related salts, that n is 2 and that $R^2$ is pyrimidinyl, quinazolinyl, triazinyl or phthalazinyl which is optionally substituted with one $R^3$ and optionally substituted with one to two $R^4$.

It is even more preferred for the compounds of formula (1), and for related salts, that n is 2 and that $R^2$ is pyrimidinyl, quinazolinyl, triazinyl or phthalazinyl which is optionally substituted with one to two $R^4$ and also optionally substituted with one $R^3$ wherein $R^3$ is pyrrolidinyl, piperidinyl, pyridinyl, phenyl, dihdyroisoindolinyl, dihydroisoquinolinyl, 6,7-dihydroisoxazolo[4,3-c]pyridin-5(4H)-yl, benzyl-O—, phenyl, phenyl-O—, phenyl-S— or phenyl-S(O)$_2$O—, wherein $R^3$ is optionally substituted with one to four halo, —S(O)$_7$(C$_1$-C$_6$)alkyl, —S(O)$_2$—NR$^5$R$^6$ or R$^7$-E-.

In yet an even more preferred embodiment of the compounds of the present invention, includes compounds having the structure of formula (2)

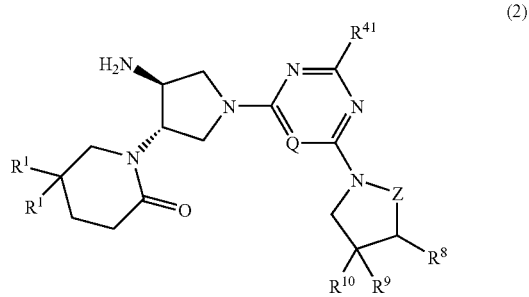

(2)

or a pharmaceutically acceptable salt thereof. In formula (2), $R^1$ is H or F; Q is —N—, —CH— or —CF—; $R^{41}$ is H or —(C$_1$-C$_3$)alkyl, —(C$_1$-C$_3$)haloalkyl, —S—(C$_1$-C$_3$)alkyl or cyclopropyl; Z is —CH$_2$— or —(CH$_2$)$_2$—; and $R^8$, $R^9$ and $R^{10}$ are each independently H or F.

It is preferred for compounds of formula (2), and for related salts, that Z is —CH$_2$—.

It is more preferred for compounds of formula (2), and for related salts, that Z is —CH$_2$— and $R^9$ and $R^{10}$ are each F, more preferably with $R^{41}$ being H.

It is even more preferred for compounds of formula (2), and for related salts, that Z is —CH$_2$—, $R^9$ and $R^{10}$ are each F, $R^{41}$ is H and each $R^1$ is F.

It is yet even more preferred for compounds of formula (2), and for related salts, that Z is —CH$_2$—, $R^9$ and $R^{10}$ are each F, $R^{41}$ is H, each $R^1$ is F and Q is —N—.

A most preferred compound of the present invention is 1-((3S,4S)-4-amino-1-(4-(3,3-difluoropyrrolidin-1-yl)-1,3, 5-triazin-2-yl)pyrrolidin-3-yl)-5,5-difluoropiperidin-2-one.

Alternately, it is preferred for compounds of formula (2), and for related salts, that Z is —CH$_2$—, $R^9$ and $R^{10}$ are each F, $R^{41}$ is H, each $R^1$ is F and Q is —CH—.

The compounds of the present invention all contain at least two stereogenic centers, specifically the (3S,4S)-pyrrolidin-3-yl stereogenic centers shown in formula (2).

The compounds of the present invention may be resolved into the pure enantiomers by methods known to those skilled in the art, for example by formation of diastereoisomeric salts which may be separated, for example, by crystallization; formation of diastereoisomeric derivatives or complexes which may be separated, for example, by crystallization, gas-liquid or liquid chromatography; selective reaction of one enantiomer with an enantiomer-specific reagent, for example enzymatic esterification; or gas-liquid or liquid chromatography in a chiral environment, for example on a chiral support for example silica with a bound chiral ligand or in the presence of a chiral solvent. It will be appreciated that where the desired stereoisomer is converted into another chemical entity by one of the separation procedures described above, a further step is required to liberate the desired enantiomeric form. Alternatively, the specific stereoisomers may be synthesized by using an optically active starting material, by asymmetric synthesis using optically active reagents, substrates, catalysts or solvents, or by converting one stereoisomer into the other by asymmetric transformation.

Wherein said compounds contain one or more additional stereogenic centers, those skilled in the art will appreciate that all diastereoisomers and diastereoisomeric mixtures of the compounds illustrated and discussed herein are within the scope of the present invention. These diastereoisomers may be isolated by methods known to those skilled in the art, for example, by crystallization, gas-liquid or liquid chromatography. Alternatively, intermediates in the course of the synthesis may exist as racemic mixtures and be subjected to resolution by methods known to those skilled in the art, for example by formation of diastereoisomeric salts which may be separated, for example, by crystallization; formation of diastereoisomeric derivatives or complexes which may be separated, for example, by crystallization, gas-liquid or liquid chromatography; selective reaction of one enantiomer with an enantiomer-specific reagent, for example enzymatic esterification; or gas-liquid or liquid chromatography in a chiral environment, for example on a chiral support for example silica with a bound chiral ligand or in the presence of a chiral solvent. It will be appreciated that where the desired stereoisomer is converted into another chemical entity by one of the separation procedures described above, a further step is required to liberate the desired enantiomeric form. Alternatively, specific stereoisomers may be synthesized by asymmetric synthesis using optically active reagents, substrates, catalysts or solvents, or by converting one stereoisomer into the other by asymmetric transformation.

Certain compounds of formula (2) may exist in different stable conformational forms which may be separable. Torsional asymmetry due to restricted rotation about an asymmetric single bond, for example because of steric hindrance or ring strain, may permit separation of different conformers. The compounds of the present invention further include each conformational isomer of compounds of formula (1) and mixtures thereof.

The compounds of the present invention, and the salts thereof, may exist in unsolvated as well as solvated forms with pharmaceutically acceptable solvents such as water, ethanol, and the like.

Certain compounds of formula (1) and their salts and solvates may exist in more than one crystal form. Polymorphs of compounds represented by formula (1) form part of this invention and may be prepared by crystallization of a compound of formula (1) under different conditions. For example, using different solvents or different solvent mixtures for recrystallization; crystallization at different temperatures; various modes of cooling, ranging from very fast to very slow cooling during crystallization. Polymorphs may also be obtained by heating or melting a compound of formula (1) followed by gradual or fast cooling. The presence of polymorphs may be determined by solid probe NMR spectroscopy, IR spectroscopy, differential scanning calorimetry, powder X-ray diffraction or such other techniques.

This invention also includes isotopically-labeled compounds, which are identical to those described by formula (2), but for the fact that one or more atoms are replaced by an atom having an atomic mass or mass number different from the atomic mass or mass number usually found in nature. Examples of isotopes that can be incorporated into compounds of the invention include isotopes of hydrogen, carbon, nitrogen, oxygen, sulfur and fluorine, such as $^{2}H$, $^{3}H$, $^{3}C$, $^{14}C$, $^{15}N$, $^{18}O$, $^{17}O$, $^{35}S$, $^{36}Cl$, $^{125}I$, $^{129}I$, and $^{18}F$ respectively. Compounds of the present invention, and pharmaceutically acceptable salts of the compounds which contain the aforementioned isotopes and/or other isotopes of other atoms are within the scope of this invention. Certain isotopically-labeled compounds of the present invention, for example those into which radioactive isotopes such as $^{3}H$ and $^{14}C$ are incorporated, are useful in drug and/or substrate tissue distribution assays. Tritiated (i.e., $^{3}H$), and carbon-14 (i.e., $^{14}C$), isotopes are particularly preferred for their ease of preparation and delectability. Further, substitution with heavier isotopes such as deuterium (i.e., $^{2}H$), can afford certain therapeutic advantages resulting from greater metabolic stability, for example increased in vivo half-life or reduced dosage requirements and, hence, may be preferred in some circumstances. Isotopically labeled compounds of formula (2) of this invention, salts and solvates thereof can generally be prepared by carrying out the procedures disclosed in the schemes and/or in the Examples below, by substituting a readily available isotopically labeled reagent for a non-isotopically labeled reagent.

Pharmaceutically acceptable salts, as used herein in relation to compounds of the present invention, include pharmaceutically acceptable inorganic and organic salts of said compound. These salts can be prepared in situ during the final isolation and purification of a compound, or by separately reacting the compound or prodrug thereof, with a suitable organic or inorganic acid and isolating the salt thus formed. Representative salts include, but are not limited to, the hydrobromide, hydrochloride, hydroiodide, sulfate, bisulfate, nitrate, acetate, trifluoroacetate, oxalate, besylate, camsylate, palmitate, pamoate, malonate, stearate, laurate, malate, borate, benzoate, lactate, phosphate, hexafluorophosphate, benzene sulfonate, tosylate, formate, citrate, maleate, fumarate, succinate, tartrate, naphthylate, mesylate, glucoheptonate, lactobionate and laurylsulphonate salts, and the like. These may also include cations based on the alkali and alkaline earth metals, such as sodium, lithium, potassium, calcium, magnesium, and the like, as well as non-toxic ammonium, quaternary ammonium, and amine cations including, but not limited to, ammonium, tetramethylammonium, tetraethylammonium, methylamine, dimethylamine, trimethylamine, triethylamine, ethylamine, and the like. For additional examples see, for example, Berge, et al., J. Pharm. Sci., 66, 1-19 (1977).

The compounds of the present invention may be isolated and used per se or in the form of their pharmaceutically acceptable salts or solvates. In accordance with the present invention, compounds with multiple basic nitrogen atoms can form salts with varying number of equivalents ("eq.") of acid. It will be understood by practitioners that all such salts are within the scope of the present invention.

The present invention further includes prodrugs of compounds of formula (1). A prodrug of a compound of formula (1) may be one formed in a conventional manner with a functional group of the compound, such as with an amino, hydroxy or carboxy group. The term "prodrug" means a compound that is transformed in vivo to yield a compound of formula (1) or a pharmaceutically acceptable salt or solvate of the compound. The transformation may occur by various mechanisms, such as through hydrolysis in blood. A discussion of the use of prodrugs is provided by T. Higuchi and W. Stella, "Pro-drugs as Novel Delivery Systems," Vol. 14 of the A.C.S. Symposium Series, and in Bioreversible Carriers in Drug Design, ed. Edward B. Roche, American Pharmaceutical Association and Pergamon Press, 1987.

For example, as all of the compounds of the present invention incorporate an amine functional group, a prodrug can be formed by the replacement of a hydrogen atom in the amine group with a group such as R-carbonyl, RO-carbonyl, NRR'-carbonyl where R and R' are each independently $(C_1-C_{10})$ alkyl, $(C_3-C_7)$cycloalkyl, benzyl, or R-carbonyl is a natural α-aminoacyl or natural α-aminoacyl-natural α-aminoacyl, —C(OH)C(O)OY' wherein Y' is H, $(C_1-C_6)$alkyl or benzyl, —C(OY$_0$)Y$_1$ wherein Y$_0$ is $(C_1-C_4)$ alkyl and Y$_1$ is $(C_1-C_6)$ alkyl, carboxy$(C_1-C_6)$alkyl, amino$(C_1-C_4)$alkyl or mono-N— or di-N,N—$(C_1-C_6)$alkylaminoalkyl, —C(Y$_2$)Y$_3$ wherein Y$_2$ is H or methyl and Y$_3$ is mono-N— or di-N,N—$(C_1-C_6)$alkylamino, morpholino, piperidin-1-yl or pyrrolidin-1-yl.

Similarly, if a compound of the present invention contains an alcohol functional group, a prodrug can be formed by the replacement of the hydrogen atom of the alcohol group with a group such as $(C_1-C_6)$alkanoyloxymethyl, 1-$((C_1-C_6)$alkanoyloxy)ethyl, 1-methyl-1-$((C_1-C_6)$alkanoyloxy)ethyl, $(C_1-C_6)$alkoxycarbonyloxymethyl, N—$(C_1-C_6)$alkoxycarbonylaminomethyl, succinoyl, $(C_1-C_6)$alkanoyl, α-amino$(C_1-C_4)$alkanoyl, arylacyl and α-aminoacyl, or α-aminoacyl-α-aminoacyl, where each α-aminoacyl group is independently selected from the naturally occurring L-amino acids, $P(O)(OH)_2$, —$P(O)(O(C_1-C_6)$alkyl$)_2$ or glycosyl (the radical resulting from the removal of a hydroxyl group of the hemiacetal form of a carbohydrate).

If a compound of the present invention contains a carboxylic acid functional group, a prodrug can comprise an ester formed by the replacement of the hydrogen atom of the acid group with a group such as $(C_1-C_8)$alkyl, $(C_2-C_{12})$alkanoyloxymethyl, 1-(alkanoyloxy)ethyl having from 4 to 9 carbon atoms, 1-methyl-1-(alkanoyloxy)-ethyl having from 5 to 10 carbon atoms, alkoxycarbonyloxymethyl having from 3 to 6 carbon atoms, 1-(alkoxycarbonyloxy)ethyl having from 4 to 7 carbon atoms, 1-methyl-1-(alkoxycarbonyloxy)ethyl having from 5 to 8 carbon atoms, N-(alkoxycarbonyl)aminomethyl having from 3 to 9 carbon atoms, 1-(N-(alkoxycarbonyl)amino)ethyl having from 4 to 10 carbon atoms, 3-phthalidyl, 4-crotonolactonyl, gamma-butyrolacton-4-yl, di-N,N—($C_1$-$C_2$)alkylamino($C_2$-$C_3$)alkyl (such as β-dimethylaminoethyl), carbamoyl-($C_1$-$C_2$)alkyl, N,N-di($C_1$-$C_2$)alkylcarbamoyl-($C_1$-$C_2$)alkyl and piperidino-, pyrrolidino- or morpholino($C_2$-$C_3$)alkyl.

Synthesis

In general, the compounds of formula (1) of this invention may be prepared by methods that include processes known in the chemical arts, particularly in light of the description contained herein. Certain processes for the manufacture of the compounds of formula (1) of this invention are illustrated by the following reaction schemes. Other processes are described in the experimental section. Some of the starting compounds for the reactions described in the schemes and Examples are prepared as illustrated herein. As used in the following schemes, the term $NR^A R^B$ means the optionally substituted $R^3$ groups consisting of heterocycloalkyl, and heteroaryl or —$NR^5 R^6$.

In Scheme A below, generalized methods for preparing the compounds of formulae (A2), (A3), and (A4) are depicted. In compound (A1), $P^1$ represents an amine protecting group. Typical protecting groups useful in the preparation of (A4) include methoxycarbonyl, tert-butoxycarbonyl (Boc), carbobenzyloxy (Cbz), and the like. The methoxycarbonyl and Boc protecting group are generally preferred

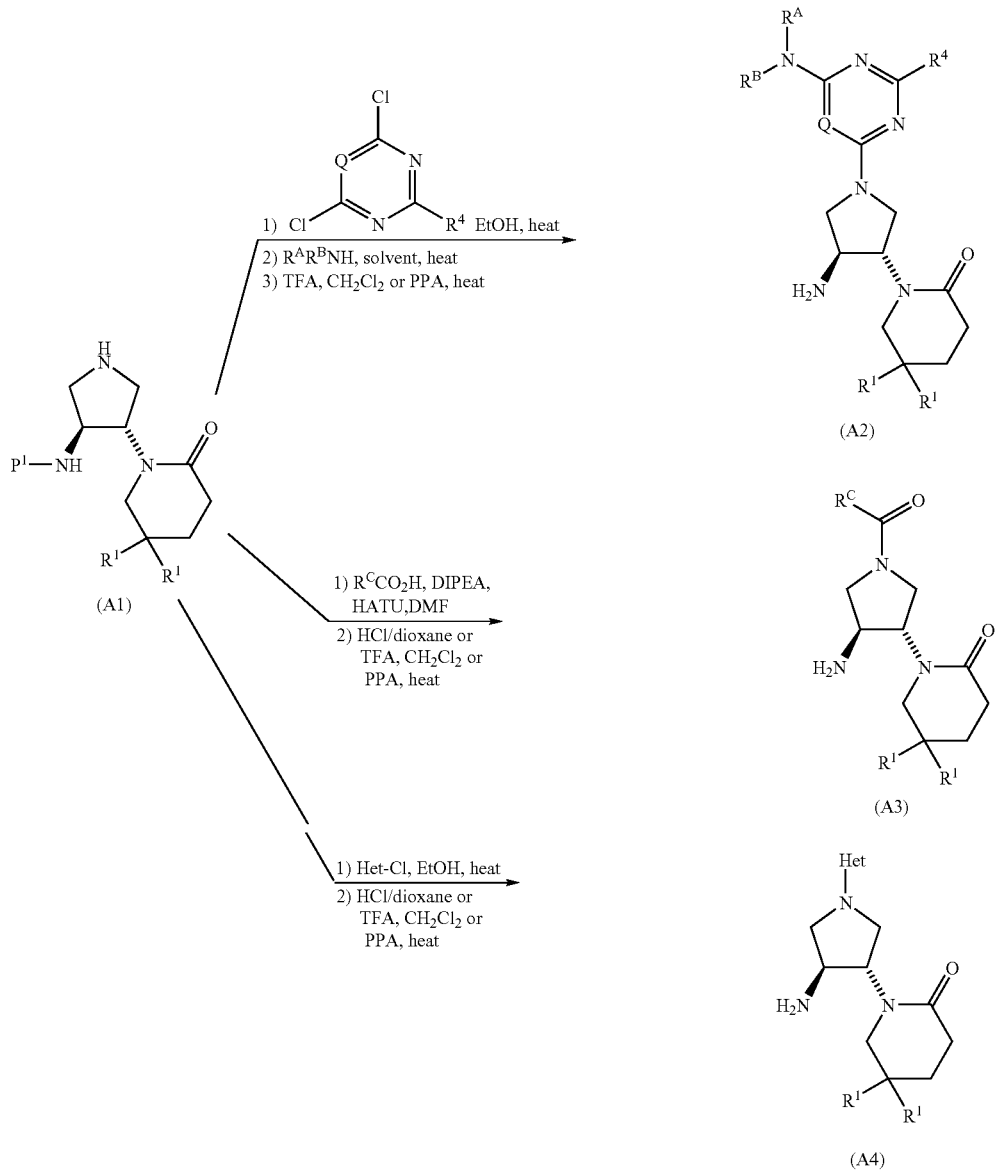

Scheme A

The compounds of formula (A2), wherein $R^A$ and $R^B$ are as defined hereinabove, may be prepared by first coupling a dichloro-pyrimidine or chloro-triazine derivative with (A4) by admixture in the presence of a trialkylamine base, such as diisopropylethylamine (DIPEA), in an alcohol, such as ethanol (EtOH). The admixture is heated, preferably at the reflux temperature of the solvent employed or in a microwave apparatus, to afford a 4-amino-6-chloropyrimidyl or 2-amino-4-chlorotriazinyl intermediate. The intermediate is then treated with an appropriately-substituted amine $R^AR^BNH$ in the presence of an organic base, preferably a trialkylamine such DIPEA, in a protic solvent, such as EtOH. The reaction is facilitated by warming, preferably at the reflux temperature of the solvent employed, or by treatment in a microwave apparatus, to afford a corresponding protected 4,6-diamino-pyrimidinyl or 2,4-diaminotriazinyl derivative. For $P^1$ as tert-butoxycarbonyl, deprotection thereof by treatment with a protic acid, preferably hydrochloric or trifluoroacetic acid (TFA), in an inert solvent such as dioxane or methylene chloride, furnishes (A2). For $P^1$ as methoxycarbonyl, deprotection thereof by treatment with warm PPA furnishes (A2).

Alternatively, the compounds of formula (A3) may be prepared by coupling (A1) with an appropriately-substituted carboxylic acid ($R^C$—COOH), wherein $R^C$ includes, for instance, benzofuranyl. The coupling is affected in a reaction-inert solvent, preferably an aprotic solvent such as acetonitrile, dichloromethane, dimethylformamide (DMF), tetrahydrofuran (THF), or chloroform. A coupling agent, such as 1-(3-dimethylaminopropyl)-3-ethylcarbodiimide hydrochloride (EDC), O-(7-azabenzotriazol-1-yl)-N,N,N',N'-tetramethyluronium hexafluorophosphate (HATU), 1,3-dicyclohexycarbodiimide (DCC), 2-ethoxy-1-ethoxycarbonyl-1,2-dihydroquinoline (EEDQ), N,N-carbonyldiimidazole (CDI), pivaloyl chloride or diethylphosphorylcyamide is then added, optionally in the presence of a base, such as triethylamine (TEA) or pyridine, and an optional adjuvant, such as 1-hydroxybenzotriazole (HOBT) or 1-hydroxy-7-azabenzotriazole (HOAT). The coupling is typically effected at a temperature of between about 0° C. and about 50° C., for a suitable time, such as from about one hour and about 24 hours, for example about 16 hours. For a discussion of conditions useful for coupling amines and carboxylic acids see Houben-Weyl, Vol. XV, Part II, E. Wunsch, Ed., G. Theime Verlag, (1974), Stuttgart; M. Bodansky, "Principles of Peptide Synthesis", Springer-Verlag Berlin (1984); and "The Peptides: Analysis, Synthesis and Biology" (ed. E. Gross and J. Meienhofer), Vols. 1-5 (Academic Press NY 1979-1983). The coupled adduct is then deprotected as described for (A1) to afford (A3).

Alternatively, the compounds of formula (A4) may be prepared by aromatic nucleophilic substitution of a halogenated heteroaryl moiety, Het-X, wherein X is a halogen, with (A1) in the presence of a base, such as DIPEA or cesium carbonate. Preferably, the halogen in Het-X is chloro. The reaction is typically effected in a solvent such as EtOH, N-methylpyrrolidinone, or tert-butanol, at a temperature of between about 25° C. and reflux temperature of the solvent employed. Microwave heating may also be used. Deprotection, as described above in the preparation of the compounds of formula (A1), affords (A4).

In Scheme B below, an exemplary method is provided for preparing compounds of formula (Ie), wherein A is a covalent bond and $R^1$ is a pyrimidyl moiety, substituted with an $R^AR^BNC(O)$— functional group.

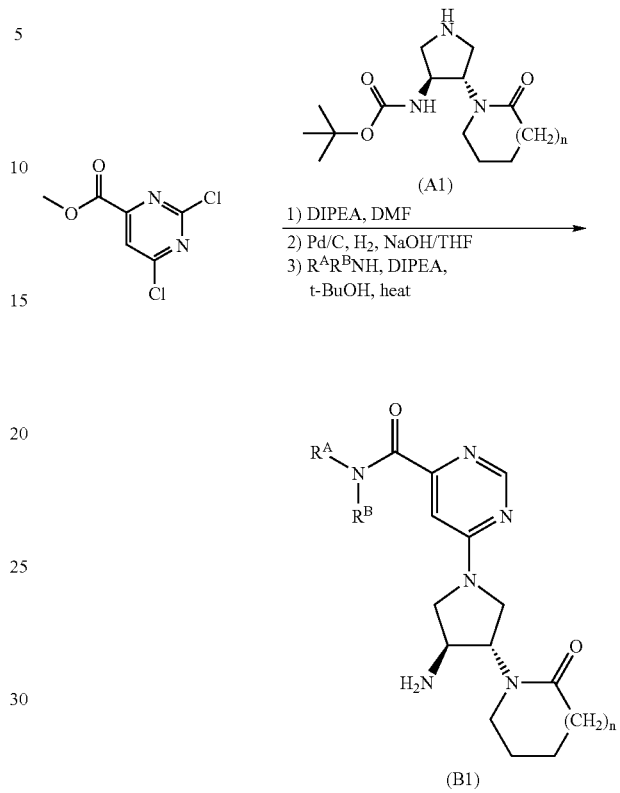

In Scheme B, methyl 2,6-dichloropyrimidine-4-carboxylate is first coupled with (A1) by admixture in an aprotic solvent, preferably DMF, to afford a methyl 6-amino-2-chloropyrimidine-4-carboxylate derivative. The coupling is effected at about −78° C. in the presence of an organic base, such as DIPEA. Dechlorination, with concomitant saponification of the carboxylate ester, is effected by agitating a solution of the ester and an alkali metal base, preferably sodium hydroxide, with a catalyst, such as palladium on carbon. The reaction is performed in a protic/inert solvent mixture, such as water/THF, under hydrogen. The resulting acid is coupled with an appropriately-substituted amine $R^AR^BNH$ to provide a protected amide intermediate. The coupling is effected employing the same reagents and conditions described above for preparing the compounds of formula (A3). Deprotection of the amide, as described above in the preparation of the compounds of formula (A1), affords (B1).

In Scheme C below, an exemplary method is provided for preparing compounds of formula (C1), wherein A is a covalent bond and $R^1$ is a pyrimidyl moiety incorporating a substituted ether (X represents oxygen) or amino (X represents nitrogen) functional group. One of ordinary skill in the art will readily appreciate that when X represents oxygen, only a single group $R^A$ or $R^B$ will be present as the oxygen atom substituent.

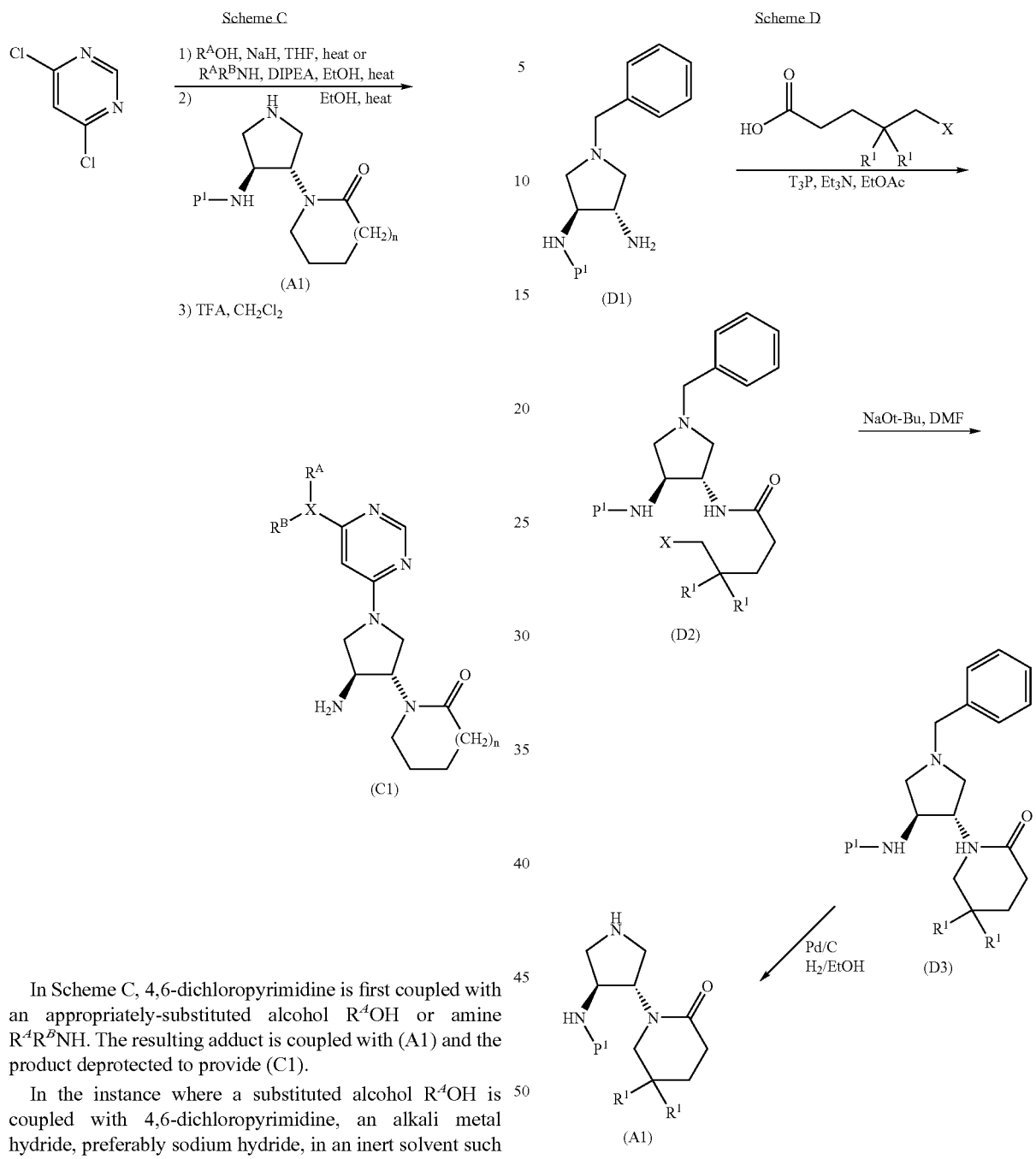

In Scheme C, 4,6-dichloropyrimidine is first coupled with an appropriately-substituted alcohol R$^A$OH or amine R$^A$R$^B$NH. The resulting adduct is coupled with (A1) and the product deprotected to provide (C1).

In the instance where a substituted alcohol R$^A$OH is coupled with 4,6-dichloropyrimidine, an alkali metal hydride, preferably sodium hydride, in an inert solvent such as THF, is employed. The alkoxide so formed is treated with 4,6-dichloropyrimidine and the mixture is warmed, preferably at about 60° C. for between about 16 and 24 hours, to afford a 4-alkoxy-6-chloropyrimidine derivative. Coupling thereof with (A1) and deprotection as described above for the compounds of formula (A3), affords (C1), wherein the oxygen is substituted with R$^A$ or R$^B$.

Where the initial coupling employs a substituted amine R$^A$R$^B$NH, the coupling conditions employed are identical to those described in Scheme A above.

In Scheme D, an exemplary method for preparing an amine of formula (A1), Scheme A wherein P$^1$ is BOC or methoxycarbonyl is shown.

Starting amine (D1) may be prepared by conventional methods. See, for example, Weingarten, et al., J. Am. Chem. Soc., 120, 9112 (1998). Amine (D1) is subsequently acylated with 5-chloro-4,4-difluorovaleric acid using a coupling agent such as DCC, T3P or HATU in the presence of a base, such as TEA, DIPEA, or pyridine in an inert solvent, such as ethyl acetate, diethyl ether, dichloromethane, or toluene at a temperature of between about 0° C. and about 80° C. Cyclization of the resulting haloamide (D2) can be effected with an inorganic base, such as sodium hydride, potassium hydride, or sodium tert-butoxide in an inert solvent, such as THF, DMF, or N-methylpyrrolidinone, at a temperature of between about 0° C. and about 80° C. Deprotection of (D3) may be performed by hydrogenolysis in the presence of catalyst, such as 10% palladium or palladium hydroxide, in a suitable solvent such as EtOH or EtOAc at a pressure of about 30 psi to about 60 psi, for a sufficient period of time, usually overnight, at a temperature of between about 20° C. and about 80° C. Preferably, hydrogenolysis is effected at a pressure of about 45 psi at room temperature. Alternatively, deprotection under transfer hydrogenation conditions using ammonium formate or cyclohexadiene may be employed.

A pharmaceutical composition of the present invention comprises a therapeutically effective amount of a compound of formula (1), or a pharmaceutically acceptable salt thereof, and a pharmaceutically acceptable carrier, vehicle, diluent or excipient. A preferred pharmaceutical composition of the present invention comprises a therapeutically effective amount of a compound of formula (2), or a pharmaceutically acceptable salt thereof, and a pharmaceutically acceptable carrier, vehicle, diluent or excipient.

A more preferred pharmaceutical composition of the present invention comprises a therapeutically effective amount of the compound 1-((3S,4S)-4-amino-1-(4-(3,3-difluoropyrrolidin-1-yl)-1,3,5-triazin-2-yl)pyrrolidin-3-yl)-5,5-difluoropiperidin-2-one, or a pharmaceutically acceptable salt thereof, and a pharmaceutically acceptable carrier, vehicle, diluent or excipient.

The pharmaceutical compositions formed by combining the compounds of this invention and the pharmaceutically acceptable carriers, vehicles or diluents are then readily administered in a variety of dosage forms such as tablets, powders, lozenges, syrups, injectable solutions and the like. These pharmaceutical compositions can, if desired, contain additional ingredients such as flavorings, binders, excipients and the like.

Thus, for purposes of oral administration, tablets containing various excipients such as sodium citrate, calcium carbonate and/or calcium phosphate, may be employed along with various disintegrants such as starch, alginic acid and/or certain complex silicates, together with binding agents such as polyvinylpyrrolidone, sucrose, gelatin and/or acacia. Additionally, lubricating agents such as magnesium stearate, sodium lauryl sulfate and talc are often useful for tabletting purposes. Solid compositions of a similar type may also be employed as fillers in soft and hard filled gelatin capsules. Preferred materials for this include lactose or milk sugar and high molecular weight polyethylene glycols. When aqueous suspensions or elixirs are desired for oral administration, the active pharmaceutical agent therein may be combined with various sweetening or flavoring agents, coloring matter or dyes and, if desired, emulsifying or suspending agents, together with diluents such as water, ethanol, propylene glycol, glycerin and/or combinations thereof.

For parenteral administration, solutions of the compounds or compositions of this invention in sesame or peanut oil, aqueous propylene glycol, or in sterile aqueous solutions may be employed. Such aqueous solutions should be suitably buffered if necessary and the liquid diluent first rendered isotonic with sufficient saline or glucose. These particular aqueous solutions are especially suitable for intravenous, intramuscular, subcutaneous and intraperitoneal administration. In this connection, the sterile aqueous media employed are all readily available by standard techniques known to those skilled in the art.

For intranasal administration or administration by inhalation, the compounds or compositions of the invention are conveniently delivered in the form of a solution or suspension from a pump spray container that is squeezed or pumped by the patient or as an aerosol spray presentation from a pressurized container or a nebulizer, with the use of a suitable propellant, e.g., dichlorodifluoromethane, trichlorofluoromethane, dichlorotetrafluoroethane, carbon dioxide or other suitable gas. In the case of a pressurized aerosol, the dosage unit may be determined by providing a valve to deliver a metered amount. The pressurized container or nebulizer may contain a solution or suspension of a compound of this invention. Capsules and cartridges (made, for example, from gelatin) for use in an inhaler or insufflator may be formulated containing a powder mix of a compound or compounds of the invention and a suitable powder base such as lactose or starch.

Methods of preparing various pharmaceutical compositions with a certain amount of active ingredient are known, or will be apparent in light of this disclosure, to those skilled in this art. For examples of methods of preparing pharmaceutical compositions, see Remington's Pharmaceutical Sciences, Mack Publishing Company, Easton, Pa., 19th Edition (1995).

In another aspect, the invention is directed to a pharmaceutical composition, which comprises a therapeutically effective amount of a first compound of formula (1), or a pharmaceutically acceptable salt of the compound, or a solvate of the compound or salt; a second compound that is an antidiabetic agent selected from insulin and insulin analogs; insulinotropin; biguamides; $\alpha_2$-antagonists and imidazolines; glitazones; aldose reductase inhibitors; glycogen phosphorylase inhibitors; sorbitol dehydrogenase inhibitors; fatty acid oxidation inhibitors; $\alpha$-glucosidase inhibitors; $\beta$-agonists; phosphodiesterase inhibitors; lipid-lowering agents; antiobesity agents; vanadate and vanadium complexes and peroxovanadium complexes; amylin antagonists; glucagon antagonists; growth hormone secretagogues; gluconeogenesis inhibitors; somatostatin analogs; antilipolytic agents; a prodrug of the antidiabetic agents, or a pharmaceutically acceptable salt of the antidiabetic agents and the prodrugs.

In another aspect, the invention is directed to a kit comprising: a first dosage form comprising a compound of formula (1), or a pharmaceutically acceptable salt of the compound, or a solvate of the compound or salt; and a second dosage form comprising an antidiabetic agent selected from insulin and insulin analogs; insulinotropin; biguamides; $\alpha_2$-antagonists and imidazolines; glitazones; aldose reductase inhibitors; glycogen phosphorylase inhibitors; sorbitol dehydrogenase inhibitors; fatty acid oxidation inhibitors; $\alpha$-glucosidase inhibitors; $\beta$-agonists; phosphodiesterase inhibitors; lipid-lowering agents; antiobesity agents; vanadate and vanadium complexes and peroxovanadium complexes; amylin antagonists; glucagon antagonists; growth hormone secretagogues; gluconeogenesis inhibitors; somatostatin analogs; antilipolytic agents; prodrugs of the antidiabetic agents, or a pharmaceutically acceptable salts of the antidiabetic agents and the prodrug; and a container for containing said first dosage (a) and said second dosage (b). In a preferred embodiment of the kit, both the first and the second dosage forms independently comprise a pharmaceutically acceptable carrier or diluent.

In another aspect, the invention is directed to a method of inhibiting dipeptidyl peptidase-IV comprising administering to a mammal an inhibitory amount of a compound of formula (1), or a pharmaceutically acceptable salt of the compound, or a solvate of the compound or salt; either alone or in combination with an antidiabetic agent as described above.

In another aspect, the invention is directed to a method of treating a condition mediated by dipeptidyl peptidase-IV inhibition comprising administering to a mammal in need of such treatment a therapeutically effective amount of a compound of formula (1), or a pharmaceutically acceptable salt of the compound, or a solvate of the compound or salt; either alone or in combination with an antidiabetic agent as described above.

In the present invention, typically, the condition treated is Type 2 diabetes, Type 1 diabetes, impaired glucose tolerance, hyperglycemia, metabolic syndrome or a diabetic complication such as diabetic neuropathy, diabetic nephropathy, diabetic retinopathy, diabetic cardiomyopathy and diabetes-related cataracts. Preferably, the condition treated is Type 2 diabetes.

In an alternate embodiment, the condition treated is glucosuria, metabolic acidosis, arthritis, obesity, conditions exacerbated by obesity, hypertension, hyperlipidemia, atherosclerosis, osteoporosis, osteopenia, frailty, bone loss, bone fracture, acute coronary syndrome, short stature due to growth hormone deficiency, infertility due to polycystic ovary syndrome, anxiety, depression, insomnia, chronic fatigue, epilepsy, eating disorders, chronic pain, alcohol addiction, diseases associated with intestinal motility, ulcers, irritable bowel syndrome, inflammatory bowel syndrome, short bowel syndrome and cancer.

In another aspect, the invention is directed to a method of identifying an insulin secretagogue agent for diabetes, comprising: administering an agent of formula (1) to a fasted, diabetic KK/H1J symptomatic mouse; and assessing a response in the mouse to a subsequent oral glucose challenge, wherein, if said mouse demonstrates an improvement in the symptoms, said agent is identified as a treatment for Type 2 diabetes, Type 1 diabetes, impaired glucose tolerance, hyperglycemia, metabolic syndrome (syndrome X and/or insulin resistance syndrome), glucosuria, metabolic acidosis, arthritis, cataracts, diabetic neuropathy, diabetic nephropathy, diabetic retinopathy, diabetic cardiomyopathy, obesity, conditions exacerbated by obesity, hypertension, hyperlipidemia, atherosclerosis, osteoporosis, osteopenia, frailty, bone loss, bone fracture, acute coronary syndrome, short stature due to growth hormone deficiency, infertility due to polycystic ovary syndrome, anxiety, depression, insomnia, chronic fatigue, epilepsy, eating disorders, chronic pain, alcohol addiction, diseases associated with intestinal motility, ulcers, irritable bowel syndrome, inflammatory bowel syndrome; short bowel syndrome, and to prevent disease progression in Type 2 diabetes.

The present invention also relates to therapeutic methods for treating or preventing the above described conditions in a mammal, including a human, wherein a compound of formula (1) of this invention is administered as part of an appropriate dosage regimen designed to obtain the benefits of the therapy. The appropriate dosage regimen, the amount of each dose administered and the intervals between doses of the compound will depend upon the compound of formula (1) of this invention being used, the type of pharmaceutical compositions being used, the characteristics of the subject being treated and the severity of the conditions.

In general, an effective dosage for the compounds of the present invention is in the range of 0.01 mg/kg/day to 30 mg/kg/day, preferably 0.01 mg/kg/day to 5 mg/kg/day of active compound in single or divided doses. Some variation in dosage will necessarily occur, however, depending on the condition of the subject being treated. The individual responsible for dosing will, in any event, determine the appropriate dose for the individual subject. Practitioners will appreciate that "kg" refers to the weight of the patient measured in kilograms.

The compounds or compositions of this invention may be administered in single (e.g., once daily) or multiple doses or via constant infusion. The compounds of this invention may also be administered alone or in combination with pharmaceutically acceptable carriers, vehicles or diluents, in either single or multiple doses. Suitable pharmaceutical carriers, vehicles and diluents include inert solid diluents or fillers, sterile aqueous solutions and various organic solvents.

The compounds or compositions of the present invention may be administered to a subject in need of treatment by a variety of conventional routes of administration, including orally and parenterally, (e.g., intravenously, subcutaneously or intramedullary). Further, the pharmaceutical compositions of this invention may be administered intranasally, as a suppository, or using a "flash" formulation, i.e., allowing the medication to dissolve in the mouth without the need to use water.

Exemplification

The Examples set forth herein below are for illustrative purposes only. The compositions, methods, and various parameters reflected herein are intended only to exemplify various aspects and embodiments of the invention, and are not intended to limit the scope of the claimed invention in any way.

Unless noted otherwise, all reactants were obtained commercially.

Flash chromatography was performed according to the method described by Still et al., J. Org. Chem., 1978, 43, 2923.

All Biotage® purifications, discussed herein, were performed using either a 40M or 40S Biotage® column containing KP-SIL silica (40-63 µM, 60 Angstroms) (Bioatge AB; Uppsala, Sweden).

All Combiflash® purifications, discussed herein, were performed using a CombiFlash® Companion system (Teledyne Isco; Lincoln, Nebr.) utilizing packed RediSep® silica columns Mass Spectra were recorded on a Waters (Waters Corp.; Milford, Mass.) Micromass Platform II spectrometer. Unless otherwise specified, mass spectra were recorded on a Waters (Milford, Mass.) Micromass Platform II spectrometer.

Proton NMR chemical shifts are given in parts per million downfield from tetramethylsilane and were recorded on a Varian Unity 400 MHz (megaHertz) spectrometer (Varian Inc.; Palo Alto, Calif.). NMR chemical shifts are given in parts per million downfield from tetramethylsilane (for proton) or fluorotrichloromethane (for fluorine).

The following preparations were used in the synthesis of compounds of the present invention which are further exemplified in the following examples.

Preparation 1 tert-butyl (3S,4S)-4-(5,5-difluoro-2-oxopiperidin-1-yl)pyrrolidin-3-ylcarbamate

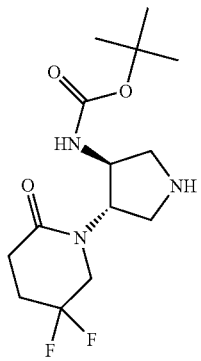

Step 1: (3S,4S)-1-Benzyl-3,4-dihydroxyiyrrolidine-2,5-dione

Benzylamine (75 g, 0.70 mol) and (−)-tartaric acid (100 g, 700 mol) were heated in boiling xylene (1.0 L) in a Dean-Stark apparatus. After cooling, the product was collected, washed with acetone, and recrystallized from EtOH to afford the product (120 g, 77%). $^1$H NMR (400 MHz, CDCl$_3$) δ 7.39-7.20 (5H, m), 6.27 (2H, d), 4.58 (1H, d), 4.52 (1H, d), 4.38 (2H, m).

Step 2: (3R,4R)-1-Benzylpyrrolidine-3,4-diol

To a mechanically stirred and cooled solution (0° C.) of the product from Step 1 (50 g, 0.23 mol) in dry THF (1.24 L) was added sodium aluminum hydride bis-(methoxyethoxide) (289 mL of a 65% Red-A;®/Toluene solution, 0.95 mol) under a nitrogen atmosphere at such a rate that the internal temperature did not exceed 20° C. The reaction mixture was allowed stir at room temperature for 2 h after the addition was complete. The reaction mixture was slowly poured into ice water (1.0 L) with stirring to quench the reaction. After warming to room temperature, 30% ammonium hydroxide (100 mL) was added followed by EtOAc (1.5 L) and this mixture was stirred for 16 h. The suspension was filtered through diatomaceous earth and the solids were washed with EtOAc. The filtrate layers were separated and the organic phase was dried over sodium sulfate and concentrated to afford a syrup. Dissolution in dichloromethane and concentration affords a white solid that is collected and dried (43.7 g, 86%). $^1$H NMR (400 MHz, CDCl$_3$) δ 7.36-7.23 (5H, m), 6.23 (2H, m), 4.65 (1H, m), 4.15-4.00 (3H, m), 3.62-3.49 (1H, dd), 3.33 (1H, dd), 3.14 (1H, dd), 2.94 (1H dd). MS m/z 194 (MH$^+$).

Step 3: (3R,4R)-1-Benzyl-3,4-bis(methylsulfonyloxy)pyrrolidine

To an ice-cold (0-5° C.) solution of the product from Step 2 (5.27 g, 27.3 mmol) and TEA (8.27 g, 81.9 mmol) in dichloromethane (50 mL), was added methanesulfonyl chloride (6.87 g, 60.0 mmol) over a period of 30 minutes. After stirring at RT overnight, the reaction mixture was washed with water. The organic layer was dried (sodium sulfate), filtered, and concentrated to give the crude product which was purified over a silica column (5:95 EtOAc/hexane) to obtain pure product (6.44 g, 67.6%). $^1$H NMR (400 MHz, CDCl$_3$) δ 7.32-7.26 (5H, m), 5.14 (2H, m), 3.65 (2H, s), 3.15-3.08 (2H, m), 3.08 (6H, s), 2.76 (2H, dd). MS m/z 350 (MH$^+$).

Step 4: (3S,4S)-3,4-Diazido-1-benzylpyrrolidine

The product of Step 3 (11.4, 32.66 mmol) and sodium azide (6.36 g, 97.98 mmol) in dry DMF (120 mL) was heated at 100° C. for 16 hours. Upon cooling to RT, the reaction mixture was concentrated and the residue was partitioned between water (250 mL) and EtOAc (3×200 mL). The combined organic extracts were dried over sodium sulfate and evaporated. Purification by flash chromatography on silica gel (98:2 petroleum ether/EtOAc) afforded the product (5.6 g, 70.5%) as colorless solid. $^1$H NMR (400 MHz, CDCl$_3$) δ 7.32 (5H,s) 3.89 (2H, t), 3.68 (2H, m), 3.00 (2H, dd), 2.63 (2H, dd). MS m/z 244 (MH$^+$).

Step 5: (3S,4S)-3-Azido 4-amino N-benzylpyrrolidine

To a solution of the product from Step 4 (38.4 g, 158 mmol) in tetrahydrofuran (430 mL) was added triphenylphosphine (35.2 g, 134 mmol) and water (5.69 g, 316 mmol). The solution was stirred at room temperature until gas evolution had ceased and stirred at reflux for one hour. The reaction was cooled to RT and concentrated and the residue was dissolved in 4.0 N aqueous HCl (300 mL). The resultant mixture was extracted with chloroform (2×200 mL) and the aqueous phase was basified to pH 10 with concentrated aqueous ammonium hydroxide. This mixture was extracted with chloroform (3×300 mL) and the combined organic extracts were dried over sodium sulfate and concentrated to afford the 27.9 g (96%) of the product as an oil. MS m/z 218.3 (AP$^+$100).

Step 6: N-((3S,4S)-4-azido-1-benzylpyrrolidin-3-yl)-5-bromo-4,4-difluoropentanamide To a solution of the product from Step 5 (17.5 g, 80.6 mmol), 5-bromo-4,4-difluoropentanoic acid (17.5 g, 80.6 mmol) from Preparation 3 and triethylamine (32.6 g, 323 mmol) in ethyl acetate (250 mL) was added a 50% solution of propanephosphonic acid cyclic anhydride in ethyl acetate (48.0 mL, 80.6 mmol). The reaction was warmed to reflux and stirred for 16 hours. The reaction was cooled to room temperature and partitioned between ethyl acetate and H$_2$O. The organic phase washed with saturated sodium carbonate solution and saturated sodium chloride solution and then dried over sodium sulfate and concentrated to provide 22.0 g (65%) of the product as an oil. MS m/z 416. (MH$^+$).

Step 7: 1-((3S,4S)-4-azido-1-benzylpyrrolidin-3-yl)-5,5-difluoropiperidin-2-one To a solution of the product from Step 6 (22.0 g, 52.8 mmol) in N,N-dimethylformamide (220 mL) was added sodium hydride (60% suspension in mineral oil, 3.38 g, 84.6 mmol) in several portions. The reaction was stirred at room temperature for 16 hours and then ice water (50 mL) was added slowly. The resulting mixture was partitioned between ethyl acetate and H$_2$O and the organic phase washed with 2% aqueous lithium chloride solution and then brine. The organic layer was dried over sodium sulfate and concentrated to an oil that was separated by silica gel chromatography (75M Biotage Si1 (A Dynax Corp.; Charlottesville, Va.) eluting with a pentane/EtOAc gradient (4:1-1:1) to afford 17.7 g (53%) of the product as a solid. MS m/z 336.3 (AP⁺100).

Step 8: 1-((3S,4S)-4-amino-1-benzylpyrrolidin-3-yl)-5,5-difluoropiperidin-2-one

To a solution of the product of Step 7 (8.50 g, 25.3 mmol) in tetrahydrofuran (85 mL) was added triphenylphosphine (6.65 g, 25.3 mmol) and H₂O (0.91 g, 50.7 mmol). The solution was stirred at reflux for 3 hours and then cooled to room temperature and concentrated. The residue was dissolved in 4.0 N aqueous HCl (200 mL) and extracted with chloroform (200 mL). The aqueous layer was basified to pH 10 with concentrated aqueous ammonium hydroxide solution and the resulting mixture was extracted with chloroform (2×300 mL). The combined organic extracts were dried over sodium sulfate and concentrated to afford 7.84 g (99%) of the product as a solid. MS m/z 310.3 (AP⁺100).

Step 9: tert-butyl (3S,4S)-1-benzyl-4-(5,5-difluoro-2-oxopiperidin-1-yl)pyrrolidin-3-ylcarbamate To a solution of the product from Step 8 (7.84 g, 25.3 mmol) in dichloromethane (400 mL) was added di-tert-butyl-dicarbonate (5.81 g, 26.6 mmol). The reaction was stirred at room temperature for 2 hours and then concentrated. The residue was triturated with di-isopropyl ether to afford 9.50 g (91%) of the product as a white solid. MS m/z 410.4 (AP⁺70).

Step 10

To a solution of the product of Step 9 (2 g, 0.06 mmol) in methanol was added excess ammonium formate and 10% Pd/C. The reaction mixture was heated under reflux overnight. After filtering, the solution was evaporated and residue was purified on silica gel (10% methanol/chloroform) to obtain the title product (800 mg). ¹H NMR (400 MHz, CDCl₃) δ 5.25 (1H,s), 4.7 (1H, m), 3.45 (1H, m), 3.25 (1H, m), 3.04 (m) 2.9 (1H, m), 2.5 (6H, m), 1.80 (4H, m), 1.45 (9H, s). MS m/z 284 (MH⁺).

Preparation 2

Methyl (3S,4S)-4-(5,5-difluoro-2-oxopiperidin-1-yl) pyrrolidin-3-ylcarbamate

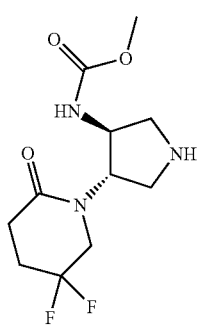

Step 1: (3aS,6aR)-5-Benzyl-2,2-dioxo-tetrahydro-1-oxa-2λ⁶-thia-3,5-diaza-pentalene-3-carboxylic acid methyl ester To a solution of the product from Preparation 1, Step 2 (6.4 g, 33.1 mmol) in 1,4-dioxane (70 mL) was added (methoxy-carbonylsulfamoyl)triethylammonium hydroxide, inner salt (19.7 g, 82.8 mol). After stirring at room temperature for 5 min, the solution was warmed to 105° C. and stirred at that temperature for 1.5 h. The solution was cooled to room temperature, concentrated and partitioned between EtOAc (300 mL) and H₂O (100 mL). The layers were separated and the organic phase washed with saturated sodium chloride, dried over sodium sulfate and concentrated to give the cyclic sulfamate product as a syrup that solidifies upon standing (10.3 g, 61.9%). ¹H NMR (400 MHz, Chloroform-d) δ 7.39-7.23 (m, 5H), 5.19-5.13 (m,1H), 4.68-4.61 (m, 1H), 3.90 (s, 3H), 3.78-3.62 (q, 2H), 3.20-3.10 (m, 2H), 2.69-2.59 (m, 2H). MS m/z 269.1 (MH⁺).

Step 2: [(3S,4S)-1-Benzyl-4-(1,3-dioxo-1,3-dihydro-isoindol-2-yl)-pyrrolidin-3-yl]-carbamic acid methyl ester To a solution of the product from Step 1 (6.30 g, 20.2 mmol) in N,N-dimethyl formamide (32 mL) was added potassium phthalimide (5.98 g, 32.3 mmol). This mixture was heated to 80° C. and maintained at that temperature for 2 h. The reaction was cooled to room temperature and 2N HCl (32 mL) was added followed by warming to 40° C. for 1 h. The solution was cooled to 0° C., EtOAc (500 mL) was added and the pH of the aqueous phase was adjusted to 8-9 with saturated sodium bicarbonate solution. The organic phase was separated and washed with 2% lithium chloride solution (2×100 mL) and saturated sodium chloride solution (100 mL). The organic layer was then dried over sodium sulfate and concentrated to an oil that was separated by silica gel chromatography (Biotage 25+S (A Dynax Corp.; Charlottesville, Va.) eluting with a pentane/EtOAc gradient (4:1-1:1) to afford 3.60 g (47.0%) of the product as a white solid. ¹H NMR (400 MHz, Chloroform-d) δ 7.86-7.78 (m, 2H), 7.72-7.66 (m, 2H), 7.35-7.22 (m, 5H), 5.36-5.23 (br s, 1H), 4.68-4.54 (m, 2H), 3.66 and 3.57 (s, 3H), 3.69-3.53 (m, 2H), 3.15-3.03 (m, 2H), 2.84-2.74 (m, 1H), 2.73-2.65 (m, 1H). MS 380.2 (AP⁺, 100).

Step 3: ((3S,4S)-4-Amino-1-benzyl-pyrrolidin-3-yl)-carbamic acid methyl ester

A solution of the product from Step 2 (3.60 g, 9.49 mmol) and anhydrous hydrazine (0.61 g, 19.0 mmol) in ethanol (36 mL) was heated at reflux temperature for 2 h. The reaction was cooled to room temperature and the precipitate was removed by filtration and washed with ethanol. The filtrate was concentrated to dryness and the residue was dissolved in EtOAc and washed with saturated sodium bicarbonate solution. The organic layer was then dried over sodium sulfate, filtered and concentrated to an oil that solidified upon standing to afford 2.20 g (93%) of the product as a white solid. ¹H NMR (400 MHz, Chloroform-d) δ 7.36-7.22 (m, 5H), 5.12-5.00 (br s, 1H), 3.74-3.57 (m, 1H), 3.64 (s, 3H), 3.63-3.54 (m, 2H), 3.34-3.25 (m, 1H), 3.14-3.02 (m, 1H), 2.88-2.53 (m, 1H), 2.54-2.42 (m, 1H), 2.17-2.10 (m, 1H) 2.00-1.60 (br s, 2H). MS 250.3 (AP⁺, 100).

Step 4: [(3S,4S)-1-Benzyl-4-(5-chloro-4,4-difluoro-pentanoylamino)-pyrrolidin-3-yl]-carbamic acid methyl ester A solution of the product from Step 3 (2.20 g, 8.82 mmol), 4,4-difluoro-5-chloropentanoic acid (1.52 g, 8.82 mmol) and triethylamine (3.57 g, 35.3 mmol) in EtOAc (25 mL) was stirred as propanephosphonic acid cyclic anhydride (5.25 mL of a 50% solution of in EtOAc, 8.82 mmol) was added in one portion. After heating at reflux overnight, the reaction was cooled to room temperature, diluted with EtOAc (300 mL) and washed with saturated sodium carbonate solution. The organic layer was dried over sodium sulfate and concentrated to an oil that was separated by silica gel chromatography (Biotage 25+S (A Dynax Corp.; Charlottesville, Va.) eluting with a dichloromethane/methanol/ammonium hydroxide gradient (100:0:0-95:5:0.25). The desired fractions were concentrated and triturated with di-isopropylether to afford 3.56 g (70%) of the product as a white solid. $^1$H NMR (400 MHz, Chloroform-d) δ 7.36-7.22 (m, 5H), 6.14-6.00 (br s, 1H), 5.17-5.04 (br s, 1H), 4.17-4.04 (br m, 1H), 4.00-3.86 (br m, 1H), 3.74-3.49 (m, 4H), 3.65 and 3.63 (s, 3H), 3.12-2.94 (m, 2H), 2.49-2.43 (m, 1H), 2.42-2.49 (m, 4H). MS 404.2 (AP$^+$, 100).

Step 5: [(3S,4S)-1-Benzyl-4-(5,5-difluoro-2-oxo-piperidin-1-yl)-pyrrolidin-3-yl]-carbamic acid methyl ester A solution of the product from Step 4 (0.50 g, 1.24 mmol) in N,N-dimethylformamide (3.0 mL) was cooled to 0° C. and sodium tert-butoxide (0.24 g, 2.54 mol) was added. The reaction was stirred and warmed to room temperature over 1.5 hours. The reaction was quenched by the addition of ice (50 g) and the resulting mixture was diluted with H$_2$O (20 mL), methyl tert-butyl ether (30 mL) and ethyl acetate (100 mL). The organic layer was separated, washed with a 2% lithium chloride solution (20 mL) and then saturated sodium chloride solution (20 mL). The organic layer was dried over sodium sulfate and concentrated to afford a solid that was triturated with a 1:1 cyclohexan/heptane mixture to provide 0.31 g (68%) of the product as a light-yellow solid. $^1$H NMR (400 MHz, Methanol-d$_4$) δ 7.38-7.18 (m, 5H), 4.87-4.51 (m, 1H), 4.22-4.11 (m, 1H), 3.94-3.48 (m, 4H), 3.59 (s, 3H), 3.22-3.07 (m, 1H), 2.78-2.64 (m, 2H), 2.61-2.43 (m, 2H), 2.40-2.13 (m, 3H). MS 368.2 (AP$^+$, 100).

Step 6: [(3S,4S)-4-(5,5-Difluoro-2-oxo-piperidin-1-yl)-pyrrolidin-3-yl]-carbamic acid methyl ester To a solution of the product from Step 5 in a 2:1 mixture of ethanol/acetic acid (30 mL) was added palladium hydroxide on carbon powder (0.13 g, 10 wt. %). The mixture was degassed and shaken under an atmosphere of hydrogen (75 psi) at 50° C. for 12 hours. The mixture was cooled to room temperature, filtered through diatomaceous earth and the solids washed with ethanol. The filtrate was concentrated and the residue was dissolved in saturated sodium carbonate solution and extracted with chloroform (3×50 mL). The combined organic phases were dried over sodium sulfate and concentrated to afford 0.98 g (86.6%) of the product as a foam. $^1$H NMR (400 MHz, Methanol-d$_4$) δ 4.49 (q, 1H), 4.20 (q, 1H), 3.86-3.67 (m, 2H), 3.61 (s, 3H), 3.28-3.21 (m, 1H), 3.19-3.09 (m, 1H), 2.96-2.87 (m, 1H), 2.74-2.64 (m, 1H), 2.63-2.47 (m, 2H), 2.38-2.23 (m, 2H). MS 278.3 (AP$^+$, 100).

Preparation 3

5-Bromo-4,4-difluoropentanoic acid

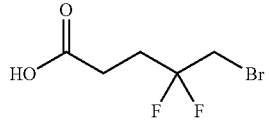

Step 1

To a solution of ethyl 4-chloro-4-oxobutyrate (10.0 g, 60.8 mmol) in acetonitrile (100 mL) was added (trimethylsilyl)-diazomethane (39.5 mL of a 2.0 M solution in diethyl ether, 60.8 mmol) over a period of 30 min. After stirring at room temperature for 30 min, the reaction was cooled to −20° C. and 33% hydrogen bromide in acetic acid (14.3 mL, 79.0 mmol) was slowly added over 20 min. The reaction was warmed to room temperature and stirred for 16 h and the solvent was removed without heating. The residue was dissolved in EtOAc (200 mL) and washed with saturated sodium bicarbonate solution and saturated sodium chloride solution. The organic phase was dried over sodium sulfate and concentrated to provide 13.5 g (99%) of the product as an oil. This product contains 33% of the 5-chloro adduct. $^1$H NMR (400 MHz, Chloroform-d) δ 4.14 (Cl—CH$_2$—, s, 0.6H), 4.12 (q, 2H), 3.95 (Br—CH$_2$—, s, 1.4H), 2.87 (t, 2H), 2.64 (t, 2H), 1.24 (t, 3H).

Step 2: 5-Bromo-4,4-difluoropentanoic acid ethyl ester

To a solution of the product from Step 1 (13.6 g, 61 mmol) in methylene chloride (130 mL) at 0° C. was added, in dropwise fashion, diethylaminosulfurtrifluoride (19.6 g, 121 mmol). The mixture was warmed to room temperature and stirred for 16 hours. The reaction was diluted with dichloromethane (100 mL) and the pH was adjusted to 8 by the addition of saturated sodium bicarbonate solution (100 mL) and solid sodium bicarbonate. The organic phase was separated, washed with saturated sodium chloride solution, dried over sodium sulfate and concentrated to afford 14.2 g (95%) of the product as an oil. This product contains 33% of the 5-chloro adduct. $^1$H NMR (400 MHz, Chloroform-d) δ 4.15 (q, 2H), 3.67 (C$_1$—CH$_2$—, t, 0.6H), 3.52 (Br—CH$_2$—, t, 1.4H), 2.54 (t, 2H), 2.43-2.28 (m, 2H), 1.26 (t, 3H).

Step 3: 5-Bromo-4,4-difluoro-pentanoic acid

A solution of the product from Step 2 (14.2 g, 57.9 mmol) in a 5:1 methanol/H$_2$O solvent mixture (240 mL) was stirred as lithium hydroxide mono-hydrate (7.29 g, 174 mmol) was added. After stirring at room temperature for 2 h, the reaction volume was concentrated and the remainder was partitioned between dichloromethane (300 mL) and 4N HCl (100 mL). The organic phase was separated, dried over sodium sulfate and concentrated to afford 8.60 g (68%) of the product as a white solid. This product contains 33% of the 5-chloro adduct. $^1$H NMR (400 MHz, Chloroform-d) δ 3.67 (t, 0.6H), 3.53 (t, 1.4H), 2.62 (t, 2H), 2.43-2.28 (m, 2H). 5-Chloro-4,4- difluoro-pentanoic acid can be prepared in an analogous fashion by substituting HCl in dioxane for the HBr in acetic acid in Step 1.

Preparation 4 tert-butyl (3S,4S)-4-(2-Oxopiperidin-1-yl)pyrrolidin-3-ylcarbamate

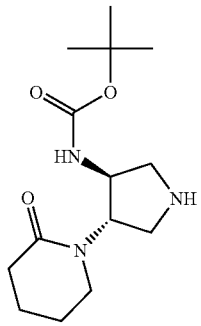

Step 1: (3S,4S)-1-Benzyl-3,4-dihydroxypyrrolidine-2,5-dione

Benzylamine (75 g, 0.70 mol) and (−)-tartaric acid (100 g, 700 mol) were heated in boiling xylene (1.0 L) in a Dean-Stark apparatus. After cooling, the product was collected, washed with acetone, and recrystallized from EtOH to afford the product (120 g, 77%). $^1$H NMR (300 MHz, CDCl$_3$) δ 7.39-7.20 (5H, m), 6.27 (2H, d), 4.58 (1H, d), 4.52 (1H, d), 4.38 (2H, m).

Step 2: (3R,4R)-1-Benzylpyrrolidine-3,4-diol

To a mechanically stirred and cooled solution (0° C.) of the product from Step 1 (50 g, 0.23 mol) in dry THF (1.24 L) was added sodium aluminum hydride bis-(methoxyethoxide) (289 mL of a 65% Red-Al®/Toluene solution, 0.95 mol) under a nitrogen atmosphere at such a rate that the internal temperature did not exceed 20° C. The reaction mixture was allowed stir at room temperature for 2 h after the addition was complete. The reaction mixture was slowly poured into ice water (1.0 L) with stirring to quench the reaction. After warming to room temperature, 30% ammonium hydroxide (100 mL) was added followed by EtOAc (1.5 L) and this mixture was stirred for 16 h. The suspension was filtered through diatomaceous earth and the solids were washed with EtOAc. The filtrate layers were separated and the organic phase was dried over sodium sulfate and concentrated to afford a syrup. Dissolution in methylene chloride and concentration affords a white solid that is collected and dried (43.7 g, 86%). $^1$H NMR (300 MHz, CDCl$_3$) δ 7.36-7.23 (5H, m), 6.23 (2H, m), 4.65 (1H, m), 4.15-4.00 (3H, m), 3.62-3.49 (1H, dd), 3.33 (1H, dd), 3.14 (1H, dd), 2.94 (1H dd). MS m/z 194 (MH$^+$).

Step 3: (3R,4R)-1-Benzyl-3,4-bis(methylsulfonyloxy)pyrrolidine

To an ice-cold (0-5° C.) solution of the product from Step 2 (5.27 g, 27.3 mmol) and TEA (8.27 g, 81.9 mmol) in dichloromethane (50 mL), was added methanesulfonyl chloride (6.87 g, 60.0 mmol) over a period of 30 minutes. After stirring at RT overnight, the reaction mixture was washed with water. The organic layer was dried (sodium sulfate), filtered, and concentrated to give the crude product which was purified over a silica column (5:95 EtOAc/hexane) to obtain pure product (6.44 g, 67.6%). $^1$H NMR (300 MHz, CDCl$_3$) δ 7.32-7.26 (5H, m), 5.14 (2H, m), 3.65 (2H, s), 3.15-3.08 (2H, m), 3.08 (6H, s), 2.76 (2H, dd). MS m/z 350 (MH$^+$).

Step 4: (3S,4S)-3,4-Diazido-1-benzylpyrrolidine

The product of Step 3 (11.4, 32.66 mmol) and sodium azide (6.36 g, 97.98 mmol) in dry DMF (120 mL) was heated at 100° C. for 16 hours. Upon cooling to RT, the reaction mixture was concentrated and the residue was partitioned between water (250 mL) and EtOAc (3×200 mL). The combined organic extracts were dried over sodium sulfate and evaporated. Purification by flash chromatography on silica gel (98:2 petroleum ether/EtOAc) afforded the product (5.6 g, 70.5%) as colorless solid. $^1$H NMR (300 MHz, CDCl$_3$) δ 7.32 (5H,s) 3.89 (2H, t), 3.68 (2H, m), 3.00 (2H, dd), 2.63 (2H, dd). MS m/z 244 (MH$^+$).

Step 5: (3S,4S)-3-Azido 4-N-Boc-amino N-benzylpyrrolidine

To a solution of the product from Step 4 (2.8 g, 11.5 mmol) in toluene (150 mL) was added triphenylphosphine (3.02 g, 11.5 mmol). The solution was stirred at reflux for one hour, cooled to RT, and water (0.41 mg, 23.04 mmol) and THF (24 mL) were added. After refluxing for an additional hour the solution was cooled and concentrated. The residue was diluted with dichloromethane (50 mL) followed by the addition of Boc$_2$O (5.02 g, 23.04 mmol). The reaction mixture was stirred overnight, washed with saturated sodium bicarbonate, dried over sodium sulfate, and concentrated. The residue was purified by column chromatography on silica gel (90:10 petroleum ether/EtOAc) to furnish the product (2.8 g, 82.6% overall). $^1$H NMR (300 MHz, CDCl$_3$) δ 7.34 (5H, m), 4.90 (1H, m), 4.04 (1H, m), 3.78 (1H, m), 3.62 (1H, d, 3.59 (1H, d), 3.04 (1H, dd), 2.84 (1H, dd), 2.46 (1H, dd), 2.39 (1H, dd), 1.45 (9H, s). MS m/z 318 (MH$^+$).

Step 6: (3S,4S)-3-Amino 4-N-Boc-amino N-benzylpyrrolidine

To a solution of the product of Step 5 (5.72 g, 18.04 mmol) in toluene (600 mL) was added triphenylphosphine (9.46 g, 36.06 mmol). The solution was stirred at reflux for one hour, cooled to RT, and water (600 mg, 33.0 mmol) and THF (45 mL) were added. After refluxing for an additional hour the solution was cooled and evaporated. The residue was purified by column chromatography on silica gel (EtOAc) to furnish the product (5.2 g, 99%) as a colorless oil. $^1$H NMR (300 MHz, CDCl$_3$) δ 7.32-7.19 (5H, m), 5.80 (1H, d), 3.95 (1H, s), 3.84 (1H, d), 3.80 (1H, d), 3.45 (1H, d), 3.30 (1H, m), 3.10 (1H, m), 2.80 (1H, dd), 2.60 (1H, dd), 1.40 (9H, s). MS m/z 292 (MH$^+$).

Step 7: tert-butyl (3S,4S)-4-(5-Bromopentanamido)-1-benzylpyrrolidin-3-ylcarbamate To a solution of the product of Step 6 (5.2 g, 17.86 mmol) and TEA (1.98 g, 19.98 mmol) in dichloromethane (200 mL) was added 5-bromovaleryl chloride (3.74 g, 18.76 mmol) dropwise. The reaction mixture was allowed to stir overnight. The solution washed with water (150 mL) and saturated sodium bicarbonate (50 mL), and evaporated. The residue was purified on silica gel (10% MeOH/chloroform) to afford the product (6.3 g, 78%). $^1$H NMR (300 MHz, CDCl$_3$) δ 7.32-7.20 (5H, s), 6.20 (1H, s), 5.0 (1H, s), 4.36 (1H, m), 4.18 (1H, m), 3.9 (1H, m), 3.62 (1H, d), 3.58 (1H, d), 3.40 (2H, t), 3.20-3.00 (2H, m), 2.60-2.50 (3H, m), 2.40 (1H, m), 1.95-1.65 (4H, m), 1.40 (9H, m). MS m/z 454 and 456 (MH$^+$).

Step 8: tert-butyl (3S,4S)-1-Benzyl-4-(2-oxopiperidin-1-yl)pyrrolidin-3-ylcarbamate To a solution of the product of Step 7 (6.3 g, 13.9 mmol) in THF (60 mL) and DMF (30 mL) was added sodium hydride (611 mg, 60% in oil, 15.29 mmol). After stirring the reaction mixture overnight at RT, it was quenched with water and extracted with EtOAc (3×100 mL). The combined extracts were washed with brine, dried over sodium sulfate, filtered, and concentrated to furnish the crude product. The residue was purified by column chromatography on silica gel (90:10 petroleum ether/EtOAc) to obtain desired product (4.53 g, 87.4%). $^1$H NMR (300 MHz, CDCl$_3$) δ 5.38 (1H, s), 4.60 (1H, m), 4.18 (1H, s), 3.50-3.20 (6H, m), 3.00 (1H, m), 2.80 (1H, m), 2.40 (4H, m), 1.80 (4H, m), 1.40 (9H, m). MS m/z 374 (MH$^+$).

Step 9

To a solution of the product of Step 8 (2 g, 0.06 mmol) in MeOH was added excess ammonium formate and 10% Pd/C. The reaction mixture was heated under reflux overnight. After filtering, the solution was evaporated and residue was purified on silica gel (10% MeOH/chloroform) to obtain the title product (800 mg). $^1$H NMR (300 MHz, CDCl$_3$) δ 5.25 (1H,s), 4.7 (1H, m), 3.45 (1H, m), 3.25 (1H, m), 3.04 (m) 2.9 (1H, m), 2.5 (6H, m), 1.80 (4H, m), 1.45 (9H, s). MS m/z 284 (MH$^+$).

Preparation 5 tert-butyl (3S,4S)-4-(2-Oxopyrrolidin-1-yl)pyrrolidin-3-ylcarbamate

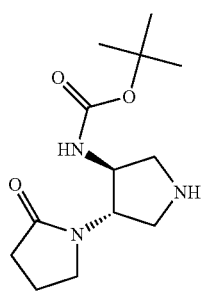

Step 1: tert-butyl (3S,4S)-4-(4-Chlorobutanamido)-1-benzylpyrrolidin-3-ylcarbamate To a solution of the product of Step 6, Preparation 4 (2.00 g, 6.86 mmol) and TEA (0.76 g, 7.55 mmol) in dichloromethane (50 mL) was added 4-chlorobutyrylchloride (1.02 g, 7.21 mmol) dropwise. After about 16 hours, aqueous sodium bicarbonate was added. The mixture was extracted with dichloromethane, dried over magnesium sulfate, filtered, and concentrated to give a white solid (2.41 g) that was sufficiently pure for further use. MS m/z 396 and 398 (MH$^+$).

Step 2: tert-butyl (3S,4S)-1-Benzyl-4-(2-oxopyrrolidin-1-yl)pyrrolidin-3-ylcarbamate To a solution of the product of Step 2 (2.41 g, 6.08 mmol) in THF (10 mL) and DMF (5 mL) was added sodium hydride (0.27 g, 60% in mineral oil, 6.69 mmol). After about 16 hours, the reaction was quenched with water and extracted with EtOAc. The combined organic layers were washed with 4% magnesium sulfate solution and brine, dried over magnesium sulfate, filtered, and concentrated to furnish the 2.12 g of the product as an off-white solid.

Step 3

To a solution of the product of Step 3 (2.0 g, 5.56 mmol) in MeOH (30 mL) was added palladium hydroxide (0.5 g). The mixture was hydrogenated at 30 to 50 psi for about 18 hours. The solution was filtered over diatomaceous earth and the filtrate was evaporated to give 1.5 g of the title compound as a glassy solid. MS m/z 270 (MH$^+$).

Preparation 6 tert-butyl (3S,4S)-1-(6-Chloropyrimidin-4-yl)-4-(2-oxopyrrolidin-1-yl)pyrrolidin-3-ylcarbamate

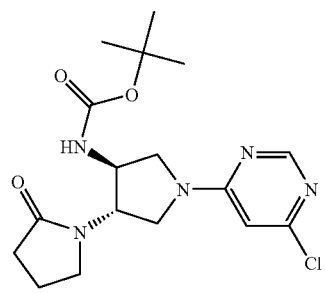

The title compound of Preparation 5 (905.3 mg, 3.4 mmol, 1 eq), 2,4-dichloropyrimidine (550.8 mg, 3.7 mmol, 1.1 eq) and DIPEA (1484.0 mg, 2.0 mL, 11.5 mmol, 3.4 eq) in 4 mL of EtOH were added to a 5 mL microwave vial and microwave heated for 5 minutes at 155° C. The solvent was evaporated and the residue was purified by chromatography (Biotage 25M (A Dynax Corp.; Charlottesville, Va.) eluting with 150 mL each of 50% petroleum ether/EtOAc and 0, 1, 3, and 5% MeOH/EtOAc) to afford 926.3 mg, (72.2%) yield of the product. MS 382.3 (AP$^+$, 100).

Preparation 7

6-((3S,4S)-3-(tert-butoxycarbonyl)-4-(2-oxopiperidin-1-yl)pyrrolidin-1-yl)pyrimidine-4-carboxylic acid

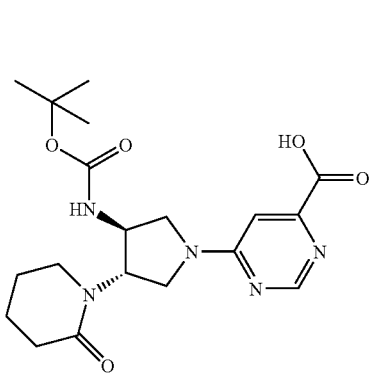

Step 1: Methyl 4-((3S,4S)-3-(tert-butoxycarbonyl)-4-(2-oxopiperidin-1-yl)pyrrolidin-1-yl)-6-chloro-1,3,5-triazine-2-carboxylate A solution of the title compound from Preparation 1 (300 mg, 1.0 mmol) and DIPEA (194 mL, 1.11 mmol) in DMF (4.0 mL) was cooled to −78° C. prior to the addition of a solution of methyl 2,6-dichloropyrimidine-4-carboxylate (197 mg, 1.11 mmol) in DMF (1.0 mL). The reaction was allowed to gradually warm to RT and stirred for 16 hours. The reaction mixture was partitioned between EtOAc (50 mL) and H$_2$O (30 mL), the organic layer washed with saturated NaCl solution (3×30 mL), dried over sodium sulfate, filtered, and concentrated to provide 410 mg (85%) of the product. MS 454.2 (AP$^+$, 100).

Step 2

The product from Step 1 (410 mg, 0.90 mmol) was dissolved in THF (10.0 mL) and 10% palladium on activated charcoal (96 mg) was added followed by 0.18 M sodium hydroxide (5.0 mL). This mixture was hydrogenated at 50 psi for 16 hours. The reaction was filtered through diatomaceous earth and the solids were washed with MeOH. The filtrate was concentrated and the residue was partitioned between diethyl ether (20 mL) and H$_2$O (20 mL). The aqueous layer was acidified with acetic acid, extracted with EtOAc (2×50 mL) and then with a 3:1 mixture of chloroform/isopropanol (3×50 mL). The combined organic extracts were dried over sodium sulfate, filtered, and concentrated to provide 207 mg (56%) of the product as a white solid. MS 406.3 (AP$^+$, 100).

EXAMPLE 1

1-((3S,4S)-4-amino-1-(4-(3,3-difluoropyrrolidin-1-yl)-1,3,5-triazin-2-yl)pyrrolidin-3-yl)-5,5-difluoropiperidin-2-one

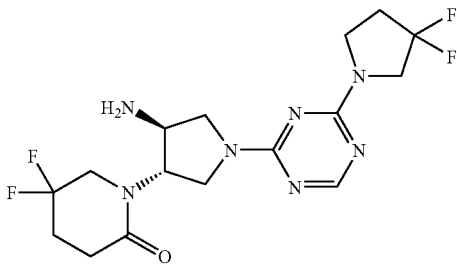

The compound 1-((3S,4S)-4-amino-1-(4-(3,3-difluoropyrrolidin-1-yl)-1,3,5-triazin-2-yl)pyrrolidin-3-yl)-5,5-difluoropiperidin-2-one, shown above, was prepared as follows.

Step 1

A solution of 2,4-dichloro-[1,3,5]triazine (30.0 g, 0.20 mol), 3,3-difluoropyrrolidine (28.7 g, 0.20 mol) and DIPEA (54.3 g, 0.42 mol) in 1,4-dioxane (300 mL) was heated at 50° C. for 1 hour. The reaction was cooled to room temperature, diluted with EtOAc and washed with water and then saturated sodium chloride solution. The organic phase was collected, dried over sodium sulfate and concentrated. The residue was purified by silica gel chromatography (20% EtOAc/heptane to 50% EtOAc/heptane) to afford 36.3 g (82%) of the product as a white solid. MS m/z 221.2 (AP$^+$100).

Step 2

A solution of the title compound from Preparation 2 (1.30 g, 4.08 mmol), the product from Step 1 (0.90 g, 4.08 mmol) and di-isopropylethylamine (1.05 g, 8.16 mmol) in tert-butyl alcohol (20.0 mL) was heated at 130° C. for in a sealed tube apparatus for 16 hours.

The reaction was cooled to room temperature and partitioned between EtOAc and H$_2$O. The organic layer washed with saturated sodium chloride solution, dried over sodium sulfate and concentrated to provide 2.05 g (99%) of the product as a white solid.

Step 3

The product from Example 2, Step 2 was dissolved in dichloromethane (30.0 mL) and trifluoroacetic acid (15.0 mL) was added. After stirring at room temperature for 1 hour, the reaction was concentrated and the residue was partitioned between EtOAc and 2.0 N sodium hydroxide solution. The organic phase washed with saturated sodium chloride solution, dried over sodium sulfate and concentrated to a white solid. This solid was suspended in EtOAc and heated to 80° C. and cooled to room temperature slowly. The resultant precipitate was collected to afford 0.84 g (51%) of the title compound as a white solid. (400 MHz, Methanol-d$_4$) δ 8.1 (br s, 1H), 4.84-4.74 (m, 1H), 4.07-3.96 (m, 1H), 3.92-3.66 (m, 7H), 3.65-3.54 (m, 1H), 3.47-3.36 (m, 1H), 3.20-3.10 (m, 1H), 2.75-2.22 (m, 6H). MS m/z 404.2 (AP$^+$100). DPP-IV IC$_{50}$=24.1 nM (n=24).

EXAMPLE 2

1-((3S,4S)-4-amino-1-(6-(3,3-difluoropyrrolidin-1-yl)pyrimidin-4-yl)pyrrolidin-3-yl)-5,5-difluoropiperidin-2-one

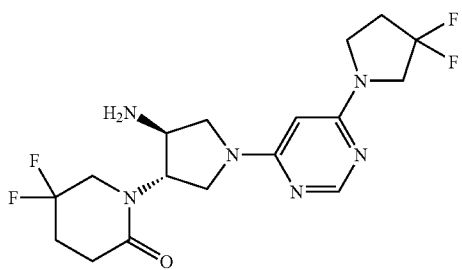

Step 1

A solution of 3,3-difluoropyrrolidine (215 mg, 1.5 mmol), 4,6-dichloro-pyrimidine (223 mg, 1.5 mmol) and DIPEA (194 mg, 1.5 mmol) in 1,4-dioxane (3.0 mL) was heated at 100° C. for 16 hours. The reaction was cooled to room temperature and then partitioned between EtOAc and water. The organic phase was separated and washed with saturated sodium chloride solution, dried over sodium sulfate and concentrated. The residue was separated with flash chromatography (25+S Biotage, 20% EtOAc/pentane) to afford 160 mg (48.6%) of 4-chloro-6-(3,3-difluoropyrrolidin-1-yl)pyrimidine as a solid.

Step 2

A solution of the compound from Preparation 2 (160 mg, 0.501 mmol), the product from Example 4, Step 1 (110 mg, 0.501 mmol) and DIPEA (130 mg, 1.00 mmol) in tert-butyl alcohol (3.0 mL) was heated at 145° C. for 1 hour in a Biotage Personal Chemistry Microwave Oven. The reaction was cooled to room temperature and then partitioned between EtOAc and water. The organic phase was separated and washed with saturated sodium chloride solution, dried over sodium sulfate and concentrated to an oil. A solution of this oil (252 mg, 0.501 mmol) in dichloromethane (1.0 mL) and trifluoroacetic acid (1.0 mL) was stirred at room temperature for 1 hour. The reaction was concentrated and separated by chromatography (25+S Biotage, dichloromethane/methanol/ammonium hydroxide: 95:5:0.5), affording 86 mg (43%) of the title compound as a white solid. (400 MHz, Methanol-d$_4$) δ 8.02 (s, 1H), 5.31 (s, 1H), 4.95-4.82 (m, 1H), 4.00-3.60 (m, 9H), 3.36 (t, 1H), 3.11 (t, H), 2.70-2.20(m, 6H). MS m/z 403.3 (AP$^+$100). DPP-IV IC$_{50}$=8.39 nM (n=4).

EXAMPLE 3

1-((3S,4S)-4-amino-1-(6-(3,3-difluoropyrrolidin-1-yl)-2-methylpyrimidin-4-yl)pyrrolidin-3-yl)-5,5-difluoropiperidin-2-one

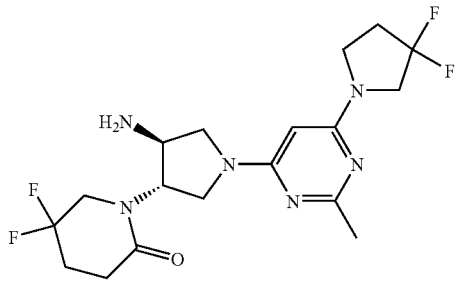

The compound 1-((3S,4S)-4-amino-1-(6-(3,3-difluoropyrrolidin-1-yl)-2-methylpyrimidin-4-yl)pyrrolidin-3-yl)-5,5-difluoropiperidin-2-one, shown above, was prepared as follows.

Step 1

A solution of 3,3-difluoropyrrolidine (0.50 g, 3.48 mmol), 2-methyl-4,6-dichloropyrimidine (0.568 g, 3.48 mmol) and di-isopropylethylamine (0.90 mg, 6.97 mmol) in 1,4-dioxane was at 100° C. for 16 hours. The reaction was cooled to room temperature, partitioned between ethyl acetate ("EtOAc") and water and the organic phase washed with saturated sodium chloride, dried over sodium sulfate and concentrated. The residue was separated by chromatography (25+S Biotage, EtOAc/heptane gradient: 20% to 50%) 5-(6-chloro-2-methylpyrimidin-4-yl)-4,5,6,7-tetrahydroisoxazolo[4,3-c]pyridine as an oil.

Step 2

A solution of the title compound from Preparation 1 (150 mg, 0.470 mmol), the product from Example 1, Step 1 (110 mg, 0.470 mmol) and N,N-diisopropylethylamine (DIPEA) (121 mg, 0.939 mmol) in tert-butyl alcohol (2.0 mL) was heated at 145° C. for 1 hour in a Biotage Personal Chemistry Microwave Oven. The reaction was cooled to room temperature, partitioned between EtOAc and water and the organic phase washed with saturated sodium chloride, dried over sodium sulfate and concentrated to an oil. The oil was dissolved in dichloromethane (2.0 mL), trifluoroacetic acid (1.0 mL) was then added to the solution and then the solution was stirred at room temperature for 1 hour. The solvents were removed and the residue was separated by HPLC (Shimadzu preparative HLPC; Gemini 5u AXIA 30×50 mm C18 Phenomenex column; 60 ml/min flow rate; 210 nm UV detector; 5% to 60% gradient eluting with acetonitrile/water modified with 0.1% trifluoroacetic acid). The desired fractions were concentrated and the residue was dissolved in saturated sodium carbonate solution and extracted with dichloromethane (2×). The combined organic extracts were dried over sodium sulfate and concentrated to afford 56 mg (29%) of the title compound as a white solid. (400 MHz, Methanol-d$_4$) δ 5.15 (s, 1H), 4.90-4.80 (m, 1H), 3.94-3.62 (m, 9H), 3.36 (t, J=8.3 Hz, 1H), 3.10 (t, 1H), 2.72-2.20 (m, 6H), 2.31 (s, 3H). MS 417.3 (AP$^+$100). DPP-IV IC$_{50}$=12.6 nM (n=4).

EXAMPLE 4

1-((3S,4S)-4-amino-1-(6-(6,7-dihydroisoxazolo[4,3-c]pyridin-5(4H)-yl)pyrimidin-4-yl)pyrrolidin-3-yl)-5,5-difluoropiperidin-2-one

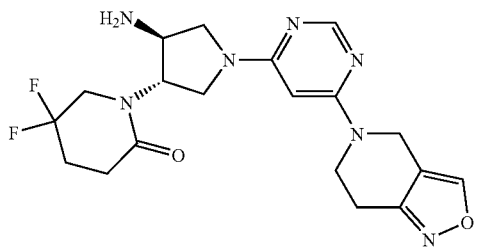

The compound 1-((3S,4S)-4-amino-1-(6-(6,7-dihydroisoxazolo[4,3-c]pyridin-5(4H)-yl)pyrimidin-4-yl)pyrrolidin-3-yl)-5,5-difluoropiperidin-2-one, shown above, was prepared as follows.

Step 1

4,5,6,7-Tetrahydro-isoxazolo[4,3-c]pyridine (162 mg, 1.3 mmol), 2,4-dichloropyrimidine (214 mg, 1.4 mmol), and DIPEA (422 mg, 0.57 mL, 3.3 mmol) in 3 mL of ethanol were added to a 5 mL microwave vial and microwave heated for 5 minutes at 150° C. The solvent was evaporated and the residue purified by chromatography (Biotage 25 S eluting with 100 mL each of 0, 10, 20, 30, and 40% tetrahydrofuran ("THF")/petroleum ether) to afford 215 mg, (69.7% yield) of the product. MS 237.2 (AP+, 100).

Step 2

A solution of the compound from Preparation 2 (97 mg, 0.304 mmol), the product from Example 3, Step 1 (72 mg, 0.304 mmol) and DIPEA (79 mg, 0.608 mol) in tert-butyl alcohol (3.0 mL) was heated at 145° C. for 3 hours in a Biotage Personal Chemistry Microwave Oven. The reaction was partitioned between EtOAc and water and the organic phase washed with saturated sodium chloride solution, dried over sodium sulfate and concentrated to an oil. The oil was dissolved in dichloromethane (2.0 mL), trifluoroacetic acid (1.0 mL) was added and the solution was stirred at room temperature for 1 hour. The solvents were removed and the residue was separated by HPLC (Shimadzu preparative HLPC; Gemini 5u AXIA 30×50 mm C18 Phenomenex column; 60 ml/min flow rate; 210 nm UV detector; 5% to 60% gradient eluting with acetonitrile/water modified with 0.1% trifluoroacetic acid). The desired fractions were concentrated and the residue was dissolved in saturated sodium carbonate solution and extracted with dichloromethane (2×). The combined organic extracts were dried over sodium sulfate and concentrated to afford 52 mg (41%) of the title compound as a white solid. (400 MHz, Methanol-$d_4$) δ 8.47 (s, 1H), 8.07 (s, 1H), 5.66 (s, 1H), 4.95-4.82 (m, 1H), 4.72-4.66 (m, 2H), 4.05-3.80 (m, 3H), 3.79-3.60 (m, 4H), 3.42-3.27 (m, 1H), 3.18-3.08 (m, 1H), 2.89 (t, 2H), 2.75-2.20 (m, 6H). MS 420.3 (ES+).). DPP-IV $IC_{50}$=6.08 nM (n=4)

EXAMPLE 5

1-((3S,4S)-4-Amino-1-(6-(6,7-dihydroisoxazolo[4,3-c]pyridin-5(4H)-yl)pyrimidin-4-yl)pyrrolidin-3-yl) piperidin-2-one dihydrochloride

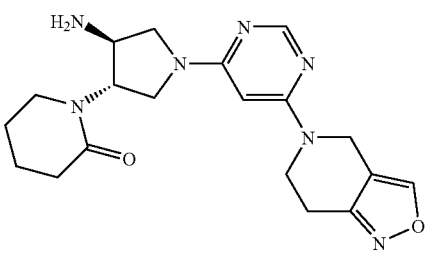

Step 1: 5-(6-Chloro-pyrimidin-4-yl)-4,5,6,7-tetrahydro-isoxazolo[4,3-c]pyridine 4,5,6,7-Tetrahydro-isoxazolo[4,3-c]pyridine (162.0 mg, 1.3 mmol), 2,4-dichloropyrimidine (213.9 mg, 1.4 mmol), and DIPEA (421.6 mg, 0.57 mL, 3.3 mmol) in 3 mL of EtOH were added to a 5 mL microwave vial and microwave heated for 5 minutes at 150° C. The solvent was evaporated and the residue purified by chromatography (Biotage 25 S eluting with 100 mL each of 0, 10, 20, 30, and 40% THF/petroleum ether) to afford 215.3 mg, (69.7% yield) of the product. MS 237.2 (AP+, 100).

Step 2: [(3S,4S)-1-[6-(6,7-Dihydro-4H-isoxazolo[4,3-c]pyridin-5-yl)-pyrimidin-4-yl]-4-(2-oxo-piperidin-1-yl)-pyrrolidin-3-yl]-carbamic acid tert-butyl ester The title compound of Preparation 4 (48.6 mg, 0.25 mmol), the product of Step 1 (59.2 mg, 0.25 mmol), and DIPEA (371.0 mg, 500.0 ul, 2.9 mmol) in 1 mL of EtOH were added to a 5 mL microwave vial and microwave heated for one hour at 155° C. The solvent was evaporated and the residue was purified by chromatography (Biotage 25 S eluting with 100 mL each of 0, 3, 8, 12, and 15% MeOH/EtOAc) to afford 46.4 mg, (38.4% yield) of the product.

Step 3

The product of Step 2 (46.4 mg, 0.1 mmol) and 3 mL of 4 M HCl/dioxane were stirred at RT for 17 hours. The solvent was evaporated to afford 43.7 mg, (99.8% yield) of the title compound as the HCl salt. MS 384.3 (AP+, 100). DPP-IV $IC_{50}$=11.8 nM (n=4)

EXAMPLE 6

1-((3S,4S)-4-Amino-1-(6-phenylpyrimidin-4-yl) pyrrolidin-3-yl)pyrrolidin-2-one dihydrochloride

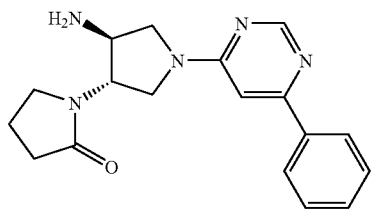

Step 1: 4-Chloro-6-phenylpyrimidine

Phenylboronic acid (3.05 g, 25 mmol) was added to a solution of 4,6-dichloropyrimidine (7.45 g, 50 mmol) in 50 mL of dimethoxyethane at 70° C. followed by cesium fluoride (7.60 g, 50.0 mmol). The resulting mixture was stirred for 5 minutes at 80° C. and [1,1'-bis(diphenylphosphino)ferrocene]dichloropalladium (II) (2.04 g, 2.5 mmol) was then added. The reaction mixture was stirred at 80° C. for one hour then evaporated. The residue was extract with ether (3×50 mL) and EtOAc (1×50 mL). The combined organic layers were washed with 100 mL saturated sodium carbonate solution (100 mL), dried over magnesium sulfate, filtered, and concentrated. The residue was purified by chromatography (Biotage 40 L eluting with 250 mL each of 0, 10, 20, 30, 40, 50, 60, 70, 80, and 100% dichloromethane/petroleum ether) to afford 2.20 g, (46.2%) of the product. MS 191.0 (AP$^+$, 100).

Step 2: tert-butyl (3S,4S)-4-(2-Oxopyrrolidin-1-yl)-1-(6-phenylpyrimidin-4-yl)pyrrolidin-3-ylcarbamate The title compound of Preparation 5 (69.0 mg, 0.25 mmol), the product from Step 1 (48.8 mg, 0.25 mmol), and DIPEA (49.6 mg, 67.0 ul, 0.38 mmol) in 5 mL of dimethoxyethane were added to a 5 mL microwave vial and microwave heated for 25 minutes at 150° C. The solvent was evaporated and the residue was purified by chromatography (Biotage 25 S eluting with 100 mL each of 0, 20, 60, and 67% THF/petroleum ether) to afford 81.3 mg (74.9%) yield of pure product. LC-MS 424.0 (ES$^+$, 100).

Step 3

The product from Step 2 (81.3 mg, 0.19 mmol) and 4 mL of 4 M HCl/dioxane were stirred at RT for 5 hours. The solvent was evaporated and the solid triturated with ether to afford 67.0 mg, (97%) yield of the title product. MS 324.3 (AP$^+$, 100). DPP-IV IC$_{50}$=488 nM (n=4)

EXAMPLE 7

1-((3S,4S)-4-Amino-1-(6-phenylpyrimidin-4-yl) pyrrolidin-3-yl)piperidin-2-one hydrochloride

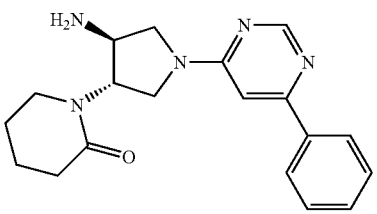

The title compound was prepared in a manner analogous to Example 7 using the title compound of Preparation 4 and the product of Step 1, Example 7. MS 338.3 (MH$^+$) DPP-IV IC$_{50}$=47.4 nM (n=4).

EXAMPLE 8

1-{(3S,4S)-4-Amino-1-[6-(6-hydroxy-pyridin-3-yl) pyrimidin-4-yl]-pyrrolidin-3-yl}-piperidin-2-one

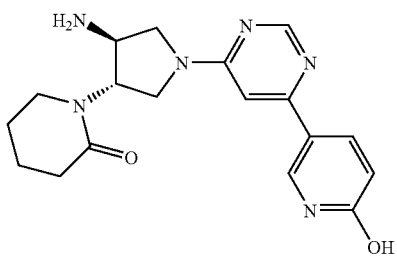

Step 1

A 5 ml microwave vial was charged with the title compound of Preparation 4 (56.7 mg, 0.2 mmol), 4-chloro-6-(6-methoxypyridin-3-yl)-pyrimidine (44.3 mg, 0.2 mmol), DIPEA (0.6 mmol), and 3.0 ml of anhydrous EtOH. The mixture was heated at 150° C. for 1.5 hours in a Biotage Personal Chemistry Microwave Oven. The solvent was evaporated and the residue was purified by chromatography (Biotage Flash 25S, 8% MeOH/EtOAc) to afford 74.6 mg (80% yield) of a solid. MS m/z 469.4 (MH$^+$).

Step 2

The product of Step 1 (74.6 mg, 0.16 mmol) was treated with TFA (3.0 ml, 50% (v/v) in dichloromethane). The solvent was removed and the residue triturated with toluene, followed by dichloromethane and petroleum ether, to afford 92.0 mg (96% yield) of a white solid. MS m/z 369.4 (MH$^+$).

Step 3

The product of Step 2 (50.0 mg, 0.1 mmol) and 4 ml of 4N HCl/dioxane were stirred at 75° C. for 10 minutes, and then at RT overnight. The solvent was removed, the residue dissolved in 1.5 ml of MeOH, and the solution purified by HPLC (Shimadzu preparative HLPC; reverse-phase $C_{18}$ 50×50 Waters XTerra® column; 60 ml/min flow rate; 210 nm UV detector; 2% to 50% gradient eluting with acetonitrile/water modified with 0.1% ammonium hydroxide) to afford 29.5 mg of the title compound as a white solid. MS m/z 355.3 (MH$^+$). DPP-IV $IC_{50}$=27.1 nM (n=4).

EXAMPLE 9

1-((3S,4S)-4-amino-1-(6-(6-methoxypyridin-3-yl)pyrimidin-4-yl)pyrrolidin-3-yl)-5,5-difluoropiperidin-2-one trifluoroacetate

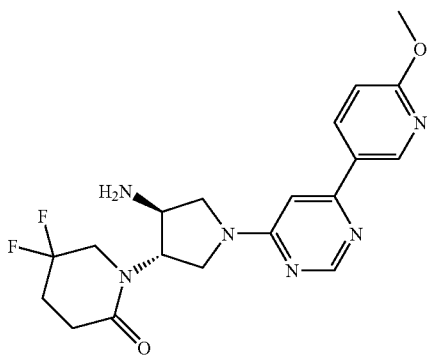

The compound 1-((3S,4S)-4-amino-1-(6-(6-methoxypyridin-3-yl)pyrimidin-4-yl)pyrrolidin-3-yl)-5,5-difluoropiperidin-2-one trifluoroacetate, shown above, was prepared as follows.

Step 1

To a solution of 6-methoxypyridin-3-ylboronic acid (0.48 g, 2.48 mmol), 4,6-dichloropyrimidine (1.11 g, 7.43 mmol) and tetrakis(triphenylphosphine)palladium (0.29 g, 0.248 mmol) in toluene (38 mL) was added a saturated solution of potassium carbonate (8.0 mL) and the mixture was heated at 100° C. for 16 hours. The mixture was cooled to room temperature and partitioned between EtOAc and water. The organic phase washed with saturated sodium chloride solution, dried and concentrated. The residue was separated by chromatography (40S Biotage, EtOAc/hexanes: 1:49) to provide 0.25 g (53%) of the biaryl coupled product. MS m/z 222.2 (AP$^+$100).

Step 2

A solution of the product from Step 1 (23.3 mg, 0.105 mml), the product from Preparation 2 (33.5 mg, 0.105 mmol) and di-isopropylethylamine (27.1 mg, 0.210 mmol) in tert-butyl alcohol (0.42 mL) was placed in a 1 dram screw-cap vial and heated to 100° C. with agitation. After 2 hours the reaction mixture was directly injected onto a 5 gm ISCO Solid Sample Cartidge and separated on an ISCO Companion flash chromatography system (4 gm silica column, 5-20% ethanol-heptane) to provide 37 mg (70%) of the product as an off-white solid.

Step 3

The product from Step 2 was dissolved in a 1:1 dichloromethane/trifluoroacetic acid mixture (1 mL) and the solution was agitated at room temperature for 60 minutes. After 1 hour the mixture was concentrated and the residue was triturated with di-isopropylether and decanted. The collected solid was dried to constant weight to afford 38 mg (99%) of the title compound as an off-white solid. (400 MHz, Methanol-d$_4$) δ 8.73 (d, 1H), 8.68 (s, 1H), 8.19 (dd, 1H), 7.05 (s, 1H), 6.95 (d, 1H), 5.28-5.13 (m, 1H), 4.42-4.01 (m, 3H), 3.97 (s, 3H), 3.86-3.59 (m, 4H), 2.68-2.58 (m, 2H), 2.44-2.29 (m, 2H). DPP-IV $IC_{50}$=27.3 nM (n=4).

EXAMPLES 10-87

The compounds of following examples were prepared using the appropriate amine analogs and a method of Examples 1-9. Alternately, the following method such as was used to prepare the compounds such as those of Examples 45, 49, 53-54 and 56-57

Step 1

The appropriation preparation compound (0.10 mmol, 38.2 mg) was charged into a 5 mL microwave vial. A solution of an appropriately-substituted amine (0.175 mmol) dissolved in one mL of EtOH was then added to the vial, followed by DIPEA (1 mmol, 0.15 mL), and 5 mg of DMAP. The vial was heated on a Personal Chemistry Microwave station (Biotage) for 4,000 seconds at 160° C. After complete reaction, the reaction mixture was transferred to a two dram vial and the solvent was evaporated on a GENEVAC (Genevac Ltd.; Ipswich, England). The residue was purified on a Shimadzu preparative HPLC (Shimadzu Corp.; Kyoto, Japan) (gradient 0 to 50% water/acetonitrile, modified with 0.1% ammonium hydroxide, using a Waters XTerra® 50×50 column (Waters Instrument Co.; Milford, Mass.), at a flow rate of 75 mL/min and monitoring wavelength 220 nm); or chromatography (Biotage 25S) with gradient of 100 ml each of 0, 3, 6, 9, and 15% MeOH/EtOAc).

Step 2

The product from Step 1 in a 2 dram vial was dissolved in 2 mL of 4 M HCl/dioxane and shaken at RT for 17 hours. Solvent evaporation afforded the product as an HCl salt.

In Example 27, the solvent was removed from the final deprotection step and the salt was re-crystallized directly from a suitable solvent such as diethyl ether.

| Ex. | Compound Name and ¹H NMR (Methanol-d₄) δ | n | R¹ | Q | NRᴬRᴮ | R⁴¹ | DPP-IV IC₅₀ (nM) or Percent Inhibition at 300 nM (n-value) |
|---|---|---|---|---|---|---|---|
| 10 | 1-((3S,4S)-4-Amino-1-(6-(3,3-difluoropyrrolidin-1-yl)pyrimidin-4-yl)pyrrolidin-3-yl)piperidin-2-one dihydrochloride ¹H NMR(D₂O, 400 MHz) δ 8.03(s, 1H), 5.26(s, 1H), 5.10(s, 1H), 4.14(m, 1H), 4.03(m, 1H), 3.79(m, 3H), 3.40-3.70(m, 4H), 3.21(m, 2H), 2.43(m, 2H), 2.27(m, 2H), 1.50-1.70(m, 4H) | 2 | H | CH | 3,3-difluoropyrrolidinyl | H | 25.5 (4) |
| 11 | 1-{(3S,4S)-4-Amino-1-[4-(3,3-difluoro-pyrrolidin-1-yl)-[1,3,5]triazin-2-yl]-pyrrolidin-3-yl}-piperidin-2-one dihydrochloride ¹H NMR(D₂O, 400 MHz) δ 8.03(d, 1H, J=8.31Hz), 5.01(m, 1H), 4.15(m, 2H), 3.91(m, 3H), 3.40-4.00 (m, 4H), 3.23(m, 2H), 2.33-2.55(m, 2H), 2.28(m, 2H), 1.55-1.75(m, 4H) | 2 | H | N | 3,3-difluoropyrrolidinyl | H | 37.4 (4) |
| 12 | 1-((3S,4S)-4-Amino-1-(6-(3,3-difluoropyrrolidin-1-yl)pyrimidin-4-yl)pyrrolidin-3-yl)pyrrolidin-2-one dihydrochloride ¹H NMR(D₂O, 400 MHz) δ 8.04(s, 1H), 5.28(s, 1H), 4.76(m, 1H), 3.94-4.14(m, 2H), 3.79(m, 3H), 3.46-3.68(m, 4H), 3.6 (t, J=7.1Hz, 2H), 2.43 (m, 2H), 2.31(m, 2H), 1.93(m, 2H) | 1 | H | CH | 3,3-difluoropyrrolidinyl | H | 522 (4) |
| 13 | 1-((3S,4S)-4-amino-1-(6-(3,3-difluoropyrrolidin-1-yl)-2-(trifluoromethyl)pyrimidin-4-yl)pyrrolidin-3-yl)-5,5-difluoropiperidin-2-one | 2 | F | CH | 3,3-difluoropyrrolidinyl | CF₃ | 56.7 (4) |

-continued

| Ex. | Compound Name and $^1$H NMR (Methanol-$d_4$) δ | n | $R^1$ | Q | $NR^AR^B$ | $R^{41}$ | DPP-IV IC$_{50}$ (nM) or Percent Inhibition at 300 nM (n-value) |
|---|---|---|---|---|---|---|---|
| 14 | 1-((3S,4S)-4-amino-1-(6-(3,3-difluoropyrrolidin-1-yl)-2-(trifluoromethyl)pyrimidin-4-yl)pyrrolidin-3-yl)piperidin-2-one | 2 | H | CH | 3,3-difluoropyrrolidin-1-yl | $CF_3$ | 45.1 (4) |
| 15 | 1-((3S,4S)-4-amino-1-(6-(3,3-difluoropyrrolidin-1-yl)-2-ethylpyrimidin-4-yl)pyrrolidin-3-yl)piperidin-2-one (400MHz, Methanol-$d_4$) δ 5.15(s, 1H), 4.94-4.82(m, 1H), 3.94-3.62(m, 6H), 3.45-3.32(m, 3H) 3.16-3.06(m, 1H), 2.58(q, 2H), 2.54-2.44(m, 4H), 1.96-1.73(m, 4H), 1.24(s, 3H). | 2 | H | CH | 3,3-difluoropyrrolidin-1-yl | $(CH_2)_2$ | 39.8 (4) |
| 16 | 1-((3S,4S)-4-amino-1-(6-(3,3-difluoropyrrolidin-1-yl)-2-isopropylpyrimidin-4-yl)pyrrolidin-3-yl)piperidin-2-one formate (400MHz, Methanol-$d_4$) δ 5.32(1H, s), 5.12(1H, m), 4.18(2H, c), 3.92-3.82(2H, c), 3.73(2H, m), 3.64(1H, m), 3.54(1H, c), 3.37(2H, c), 2.97(1H, m), 2.52(2H, c), 2.41(2H, c), 1.83(4H, c), 1.24(6H, d). | 2 | H | CH | 3,3-difluoropyrrolidin-1-yl | $CH(CH_3)_2$ | 136 (4) |
| 17 | 1-((3S,4S)-4-amino-1-(2-cyclopropyl-6-(3,3-difluoropyrrolidin-1-yl)pyrimidin-4-yl)pyrrolidin-3-yl)piperidin-2-one (400MHz, Methanol-$d_4$) δ 5.10(s, 1H), 4.91-4.82(m, 1H), 3.83-3.56(m, 7H), 3.44-3.31(m, 3H), 3.14-3.03(m, 1H), 2.54-2.33(m, 4H), 1.97-1.74(m, 4H), 1.32-1.24(m, 1H), 1.04-0.96(2H), 0.82(dd, 2H). | 2 | H | CH | 3,3-difluoropyrrolidin-1-yl | cyclopropyl | 109 (4) |

-continued

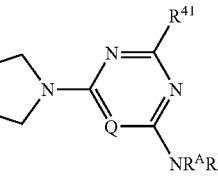

| Ex. | Compound Name and $^1$H NMR (Methanol-$d_4$) δ | n | $R^1$ | Q | $NR^AR^B$ | $R^{41}$ | DPP-IV IC$_{50}$ (nM) or Percent Inhibition at 300 nM (n-value) |
|---|---|---|---|---|---|---|---|
| 18 | 1-((3S,4S)-4-amino-1-(6-(3,3-difluoropyrrolidin-1-yl)-2-propylpyrimidin-4-yl)pyrrolidin-3-yl)piperidin-2-one formate (400MHz, Methanol-$d_4$) δ δ 5.32(1H, s), 5.12(1H, m), 4.19 (2H, c), 3.88(3H, t and c), 3.72(2H, m), 3.68 (1H, m), 3.53(1H, c), 3.36(2H, m), 2.66 (2H, m), 2.52(2H, m), 2.42(2H, m), 1.86 (3H, c), 1.78(3H, m), 0.97(3H, t). | 2 | H | CH | 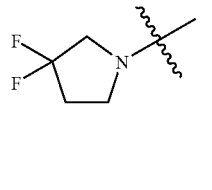 | $(CH_2)_2CH_3$ | 43.3 (4) |
| 19 | 1-((3S,4S)-4-amino-1-(6-(3,3-difluoropyrrolidin-1-yl)-2-(methylthio)pyrimidin-4-yl)pyrrolidin-3-yl)piperidin-2-one (400MHz, Methanol-$d_4$) δ 5.03(s, 1H), 4.96-4.79(m, 1H), 3.84-3.57(m, 5H), 3.44-3.30(m, 3H), 3.16-3.05(m, 1H), 2.54-2.32(m, 3H), 2.44(s, 3H), 1.97-1.74 (m, 4H) | 2 | H | CH | 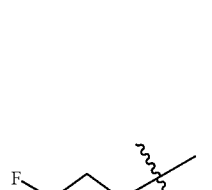 | $SCH_3$ | 74.9 (4) |
| 20 | 1-((3S,4S)-4-amino-1-(6-(3,3-difluoropyrrolidin-1-yl)-2-(ethylthio)pyrimidin-4-yl)pyrrolidin-3-yl)piperidin-2-one | 2 | H | CH | 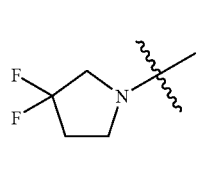 | $SCH_2CH_3$ | 82.5 (4) |
| 21 | 1-((3S,4S)-4-amino-1-(6-(3,3-difluoropyrrolidin-1-yl)-5-fluoropyrimidin-4-yl)pyrrolidin-3-yl)piperidin-2-one (400MHz, Methanol-$d_4$) δ 7.84(1H, d), 4.9 (1H, m), 4.07(1H, m), 3.95(2H, m), 3.85 (3H, c), 3.76(1H, m), 3.66(1H, m), 3.44-3.34 (3H, c), 2.44(4H, c), 1.9(1H, c), 1.82 (3H, c). | 2 | H | CF | | H | 218 (4) |

-continued

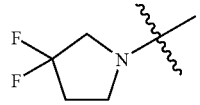

| Ex. | Compound Name and ¹H NMR (Methanol-d₄) δ | n | $R^1$ | Q | $NR^AR^B$ | $R^{41}$ | DPP-IV $IC_{50}$ (nM) or Percent Inhibition at 300 nM (n-value) |
|---|---|---|---|---|---|---|---|
| 22 | 1-((3S,4S)-4-amino-1-(2-tert-butyl-6-(3,3-difluoropyrrolidin-1-yl)pyrimidin-4-yl)pyrrolidin-3-yl)piperidin-2-one | 2 | H | CH | 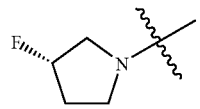 | t-butyl | 832 (4) |
| 23 | 1-((3S,4S)-4-amino-1-(6-((S)-3-fluoropyrrolidin-1-yl)pyrimidin-4-yl)pyrrolidin-3-yl)-5,5-difluoropiperidin-2-one 8.00(s, 1H), 5.35(d, 1H), 5.28(s, 1H), 4.94-4.80(m, 1H), 3.94-3.15(m, 10H), 3.12(t, 1H), 2.72-2.53(m, 2H), 2.48-2.03 (m, 4H) | 2 | F | CH | 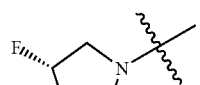 | H | 12 (4) |
| 24 | 1-((3S,4S)-4-amino-1-(4-((S)-3-fluoropyrrolidin-1-yl)-1,3,5-triazin-2-yl)pyrrolidin-3-yl)-5,5-difluoropiperidin-2-one 8.05(d, J=4.5Hz, 1H), 5.32(d, 1H), 4.89-4.75(m, 1H), 4.12-3.94(m, 1H), 3.95-3.36(m, 8H), 3.23-3.07(m, 2H), 2.73-2.53(m, 2H), 2.50-2.00(m, 4H) | 2 | F | N | 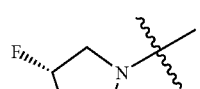 | H | 47.8 (4) |
| 25 | 1-((3S,4S)-4-Amino-1-(4-((S)-3-fluoropyrrolidin-1-yl)-1,3,5-triazin-2-yl)pyrrolidin-3-yl)piperidin-2-one trifluoroacetate MS(M+1) 350.2 | 2 | H | N | 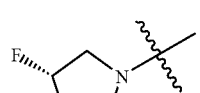 | H | 80.2 (4) |
| 26 | 1-((3S,4S)-4-amino-1-(6-((S)-3-fluoropyrrolidin-1-yl)-2-methylpyrimidin-4-yl)pyrrolidin-3-yl)-5,5-difluoropiperidin-2-one 5.33(d, 1H), 5.13(s, 1H), 4.89-4.78(m, 1H), 3.94-3.31(m, 10H), 3.10(dd, 1H), 2.72-2.53(m, 2H), 2.48-2.03(m, 4H), 2.31(s, 3H) | 2 | F | CH | | $CH_3$ | 37.3 (4) |

-continued

| Ex. | Compound Name and $^1$H NMR (Methanol-d$_4$) δ | n | R$^1$ | Q | NR$^A$R$^B$ | R$^{41}$ | DPP-IV IC$_{50}$ (nM) or Percent Inhibition at 300 nM (n-value) |
|---|---|---|---|---|---|---|---|
| 27 | 1-((3S,4S)-4-Amino-1-(4-((R)-3-fluoropyrrolidin-1-yl)-1,3,5-triazin-2-yl)pyrrolidin-3-yl)piperidin-2-one trifluoroacetate MS(M+1) 350.9 | 2 | H | N | (R)-3-fluoropyrrolidin-1-yl | H | 92.2 (4) |
| 28 | 1-((3S,4S)-4-Amino-1-(4-((3R,4S)-3,4-difluoropyrrolidin-1-yl)-1,3,5-triazin-2-yl)pyrrolidin-3-yl)piperidin-2-one trifluoroacetate MS(M+1) 368.2 | 2 | H | N | (3R,4S)-3,4-difluoropyrrolidin-1-yl | H | 67.8 (4) |
| 29 | 1-((3S,4S)-4-Amino-1-(4-((3R,4R)-3,4-difluoropyrrolidin-1-yl)-1,3,5-triazin-2-yl)pyrrolidin-3-yl)piperidin-2-one trifluoroacetate MS(M+1) 368.2 | 2 | H | N | (3R,4R)-3,4-difluoropyrrolidin-1-yl | H | 154 (4) |
| 30 | 1-((3S,4S)-4-Amino-1-(4-((3S,4S)-3,4-difluoropyrrolidin-1-yl)-1,3,5-triazin-2-yl)pyrrolidin-3-yl)piperidin-2-one trifluoroacetate MS(M+1) 368.2 | 2 | H | N | (3S,4S)-3,4-difluoropyrrolidin-1-yl | H | 104 (4) |
| 31 | 1-((3S,4S)-4-Amino-1-(6-(pyrrolidin-1-yl)pyrimidin-4-yl)pyrrolidin-3-yl)pyrrolidin-2-one (dihydrochloride) $^1$H NMR(D$_2$O, 400 MHz) δ 7.96(s, 1H), 5.21(s, 1H), 4.74(m, 1H), 4.01(m, 2H), 3.52(m, 3H), 3.31(m, 6H), 2.31(m, 2H), 1.89(m, 6H) | 1 | H | CH | pyrrolidin-1-yl | H | 483 (4) |
| 32 | 1-((3S,4S)-4-Amino-1-(4-(pyrrolidin-1-yl)-1,3,5-triazin-2-yl)pyrrolidin-3-yl)piperidin-2-one trifluoroacetate MS(M+1) 332.2 | 2 | H | N | pyrrolidin-1-yl | H | 91.5 (4) |

-continued

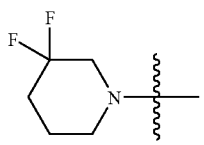

| Ex. | Compound Name and ¹H NMR (Methanol-d₄) δ | n | R¹ | Q | NR^A R^B | R^41 | DPP-IV IC$_{50}$ (nM) or Percent Inhibition at 300 nM (n-value) |
|---|---|---|---|---|---|---|---|
| 33 | 1-((3S,4S)-4-amino-1-(6-(3,3-difluoropiperidin-1-yl)-2-methylpyrimidin-4-yl)pyrrolidin-3-yl)-5,5-difluoropiperidin-2-one trifluoroacetate 5.77(s, 1H), 5.23-5.08 (m, 1H), 5.35-4.13(m, 2H), 4.12-4.03(m, 2H), 3.94(t, J=10.4Hz, 1H), 3.86-3.61(m, 6H), 2.75-2.61(m, 2H), 2.51(s, 3H), 2.48-2.24(m, 2H), 2.22-2.06(m, 2H), 1.95-1.1.75(m, 2H) | 2 | F | CH | 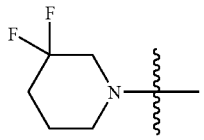 | CH₃ | 97.7 (4) |
| 34 | 1-((3S,4S)-4-amino-1-(6-(3,3-difluoropiperidin-1-yl)-2-methylpyrimidin-4-yl)pyrrolidin-3-yl)piperidin-2-one trifluoroacetate | 2 | H | CH | 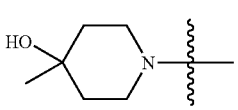 | CH₃ | 277 (4) |
| 35 | 1-{(3S,4S)-4-Amino-1-[4-(4-hydroxy-4-methyl-piperidin-1-yl)-[1,3,5]triazin-2-yl]-pyrrolidin-3-yl}-piperidin-2-one trifluoroacetate MS(M+1) 376.2 | 2 | H | N | 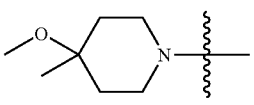 | H | 558 (4) |
| 36 | 1-((3S,4S)-4-Amino-1-(4-(4-methoxy-4-methylpiperidin-1-yl)-1,3,5-triazin-2-yl)pyrrolidin-3-yl)piperidin-2-one trifluoroacetate MS(M+1) 390.2 | 2 | H | N | | H | 22.2% (4) |
| 37 | 2-(1-(4-((3S,4S)-3-Amino-4-(2-oxopiperidin-1-yl)pyrrolidin-1-yl)-1,3,5-triazin-2-yl)piperidin-4-yloxy)benzonitrile trifluoroacetate MS(M+1) 463.2 | 2 | H | N | 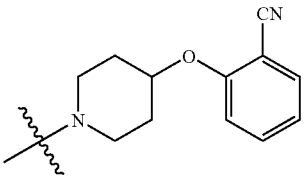 | H | 109 (4) |

-continued

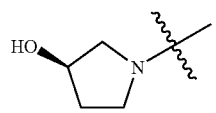

| Ex. | Compound Name and ¹H NMR (Methanol-d₄) δ | n | R¹ | Q | NR^AR^B | R⁴¹ | DPP-IV IC₅₀ (nM) or Percent Inhibition at 300 nM (n-value) |
|---|---|---|---|---|---|---|---|
| 38 | 1-((3S,4S)-4-Amino-1-(4-((R)-3-hydroxypyrrolidin-1-yl)-1,3,5-triazin-2-yl)pyrrolidin-3-yl)piperidin-2-one trifluoroacetate MS(M+1) 348.2 | 2 | H | N | 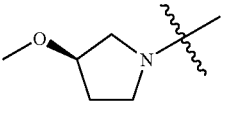 | H | 205 (4) |
| 39 | 1-((3S,4S)-4-Amino-1-(4-((R)-3-methoxypyrrolidin-1-yl)-1,3,5-triazin-2-yl)pyrrolidin-3-yl)piperidin-2-one trifluoroacetate MS(M+1) 362.2 | 2 | H | N | 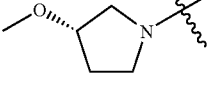 | H | 325 (4) |
| 40 | 1-((3S,4S)-4-Amino-1-(4-((S)-3-methoxypyrrolidin-1-yl)-1,3,5-triazin-2-yl)pyrrolidin-3-yl)piperidin-2-one trifluoroacetate MS(M+1) 362.1 | 2 | H | N | 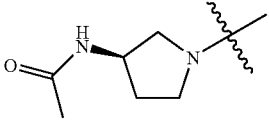 | H | 566 (4) |
| 41 | N-((S)-1-{4-[(3S,4S)-3-Amino-4-(2-oxo-piperidin-1-yl)-pyrrolidin-1-yl]-[1,3,5]triazin-2-yl}-pyrrolidin-3-yl)-acetamide trifluoroacetate HPLC Method B; RT 1.83, MS(M+1) 389.2 | 2 | H | N | 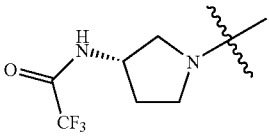 | H | 90 (4) |
| 42 | N-((R)-1-(4-((3S,4S)-3-Amino-4-(2-oxopiperidin-1-yl)pyrrolidin-1-yl)-1,3,5-triazin-2-yl)pyrrolidin-3-yl)-2,2,2-trifluoroacetamide trifluoroacetate MS(M+1) 443.1 | 2 | H | N | 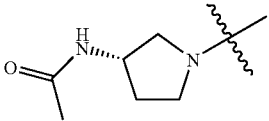 | H | 80.0 (4) |
| 43 | N-((R)-1-{4-[(3S,4S)-3-Amino-4-(2-oxo-piperidin-1-yl)-pyrrolidin-1-yl]-[1,3,5]triazin-2-yl}-pyrrolidin-3-yl)-acetamide trifluoracetate HPLC Method B; RT 1.83, MS(M+1) 364.2 | 2 | H | N | 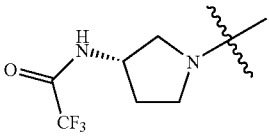 | H | 227 (4) |

-continued

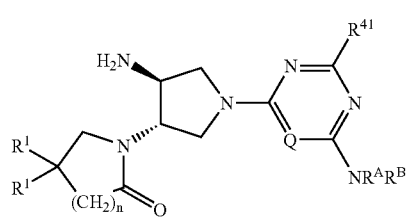

| Ex. | Compound Name and $^1$H NMR (Methanol-d$_4$) δ | n | R$^1$ | Q | NR$^A$R$^B$ | R$^{41}$ | DPP-IV IC$_{50}$ (nM) or Percent Inhibition at 300 nM (n-value) |
|---|---|---|---|---|---|---|---|
| 44 | 1-((3S,4S)-4-amino-1-(4-(3-hydroxy-3-methylpyrrolidin-1-yl)-1,3,5-triazin-2-yl)pyrrolidin-3-yl)piperidin-2-one trifluoroacetate MS(M+1) 362.2 | 2 | H | N | 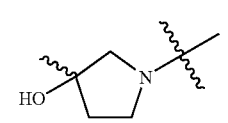 | H | 316 (4) |
| 45 | 1-{(3S,4S)-4-Amino-1-[4-(3-phenyl-pyrrolidin-1-yl)-[1,3,5]triazin-2-yl]-pyrrolidin-3-yl}-piperidin-2-one trifluoroacetate HPLC Method B; RT 2.91, MS(M+1) 408.2 | 2 | H | N | 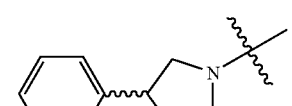 | H | 56 (4) |
| 46 | 1-((3S,4S)-4-amino-1-(4-(3,3,4,4-tetramethylpyrrolidin-1-yl)-1,3,5-triazin-2-yl)pyrrolidin-3-yl)piperidin-2-one | 2 | H | N | 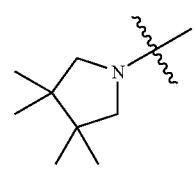 | N | 6.8% (4) |
| 47 | 1-[(3S,4S)-4-Amino-1-(4-piperidin-1-yl-[1,3,5]triazin-2-yl)-pyrrolidin-3-yl]-piperidin-2-one trifluoroacetate HPLC Method B; RT 2.53, MS(M+1) 346.2 | 2 | H | N | 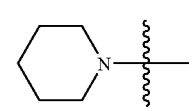 | H | 315 (4) |
| 48 | 1-((3S,4S)-4-Amino-1-(6-(3-fluoroazetidin-1-yl)pyrimidin-4-yl)pyrrolidin-3-yl)pyrrolidin-2-one dihydrochloride $^1$H NMR(D$_2$O, 400 MHz) δ 8.15(s, 1H), 5.35(m, 1H), 5.28(s, 1H), 4.76(m, 1H), 4.36(m, 2H), 4.18(m, 2H), 4.06(m, 3H), 3.40-3.80(m, 2H), 3.35(t, J=7.1Hz, 2H), 2.30(m, 2H), 1.92(m, 2H) | 1 | H | CH | 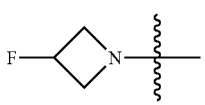 | H | 1740 (4) |

-continued

| Ex. | Compound Name and $^1$H NMR (Methanol-d$_4$) δ | n | R$^1$ | Q | NR$^A$R$^B$ | R$^{41}$ | DPP-IV IC$_{50}$ (nM) or Percent Inhibition at 300 nM (n-value) |
|---|---|---|---|---|---|---|---|
| 49 | 1-((3S,4S)-4-Amino-1-(4-(3-(3,4-difluorophenoxy)azetidin-1-yl)-1,3,5-triazin-2-yl)pyrrolidin-3-yl)piperidin-2-one trifluoroacetate MS(M+1) 446.1 | 2 | H | N | 3,4-difluorophenoxy-azetidinyl | H | 19.6% (4) |
| 50 | 1-{(3S,4S)-4-amino-1-[4-(1,3-dihydro-isoindol-2-yl)-[1,3,5]triazin-2-yl]-pyrrolidin-3-yl}-5,5-difluoro-piperidin-2-one 8.12(s, 1H), 7.38-7.22 (4H), 4.96-4.76(m, 5H), 4.14-3.96(m, 1H), 3.95-3.56(m, 3H), 3.49-3.37(m, 1H), 3.26-3.13(m, 2H), 2.77-2.58(m, 2H), 2.49-2.24(m, 2H) | 2 | F | N | isoindolinyl | H | 19.2 (4) |
| 51 | 1-{(3S,4S)-4-Amino-1-[4-(1,3-dihydro-isoindol-2-yl)-[1,3,5]triazin-2-yl]-pyrrolidin-3-yl}-piperidin-2-one trifluoroacetate HPLC Method B; RT 2.70, MS(M+1) 380.2 | 2 | H | N | isoindolinyl | H | 48.3 (4) |
| 52 | 1-((3S,4S)-4-Amino-1-(6-(isoindolin-2-yl)pyrimidin-4-yl)pyrrolidin-3-yl)pyrrolidin-2-one hydrochloride HPLC Method A; RT 1.2, MS(M+1) 365.3 | 1 | H | CH | isoindolinyl | H | 176 (4) |

-continued

| Ex. | Compound Name and $^1$H NMR (Methanol-$d_4$) δ | n | $R^1$ | Q | $NR^AR^B$ | $R^{41}$ | DPP-IV IC$_{50}$ (nM) or Percent Inhibition at 300 nM (n-value) |
|---|---|---|---|---|---|---|---|
| 53 | 1-((3S,4S)-4-amino-1-(6-(5-(trifluoromethyl)isoindolin-2-yl)pyrimidin-4-yl)pyrrolidin-3-yl)piperidin-2-one trifluoroacetate (400MHz, Methanol-d4) δ 8.34(s, 1H), 7.75(s, 1H), 7.65(q, 1H), 5.67(s, 1H), 5.27-5.09(m, 1H), 5.07-4.90(m, 4H), 4.39-4.21(m, 2H), 4.04-3.87(m, 1H), 3.81-3.72(m, 1H), 3.69-3.58(m, 1H), 3.48-3.38(m, 2H), 2.45(t, 2H), 1.97-1.75 (m, 4H). | 2 | H | CH | 5-CF$_3$-isoindolin-2-yl | H | 92.4 (4) |
| 54 | 1-((3S,4S)-4-amino-1-(6-(5,6-dichloroisoindolin-2-yl)pyrimidin-4-yl)pyrrolidin-3-yl)piperidin-2-one | 2 | H | CH | 5,6-dichloroisoindolin-2-yl | H | 32.6% (4) |
| 55 | 1-{(3S,4S)-4-Amino-1-[6-(4,7-dimethyl-1,3-dihydro-isoindol-2-yl)-pyrimidin-4-yl]-pyrrolidin-3-yl}-piperidin-2-one | 2 | H | CH | 4,7-dimethylisoindolin-2-yl | H | 101 |
| 56 | 1-{(3S,4S)-4-Amino-1-[4-(3,4-dihydro-1H-isoquinolin-2-yl)-[1,3,5]triazin-2-yl]-pyrrolidin-3-yl}-piperidin-2-one trifluoroacetate HPLC Method B; RT 2.89, MS(M+1) 394.2 | 2 | H | N | 3,4-dihydroisoquinolin-2(1H)-yl | H | 85.3 (4) |

| Ex. | Compound Name and $^1$H NMR (Methanol-$d_4$) δ | n | R$^1$ | Q | NR$^A$R$^B$ | R$^{41}$ | DPP-IV IC$_{50}$ (nM) or Percent Inhibition at 300 nM (n-value) |
|---|---|---|---|---|---|---|---|
| 57 | 1-((3S,4S)-4-Amino-1-(6-(3,4-dihydroisoquinolin-2(1H)-yl)pyrimidin-4-yl)pyrrolidin-3-yl)pyrrolidin-2-one hydrochloride MS(M+1) 379.3 | 1 | H | CH | 1,2,3,4-tetrahydroisoquinolin-2-yl | H | 317 (4) |
| 58 | 2-(4-((3S,4S)-3-Amino-4-(2-oxopiperidin-1-yl)pyrrolidin-1-yl)-1,3,5-triazin-2-yl)-N-methyl-1,2,3,4-tetrahydroisoquinoline-5-sulfonamide trifluoroacetate MS(M+1) 487.1 | 2 | H | N | 5-(N-methylsulfamoyl)-1,2,3,4-tetrahydroisoquinolin-2-yl | H | 11.6 (4) |
| 59 | 1-((3S,4S)-4-Amino-1-(4-(6,7-dimethoxy-3,4-dihydroisoquinolin-2(1H)-yl)-1,3,5-triazin-2-yl)pyrrolidin-3-yl)piperidin-2-one trifluoroacetate MS(M+1) 454.2 | 2 | H | N | 6,7-dimethoxy-3,4-dihydroisoquinolin-2(1H)-yl | H | 44.3% (4) |
| 60 | 1-((3S,4S)-4-Amino-1-(6-(3,4-dihydro-6,7-dimethoxyisoquinolin-2(1H)-yl)pyrimidin-4-yl)pyrrolidin-3-yl)pyrrolidin-2-one hydrochloride HPLC Method A; RT 1.40, MS(M+1) 439.4 | 1 | H | CH | 6,7-dimethoxy-3,4-dihydroisoquinolin-2(1H)-yl | H | 1260 (4) |

-continued

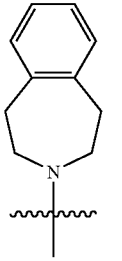

| Ex. | Compound Name and ¹H NMR (Methanol-d$_4$) δ | n | R¹ | Q | NR$^A$R$^B$ | R$^{41}$ | DPP-IV IC$_{50}$ (nM) or Percent Inhibition at 300 nM (n-value) |
|---|---|---|---|---|---|---|---|
| 61 | 1-((3S,4S)-4-Amino-1-(6-(1,2,4,5-tetrahydrobenzo[d]azepin-3-yl)pyrimidin-4-yl)pyrrolidin-3-yl)pyrrolidin-2-one hydrochloride HPLC Method A; RT 1.2, MS(M+1) 393.4 | 1 | H | CH | 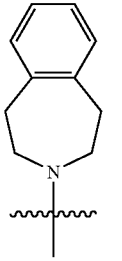 | H | 787 (4) |
| 62 | 1-((3S,4S)-4-Amino-1-(6-(6,7-dihydrothiazolo[5,4-c]pyridin-5(4H)-yl)pyrimidin-4-yl)pyrrolidin-3-yl)pyrrolidin-2-one dihydrochloride HPLC Method A; RT 1.0, MS(M+1) 386.3 | 1 | H | CH | 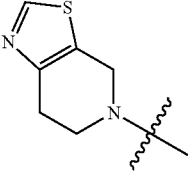 | H | 640 (4) |
| 63 | 1-((3S,4S)-4-Amino-1-(6-(5,6-dihydropyrido[3,4-d]pyrimidin-7(8H)-yl)pyrimidin-4-yl)pyrrolidin-3-yl)pyrrolidin-2-one dihydrochloride HPLC Method A; RT 1.0, MS(M+1) 381.3 | 1 | H | CH | 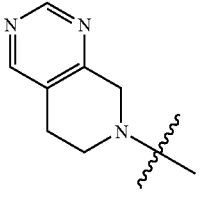 | H | 1990 (4) |
| 64 | 1-((3S,4S)-4-Amino-1-(6-(6,7-dihydro-3H-imidazo[4,5-c]pyridin-5(4H)-yl)pyrimidin-4-yl)pyrrolidin-3-yl)pyrrolidin-2-one dihydrochloride HPLC Method A; RT 0.4, MS(M+1) 369.3 | 1 | H | CH | 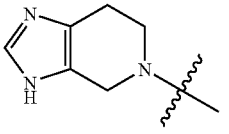 | H | 2480 (4) |
| 65 | 1-((3S,4S)-4-Amino-1-(6-(6,7-dihydrothieno[3,2-c]pyridin-5(4H)-yl)pyrimidin-4-yl)pyrrolidin-3-yl)pyrrolidin-2-one hydrochloride HPLC Method A; RT 1.2, MS(M+1) 385.3 | 1 | H | CH | 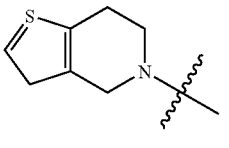 | H | 547 (4) |

-continued

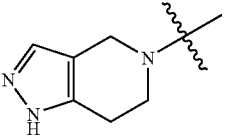

| Ex. | Compound Name and ¹H NMR (Methanol-$d_4$) δ | n | $R^1$ | Q | $NR^AR^B$ | $R^{41}$ | DPP-IV $IC_{50}$ (nM) or Percent Inhibition at 300 nM (n-value) |
|---|---|---|---|---|---|---|---|
| 66 | 1-((3S,4S)-4-Amino-1-(6-(6,7-dihydro-1H-pyrazolo[4,3-c]pyridin-5(4H)-yl)pyrimidin-4-yl)pyrrolidin-3-yl)pyrrolidin-2-one dihydrochloride MS(M+1) 369.3 | 1 | H | CH | 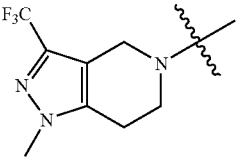 | H | 395 (4) |
| 67 | 1-((3S,4S)-4-amino-1-(4-(1-methyl-3-(trifluoromethyl)-6,7-dihydro-1H-pyrazolo[4,3-c]pyridin-5(4H)-yl)-1,3,5-triazin-2-yl)pyrrolidin-3-yl)piperidin-2-one | 2 | H | N | 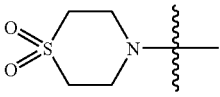 | H | 17.9% (4) |
| 68 | 1-{(3S,4S)-4-Amino-1-[4-(1,1-dioxo-6-thiomorpholin-4-yl)-[1,3,5]triazin-2-yl]-pyrrolidin-3-yl}-piperidin-2-one trifluoroacetate HPLC Method B; RT 1.96, MS(M+1) 396.2 | 2 | H | N | 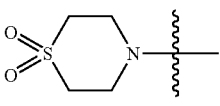 | H | 141 (4) |
| 69 | 1-((3S,4S)-4-Amino-1-[6-(1,1-dioxo-6-thiomorpholin-4-yl)-pyrimidin-4-yl]-pyrrolidin-3-yl)pyrrolidin-2-one dihydrochloride ¹H NMR(D₂O, 400 MHz) δ 8.10(s, 1H), 5.72(s, 1H), 4.78(m, 1H), 3.90-4.15(m, 6H), 3.78(s, 1H), 3.40-3.65(m, 2H), 3.20(m, 4H), 2.31(m, 2H), 1.93(m, 2H) | 1 | H | CH | 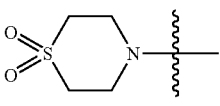 | H | 1060 (4) |
| 70 | 1-[(3S,4S)-4-Amino-1-(4-morpholin-4-yl-[1,3,5]triazin-2-yl)-pyrrolidin-3-yl]-piperidin-2-one trifluoroacetate HPLC Method B; RT 2.03, MS(M+1) 348.2 | 2 | H | N | 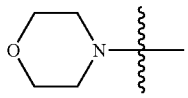 | H | 149 (4) |

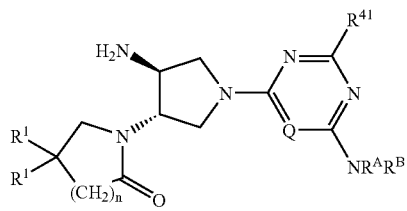

| Ex. | Compound Name and ¹H NMR (Methanol-d₄) δ | n | R¹ | Q | NRᴬRᴮ | R⁴¹ | DPP-IV IC₅₀ (nM) or Percent Inhibition at 300 nM (n-value) |
|---|---|---|---|---|---|---|---|
| 71 | 1-{(3S,4S)-4-Amino-1-[4-(6,7-dihydro-4H-thieno[3,2-c]pyridine-5-yl)-[1,3,5]triazin-2-yl]-pyrrolidin-3-yl}-piperidin-2-one trifluoroacetate HPLC Method B; RT 2.81, MS(M+1) 400.2 | 2 | H | N | (thieno[3,2-c]tetrahydropyridinyl) | H | 139 (4) |
| 72 | 1-((3S,4S)-4-Amino-1-(4-(2-ethoxy-7,8-dihydropyrido[4,3-d]pyrimidin-6(5H)-yl)-1,3,5-triazin-2-yl)pyrrolidin-3-yl)piperidin-2-one trifluoroacetate MS(M+1) 440.2 | 2 | H | N | (2-ethoxy-tetrahydropyrido[4,3-d]pyrimidinyl) | H | 13.1% (4) |
| 73 | 1-[(3S,4S)-4-Amino-1-(6-cyclopropylamino-pyrimidin-4-yl)-pyrrolidin-3-yl]-piperidin-2-one dihydrochloride ¹H NMR(D₂O, 400 MHz) δ 8.00(s, 1H), 5.52(s, 1H), 5.11(m, 1H), 4.12(m, 2H), 3.68-3.95(m, 1H), 3.40-3.60(m, 2H), 3.20(m, 2H), 2.42(m, 1H), 2.27(m, 2H), 1.55-1.72(m, 4H), 0.69(m, 2H), 0.47(m, 2H) | 2 | H | CH | cyclopropyl-HN— | H | 74.2 (4) |
| 74 | 1-((3S,4S)-4-Amino-1-(6-cyclopropylamino-pyrimidin-4-yl)pyrrolidin-3-yl)pyrrolidin-2-one trihydrochloride ¹H NMR(D₂O, 400 MHz) δ 8.05(s, 1H), 5.62(s, 1H), 4.75(m, 1H), 4.05(m, 2H), 3.43-3.65(m, 3H), 3.35(m, 2H), 2.43(m, 1H), 2.31(m, 2H), 1.92(m, 2H), 0.72(m, 2H), 0.47(m, 2H) | 1 | H | CH | cyclopropyl-HN— | H | 1400 (4) |

-continued

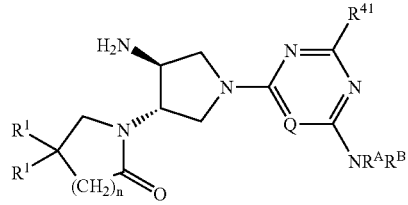

| Ex. | Compound Name and $^1$H NMR (Methanol-$d_4$) δ | n | $R^1$ | Q | $NR^AR^B$ | $R^{41}$ | DPP-IV $IC_{50}$ (nM) or Percent Inhibition at 300 nM (n-value) |
|---|---|---|---|---|---|---|---|
| 75 | 1-[(3S,4S)-4-Amino-1-(4-cyclohexylamino-[1,3,5]triazin-2-yl)-pyrrolidin-3-yl]-piperidin-2-one trifluoroacetate HPLC Method B; RT 2.59, MS(M+1) 360.3 | 2 | H | N | 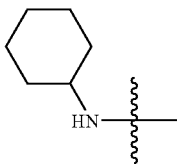 | H | 169 (4) |

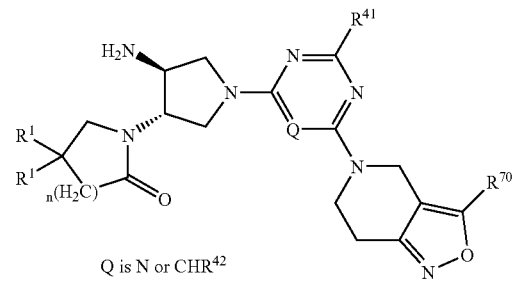

Q is N or $CHR^{42}$

| Ex. | Compound Name and $^1$H NMR(Methanol-$d_4$) δ | $R^1$ | n | Q | $R^{41}$ | $R^{42}$ | $R^{70}$ | DPP-IV Inhibition* (n-value) |
|---|---|---|---|---|---|---|---|---|
| 76 | 1-{(3S,4S)-4-Amino-1-[4-(6,7-dihydro-4H-isoxazolo[4,3-c]pyridine-5-yl)-[1,3,5]triazin-2-yl]-pyrrolidin-3-yl}-piperidin-2-one trifluoroacetate MS(M+1) 385.2 | H | 2 | N | H | H | H | 23.7 (4) |
| 77 | 1-{(3S,4S)-4-amino-1-[6-(6,7-dihydro-4H-isoxazolo[4,3-c]pyridin-5-yl)-2-trifluoromethyl-pyrimidin-4-yl]-pyrrolidin-3-yl}-5,5-difluoro-piperidin-2-one | F | 2 | CH | $CF_3$ | H | H | 33.5 (4) |
| 78 | 1-((3S,4S)-4-amino-1-(6-(6,7-dihydroisoxazolo[4,3-c]pyridin-5(4H)-yl)-2-(trifluoromethyl)pyrimidin-4-yl)pyrrolidin-3-yl)piperidin-2-one | H | 2 | CH | $CF_3$ | H | H | 39.4 (4) |
| 79 | 1-((3S,4S)-4-amino-1-(6-(6,7-dihydroisoxazolo[4,3-c]pyridin-5(4H)-yl)-5-fluoropyrimidin-4-yl)pyrrolidin-3-yl)piperidin- | H | 2 | CH | H | F | H | 61.7 (4) |

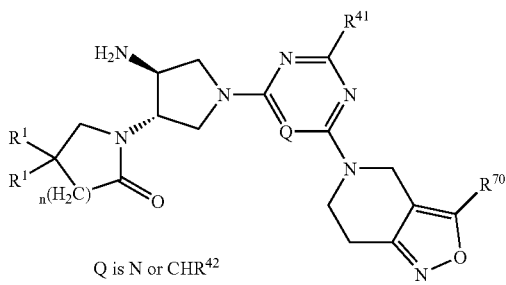

Q is N or CHR42

| Ex. | Compound Name and $^1$H NMR(Methanol-d4) δ | R1 | n | Q | R41 | R42 | R70 | DPP-IV Inhibition* (n-value) |
|---|---|---|---|---|---|---|---|---|
| | 2-one (400MHz, Methanol-d4) δ 8.38(1H, s), 8.15(1H, d), 7.49(1H, d), 7.34(1H, m), 4.92(1H, m), 4.26(1H, m), 4.1-3.98(2H, m), 3.86-3.7(2H, m), 3.42(2H, c), 3.12 (2H, q), 2.46(2H, c), 1.92(1H, c), 1.86(3H, c), 1.40(3H, t). | | | | | | | |
| 80 | 1-((3S,4S)-4-Amino-1-(6-(6,7-dihydroisoxazolo[4,3-c]pyridin-5(4H)-yl)pyrimidin-4-yl)pyrrolidin-3-yl)pyrrolidin-2-one dihydrochloride $^1$H NMR(D2O, 400MHz) δ 8.33(s, 1H), 8.10(s, 1H), 5.59(s, 1H), 4.78(m, 1H), 4.10(m, 1H), 4.05(m, 1H), 3.81(m, 3H), 3.46-3.66(m, 4H), 3.36(m, 2H), 2.83(m, 2H), 2.31(m, 2H), 1.92(m, 2H) | H | 1 | CH | H | H | H | 153 (4) |
| 81 | 1-((3S,4S)-4-amino-1-(6-(3-(trifluoromethyl)-6,7-dihydroisoxazolo[4,3-c]pyridin-5(4H)-yl)pyrimidin-4-yl)pyrrolidin-3-yl)piperidin-2-one trifluoroacetate | H | 2 | CH | H | H | CF3 | 44.5% (4) |

*IDPP-IV C50 (nM) or Percent Inhibition at 300 nM

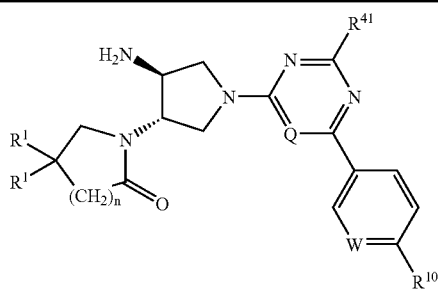

| Ex. | Compound Name and $^1$H NMR(Methanol-d4) δ | n | R1 | Q | R41 | W | R10 | DPP-IV Inhibition* (n-value) |
|---|---|---|---|---|---|---|---|---|
| 82 | 1-((3S,4S)-4-amino-1-(6-phenylpyrimidin-4-yl)pyrrolidin-3-yl)-5,5-difluoropiperidin-2-one trifluoroacetate 8.75(s, 1H), 7.94(d, 2H), 7.69-7.54(m, 3H), 7.11(s, 1H), 5.29-5.16(m, 1H, 4.46-4.06(m, 3H), 3.92-3.62(m, 4H), 2.72-2.64 (m, 2H), 2.47-2.30(m, 2H) | 2 | F | CH | H | CH | H | 28.8 (4) |
| 83 | 1-((3S,4S)-4-amino-1-(2-methyl-6-phenylpyrimidin-4-yl)pyrrolidin-3-yl)-5,5-difluoropiperidin-2-one | 2 | F | CH | CH3 | CH | H | 33.9 (4) |

-continued

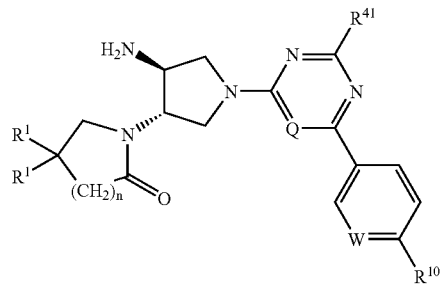

| Ex. | Compound Name and $^1$H NMR(Methanol-$d_4$) δ | n | $R^1$ | Q | $R^{41}$ | W | $R^{10}$ | DPP-IV Inhibition* (n-value) |
|---|---|---|---|---|---|---|---|---|
|  | 7.95-7.87(m, 2H), 7.52-7.44(m, 3H), 6.65 (s, 1H), 5.02-4.85(m, 1H), 4.14-3.67(m, 5H), 3.56-3.46(m, 1H), 3.32-3.21(m, 1H), 2.76-2.56(m, 2H), 2.52(s, 3H), 2.49-2.25 (m, 2H) | | | | | | | |
| 84 | 1-((3S,4S)-4-amino-1-(4-phenyl-1,3,5-triazin-2-yl)pyrrolidin-3-yl)-5,5-difluoropiperidin-2-one trifluoroacetate 8.64 (s, 1H), 8.39(d, 2H), 7.57-7.39(m, 3H), 5.21(q, 1H), 4.42-4.02(m, 3H), 3.91-3.56 (m, 4H), 2.65(t, 2H), 2.43-2.26(m, 2H) | 2 | F | N | H | CH | H | 38.7 (4) |
| 85 | 1-[(3S,4S)-4-Amino-1-(4-phenyl-[1,3,5]triazin-2-yl)-pyrrolidin-3-yl]-piperidin-2-one hydrochloride $^1$H NMR (D$_2$O, 400MHz) δ 8.56(s, 1H), 8.04-8.00(m, 2H), 7.50-7.56(m, 1H), 7.47-7.43(m, 2H), 5.15-5.07(m, 1H), 4.35(dd, J=13.3, 8.3Hz, 1H), 4.27-4.09(m, 2H), 4.00(dd, J=12.7, 8.9Hz, 1H), 3.84-3.63(m, 2H), 3.46-4.36(m, 1H), 3.26-3.23(m, 2H), 2.30-2.28(m, 2H), 1.71-1.59(m, 4H) | 2 | H | N | H | CH | H | 59.1 (4) |
| 86 | 1-{(3S,4S)-4-Amino-1-[6-(4-methoxy-phenyl)-pyrimidin-4-yl]-pyrrolidin-3-yl}-piperidin-2-one hydrochloride $^1$H NMR (D$_2$O, 400MHz) δ 8.50(s, 1H), 7.63(dd, 2H, J=8.93, 5.40Hz), 7.00(dd, 2H, J=9.14, 2.08Hz), 6.78(d, 1H, J=16.2 Hz) 5.13(m, 1H), 4.03-4.37(m, 2H), 3.60-3.96(m, 3H), 3.55(s, 3H), 3.25(m, 2H), 2.28(m, 2H), 1.60-1.75(m, 4H) | 2 | H | CH | H | CH | OCH$_3$ | 55.3 (4) |
| 87 | 1-{(3S,4S)-4-Amino-1-[6-(6-methoxy-pyridin-3-yl)-pyrimidin-4-yl]pyrrolidin-3-yl}-piperidin-2-one dihydrochloride $^1$H NMR(D$_2$O, 400MHz) δ 8.55(s, 1H), 8.42(dd, 1H, J=2.91, 2.49Hz), 8.04(dd, 1H, J=8.72, 2.49Hz), 6.98(d, 1H, J=9.14 Hz), 6.86(d, 1H, J=12.46Hz), 5.09(m, 1H), 4.00-4.40(m, 3H), 3.60-3.98(m, 5H), 3.24 (m, 2H), 2.27(m, 2H), 1.50-1.72(m, 4H) | 2 | H | CH | H | N | OCH$_3$ | 38.6 (4) |

*IDPP-IV C$_{50}$ (nM) or Percent Inhibition at 300 nM

EXAMPLES 88-95

Using appropriate starting materials, the following compounds were prepared as follows. To a solution of 0.120 mmol of the starting alcohol in dry THF (0.5 mL) was added 0.120 mmol of 60% sodium hydride as a suspension in mineral oil. The mixture was stirred for 10 minutes and then 14.9 mg (0.10 mmol) of 4,6-dichloropyrimidine was added as a solution in dry THF (0.5 mL). The mixture was warmed to 60° C. for 16 hours and evaporated. The residue was dissolved in tert-butanol (2 mL) and 14.2 mg (0.005 mmol) of tert-butyl-(3S,4S)-4-(2-oxopiperidin-1-yl)pyrrolidin-3-ylcarbamate and 12.9 mg (0.10 mmol) of DIPEA were added. The mixture was heated with agitation on an aluminum block to 120° C. for three hours and evaporated. The residue was diluted with water (1.0 mL), extracted with methylene chloride (3×1.0 mL), and the extracts evaporated. The residue was dissolved in methylene chloride (1.5 mL) and TFA (0.5 mL) was added, followed by agitation at RT for 2 hours. The mixture was concentrated and purified on a Shimadzu preparative HPLC (gradient 5:95 to 70:30 water:acetonitrile, modified with 0.1% TFA, on a Geminie 5 μp AXIA 30×50 mm C18 Phenomenex column) to provide the desired product as the free base.

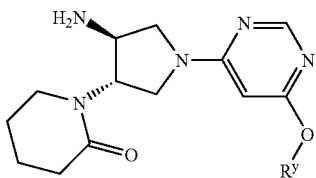

| Example | Name | R^y | DPP-IV Inhibition* (n-value) |
|---------|------|-----|------------------------------|
| 88 | 1-((3S,4S)-4-amino-1-(6-(3-fluorophenoxy)pyrimidin-4-yl)pyrrolidin-3-yl)piperidin-2-one | 3-fluorophenyl | 314 (4) |
| 89 | 1-((3S,4S)-4-Amino-1-(6-propoxypyrimidin-4-yl)pyrrolidin-3-yl)piperidin-2-one trifluoroacetate MS(M+1) 320.2 | Propyl | 318 (4) |
| 90 | 1-((3S,4S)-4-Amino-1-(6-((S)-pentan-2-yloxy)pyrimidin-4-yl)pyrrolidin-3-yl)piperidin-2-one trifluoroacetate MS(M+1) 348.3 | (S)-pentan-2-yl | 1030 (4) |
| 91 | 1-((3S,4S)-4-Amino-1-(6-(cyclopentyloxy)pyrimidin-4-yl)pyrrolidin-3-yl)piperidin-2-one trifluoroacetate MS(M+1) 346.2 | cyclopentyl | 32.2% (4) |
| 92 | 1-((3S,4S)-4-Amino-1-(6-(2,2,2-trifluoroethoxy)pyrimidin-4-yl)pyrrolidin-3-yl)piperidin-2-one trifluoroacetate MS(M+1) 360.3 | $CH_2CF_3$ | 28.9% (4) |
| 93 | 1-((3S,4S)-4-Amino-1-(6-(1,1,1-trifluoropropan-2-yloxy)pyrimidin-4-yl)pyrrolidin-3-yl)piperidin-2-one trifluoroacetate MS(M+1) 374.3 | $CH(CH_3)CF_3$ | 13.8% (4) |
| 94 | 1-((3S,4S)-4-Amino-1-(6-(2,2,3,3-tetrafluoropropoxy)pyrimidin-4-yl)pyrrolidin-3-yl)piperidin-2-one trifluoroacetate MS(M+1) 392.3 | $CH_2CF_2CHF_2$ | 23.2% (4) |
| 95 | 1-((3S,4S)-4-Amino-1-(6-(3-methylbutan-2-yloxy)pyrimidin-4-yl)pyrrolidin-3-yl)piperidin-2-one trifluoroacetate MS(M+1) 348.3 | 3-methylbutan-2-yl | 17.7% (4) |

*IDPP-IV C$_{50}$ (nM) or Percent Inhibition at 300 nM

EXAMPLE 96

4-((3S,4S)-3-amino-4-(2-oxopiperidin-1-Vl)pyrrolidin-1-yl)quinazolin-7-yl 2-(methylsulfonyl)benzenesulfonate

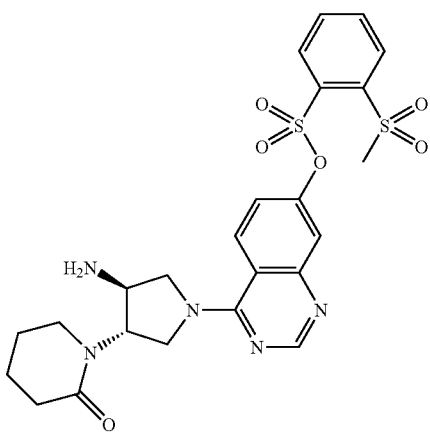

Step 1

A heterogeneous mixture of 2-amino-4-fluorobenzoic acid (8.7 g, 56 mmol) and formamidine acetate (29.2 g, 280 mmol) was stirred and heated at 165° C. for 2 h. The reaction mixture was suspended in $H_2O$ and the mixture was carefully basified with saturated sodium bicarbonate solution followed by stirring for 1 h. The brown solid was collected by filtration, washed with $H_2O$ and air dried to afford 8.42 g (91%) of 7-fluoroquinazolin-4(3H)-one. MS 165.0 (ES+).

Step 2

A solution of benzyl alcohol (5.27 g, 48.7 mmol) in N,N-dimethylformamide (12 mL) was cooled to 0° C. prior to the portion-wise addition of sodium hydride (60% dispersion in mineral oil, 1.95 g, 48.7 mmol). This mixture was warmed to room temperature and stirred for 30 min before being cooled to 0° C. followed by the addition of a solution of the product from Step 1 (2.0 g, 12 mmol) in N,N-dimethylformamide (12 mL). After the addition, the reaction was warmed to 95° C. for 16 h. After cooling to room temperature, the reaction was partitioned between EtOAc and $H_2O$. The layers were separated and the precipitated solids in the organic layer were collected by filtration, washed with EtOAc and air dried. A second crop of solids was collected and the filtrate washed with saturated sodium chloride solution, dried over sodium sulfate and concentrated to provide a third crop of solids. Combination of the solids and drying to constant weight afforded 2.82 g (93%) of 7-(benzyloxy)quinazolin-4(3H)-one as a tan solid. MS 253.3 (ES+).

Step 3

A solution of the product from Step 2 (2.82 g, 11.2 mmol) in phosphorous oxychloride (20 mL) was heated at 100° C. for 16 h. The reaction was concentrated and azeotroped once with methylene chloride. The residue was dissolved in EtOAc and washed with saturated sodium bicarbonate solution then saturated sodium chloride solution. The organic layer was dried over sodium sulfate and concentrated to provide 7-(benzyloxy)-4-chloroquinazoline (2.72 g, 90%) as a yellow solid. MS 271.2 (ES+).

Step 4

A solution of the title compound from Preparation 4 (1.57 g, 5.54 mmol), the product from Step 3 (1.50 g, 5.54 mmol) and di-isopropylethylamine (1.43 g, 11.1 mmol) in tert-butyl alcohol (5.0 mL) was heated at 145° C. for 1 h. The reaction was cooled to room temperature and partitioned between EtOAc and $H_2O$. The organic phase was separated then washed with saturated sodium bicarbonate solution then saturated sodium chloride solution. The organic layer was then dried over sodium sulfate and concentrated. The residue was separated by chromatography (Teledyne-ISCO, Combiflash Companion, 40 g RediSep column eluting with a 0-5% methanol/chloroform gradient) to afford 2.87 (99%) of tert-butyl (3S,4S)-1-(7-(benzyloxy)quinazolin-4-yl)-4-(2-oxopiperidin-1-yl)pyrrolidin-3-ylcarbamate as a yellow solid. MS 518.4 (ES+).

Step 5

To a solution of the product from Step 4 (2.87 g, 5.54 mmol) in ethanol (50 mL) was added 10% palladium supported on charcoal (0.295 g, 10 wt. %). This mixture was degassed and shaken under a hydrogen atmosphere (50 p.s.i.) at 50° C. for 16 h. The reaction was cooled to room temperature and the mixture was filtered though diatomaceous earth and the solids were washed with ethanol. The filtrate was concentrated to a brown solid. A solution of this brown solid (100 mg, 0.233 mmol) and triethylamine (94.7 g, 0.937 mmol) in methylene chloride (1.0 mL) was cooled to −78° C. prior to the drop-wise addition of 2-methylsulfonyl benzene sulfonyl chloride (119 mg, 0.467 mmol). The reaction was warmed and stirred at room temperature for 3 h and then partitioned between methylene chloride and $H_2O$. The organic layer washed with saturated sodium chloride, dried over sodium sulfate and concentrated. The residue was separated by chromatography (Teledyne-ISCO, Combiflash Companion, 12 g RediSep column eluting with a 0-5% methanol/chloroform gradient) to afford 118 mg (78%) of 4-((3S,4S)-3-(tert-butoxycarbonyl)-4-(2-oxopiperidin-1-yl)pyrrolidin-1-yl)quinazolin-7-yl 2-(methylsulfonyl)benzenesulfonate as a white solid. MS 646.5 (ES+).

Step 6

A solution of the product from Step 5 (118 mg, 0.183 mol) in methylene chloride (2.0 mL) was treated with trifluoroacetic acid (2.0 mL). After stirring at room temperature for 1 h, the reaction was concentrated and the residue was dissolved in 2N HCl and extracted with EtOAc.

The aqueous layer was separated, basified with saturated sodium bicarbonate solution and extracted with chloroform (3×). The combined organic extracts were dried over sodium sulfate and concentrated to provide 94 mg (94%) of the title compound as a white solid. (400 MHz, Methanol-$d_4$) δ 8.41 (1H, s), 8.32 (1H, d), 8.20 (2h, d), 8.15 (2H, d), 7.32 (1H, d), 7.21 (1H, m), 4.91 (1H, m), 4.23 (1H, m), 4.1-3.98 (2H, m), 3.8 (1H, m), 3.72 (1H, m), 3.4 (2H, c), 3.2 (2H, s), 2.44 (2H, c), 1.94 (1H, c), 1.85 (3H, c). DPP-IV $IC_{50}$=1.99 nM (n=8).

EXAMPLE 97

4-((3S,4S)-3-amino-4-(5,5-difluoro-2-oxopiperidin-1-yl)pyrrolidin-1-yl)$_q$ uinazolin-7-yl 2-(methylsulfonyl)benzenesulfonate

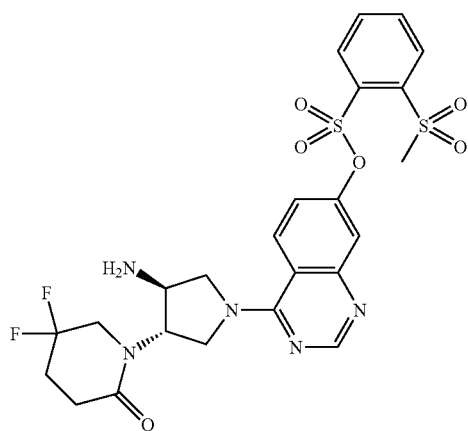

The compound 4-((3S,4S)-3-amino-4-(5,5-difluoro-2-oxopiperidin-1-yl)pyrrolidin-1-yl)quinazolin-7-yl 2-(methylsulfonyl)benzenesulfonate, shown above, was prepared as follows.

Step 1

A heterogeneous mixture of 2-amino-4-fluorobenzoic acid (8.7 g, 56 mmol) and formamidine acetate (29.2 g, 280 mmol) was stirred and heated at 165° C. for 2 hours. The reaction mixture was suspended in water and the mixture was carefully basified with saturated sodium bicarbonate solution followed by stirring for 1 hour. The brown solid was collected by filtration, washed with water and air dried to afford 8.42 g (91%) of 7-fluoroquinazolin-4(3H)-one. MS 165.0 (ES+).

Step 2

A solution of benzyl alcohol (5.27 g, 48.7 mmol) in N,N-dimethylformamide (12 mL) was cooled to 0° C. prior to the portion-wise addition of sodium hydride (60% dispersion in mineral oil, 1.95 g, 48.7 mmol). This mixture was warmed to room temperature and stirred for 30 minutes before being cooled to 0° C. followed by the addition of a solution of the product from Step 1 (2.0 g, 12 mmol) in N,N-dimethylformamide (12 mL). After the addition, the reaction was warmed to 95° C. for 16 hours. After cooling to room temperature, the reaction was partitioned between EtOAc and H$_2$O. The layers were separated and the precipitated solids in the organic layer were collected by filtration, washed with EtOAc and air dried. A second crop of solids was collected and the filtrate washed with saturated sodium chloride solution, dried over sodium sulfate and concentrated to provide a third crop of solids. Combination of the solids and drying to constant weight afforded 2.82 g (93%) of 7-(benzyloxy)quinazolin-4(3H)-one as a tan solid. MS 253.3 (ES+).

Step 3

A solution of the product from Step 2 (2.82 g, 11.2 mmol) in phosphorous oxychloride (20 mL) was heated at 100° C. for 16 hours. The reaction was concentrated and azeotroped once with dichlromethane. The residue was dissolved in EtOAc and washed with saturated sodium bicarbonate solution then saturated sodium chloride solution. The organic layer was dried over sodium sulfate and concentrated to provide 7-(benzyloxy)-4-chloroquinazoline (2.72 g, 90%) as a yellow solid. MS 271.2 (ES+).

Step 4

A solution of the title compound from Preparation 1 (177 mg, 0.554 mmol), the product from Step 3 (150 mg, 0.554 mmol) and di-isopropylethylamine (71.6 mg, 0.554 mmol) in tert-butyl alcohol (1.0 mL) was heated at 70° C. for 2 hours. The reaction was cooled to room temperature and partitioned between EtOAc and H$_2$O. The organic phase was separated then washed with saturated sodium bicarbonate solution then saturated sodium chloride solution. The organic layer was then dried over sodium sulfate and concentrated. The residue was separated by chromatography (Teledyne-ISCO, Combiflash Companion, 40 g RediSep column eluting with a 0-5% methanol/chloroform gradient) to afford 307 mg (79%) of the product as a tacky gum. MS 554.5 (ES+).

Step 5

To a solution of the product from Step 4 (242 mg, 0.437 mmol) in ethanol (10 mL) was added 10% palladium supported on charcoal (23.3 mg, 10 wt. %). This mixture was degassed and shaken under a hydrogen atmosphere (50 p.s.i.) at 50° C. for 16 hours. The reaction was cooled to room temperature and the mixture was filtered though diatomaceous earth and the solids were washed with ethanol. The filtrate was concentrated to provide a grey solid. A solution of this grey solid (100 mg, 0.22 mmol) and triethylamine (87.3 mg, 0.863 mmol) in dichloromethane (1.0 mL) was cooled to −78° C. prior to the drop-wise addition of 2-methylsulfonyl benzene sulfonyl chloride (110 mg, 0.432 mmol). The reaction was warmed to room temperature and stirred for 3 hours and then partitioned between dichloromethane and water. The organic layer washed with saturated sodium chloride, dried over sodium sulfate and concentrated. The residue was separated by chromatography (Teledyne-ISCO, Combiflash Companion, 12 g RediSep column eluting with a 0-5% methanol/chloroform gradient) to afford 106 mg (72%) of the product as a white solid. MS 682.6 (ES+).

Step 6

A solution of the product from Step 5 (106 mg, 0.155 mol) in dichlromethane (2.0 mL) was treated with trifluoroacetic acid (2.0 mL). After stirring at room temperature for 30 minutes, the reaction was concentrated and the residue was dissolved in 2N HCl and extracted with EtOAc. The aqueous layer was separated, basified with saturated sodium bicarbonate solution and extracted with chloroform (3 times). The combined organic extracts were dried over sodium sulfate and concentrated to provide 73 mg (81%) of the title compound as a white solid. (400 MHz, Methanol-d$_4$) δ 8.45 (1H, m), 8.40 (1H, s), 8.27 (1H, d), 8.15 (1H, m), 7.99 (1H, m), 7.83 (1H, m), 7.5 (1H, d), 7.34 (1H, m), 4.92 (1H, m), 4.24 (1H, c), 4.07 (1H, m), 3.95 (1H, m), 3.84-3.7 (4H, m), 3.45 (3H, s), 2.65 (2H, m), 2.38 (2H, c). DPP-IV IC$_{50}$=<1 nM (n=4).

EXAMPLES 98-144

The following examples were prepared using the method of Examples 96 and 97 with the appropriate alcohol and/or alkylating agents.

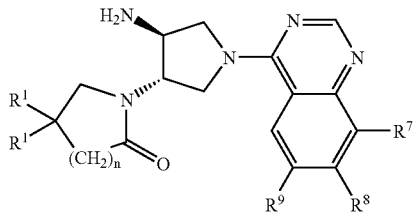

| Ex. | Compound Name and $^1$H NMR(Methanol-$d_4$) δ | R$^1$ | R$^7$ | R$^8$ | R$^9$ | DPP-IV Inhibition* (n-value) |
|---|---|---|---|---|---|---|
| 98 | 1-((3S,4S)-4-amino-1-(7-methoxyquinazolin-4-yl)pyrrolidin-3-yl)-5,5-difluoropiperidin-2-one 8.36(s, 1H), 8.17(d, 1H), 7.12-7.07 (m, 2H), 4.30-4.21(m, 1H), 4.07-3.99 (m, 1H) 3.96-3.87(m, 1H), 3.92(s, 3H), 3.85-3.64 m, 4H), 2.77-2.55(m, 2H), 2.51-2.24(m, 2H) | F | H | OCH$_3$ | H | 34.2 (4) |
| 99 | 1-((3S,4S)-4-amino-1-(7-(ethylthio)quinazolin-4-yl)pyrrolidin-3-yl)-5,5-difluoropiperidin-2-one 8.39(s, 1H), 8.13(d, 1H), 7.49(s, 1H), 7.34(dd, 1H), 4.95-4.83(m, 1H), 4.33-4.20(m, 1H), 4.05(t, 1H), 3.95 (t, 1H), 3.85-3.65(m, 4H), 3.12(q, 2H), 2.76-2.56(m, 2H), 2.54-2.23(m, 2H), 1.40 s, 3H) | F | H | SCH$_2$CH$_3$ | H | 38.4 (4) |
| 100 | 1-((3S,4S)-4-amino-1-(7-isopropoxyquinazolin-4-yl)pyrrolidin-3-yl)-5,5-difluoropiperidin-2-one 8.34(s, 1H), 8.16(d, 1H), 7.09-7.02 (m, 2H), 4.94-4.83(m, 1H), 4.77(hep, 1H), 4.29-4.20(m, 1H), 4.06-3.98(m, 1H), 3.96-3.85(m, 1H), 3.83-3.63(m, 4H), 2.75-2.59(m, 2H), 2.52-2.25(m, 2H), 1.38(dd, 6H) | F | H | OCH(CH$_3$)$_2$ | H | 44.7 (4) |
| 101 | 1-((3S,4S)-4-amino-1-(7-phenoxyquinazolin-4-yl)pyrrolidin-3-yl)-5,5-difluoropiperidin-2-one 8.35(s, 1H), 8.29(d, 1H), 7.47(t, 2H), 7.30-7.19(m, 2H), 7.15(d, 2H), 7.01 (d, 1H), 4.97-4.86(m, 1H), 4.34-4.24 (m, 1H), 4.13-4.04(m, 1H), 3.98(t, 1H), 3.86-3.69(m, 4H), 2.76-2.56(m, 2H), 2.51-2.25(m, 2H) | F | H | Phenoxy | H | 122 (4) |
| 102 | 1-[(3S,4S)-4-Amino-1-(7-chloro-quinazolin-4-yl)-pyrrolidin-3-yl]-piperidin-2-one hydrochloride $^1$H NMR(D$_2$O, 400MHz) δ 8.49(s, 1H), 8.15(d, 1H, J=9.13Hz), 7.69(d, 1H, J=2.07Hz), 7.58(dd, 1H, J=9.13, 2.07Hz), 5.13(m, 1H), 4.20-4.42(m, 3H), 3.80-4.15(m, 1H), 3.40-3.70(m, 1H), 3.28(m, 2H), 2.29(m, 2H), 1.58-1.80(m, 4H) | H | H | Cl | H | 61.4 (4) |
| 103 | 1-[(3S,4S)-4-Amino-1-(7-methoxy-quinazolin-4-yl)-pyrrolidin-3-yl]-piperidin-2-one hydrochloride $^1$H NMR(D$_2$O, 400MHz) δ 8.41(s, 1H), 8.10(d, 1H, J=9.56Hz), 7.15(dd, 1H, J=9.56, 2.50Hz), 7.00(d, 1H, J=2.5Hz), 5.14(m, 1H), 4.50(m, 1H), 4.18-4.38(m, 3H), 3.94(m, 1H), 3.81 (s, 3H), 3.28(m, 2H), 2.29(m, 2H), 1.60-1.75(m, 4H) | H | H | OCH$_3$ | H | 26.1 (4) |
| 104 | 1-[(3S,4S)-4-Amino-1-(6-chloro-quinazolin-4-yl)-pyrrolidin-3-yl]-piperidin-2-one hydrochloride HPLC Method A; RT 0.9, MS(M+1) 346.3 | H | H | H | Cl | 132 (4) |
| 105 | 1-((3S,4S)-4-Amino-1-(7-fluoroquinazolin-4-yl)pyrrolidin-3-yl)piperidin-2-one trifluoroacetate MS(M+1) 330.3 | H | H | F | H | 241 (4) |

-continued

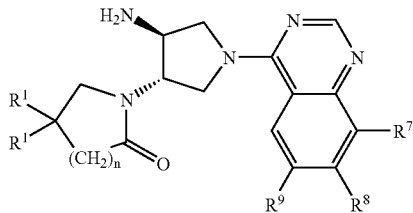

| Ex. | Compound Name and $^1$H NMR(Methanol-d$_4$) δ | R$^1$ | R$^7$ | R$^8$ | R$^9$ | DPP-IV Inhibition* (n-value) |
|---|---|---|---|---|---|---|
| 106 | 1-((3S,4S)-4-Amino-1-(6-chloro-7-methoxyquinazolin-4-yl)pyrrolidin-3-yl)piperidin-2-one trifluoroacetate MS(M+1) 376.2 | H | H | OCH$_3$ | Cl | 99.6 (4) |
| 107 | 1-((3S,4S)-4-amino-1-(6-methoxyquinazolin-4-yl)pyrrolidin-3-yl)piperidin-2-one | H | H | H | OCH$_3$ | 47% (4) |
| 108 | 1-((3S,4S)-4-Amino-1-(8-methoxyquinazolin-4-yl)pyrrolidin-3-yl)piperidin-2-one trifluoroacetate MS(M+1) 342.3 | H | OCH$_3$ | H | H | 175 (4) |
| 109 | 1-((3S,4S)-Amino-1-(8-fluoroquinazolin-4-yl)pyrrolidin-3-yl)piperidin-2-one trifluoroacetate MS(M+1) 330.3 | H | F | H | H | 110 (4) |
| 110 | 1-((3S,4S)-4-amino-1-(7-(trifluoromethyl)quinazolin-4-yl)pyrrolidin-3-yl)piperidin-2-one (400MHz, Methanol-d$_4$) δ 8.54(s, 1h), 8.48(d, 1H), 7.99(s, 1H), 7.71 (dd, 1H), 5.0-4.91(m, 1H), 4.38-4.25 (m, 1H), 4.20-3.99(m, 2H), 3.90-3.69 (m, 2H), 3.52-3.37(m, 2H), 2.58-2.37 (m, 2H), 2.0-1.78(m, 4H). | H | H | CF$_3$ | H | 47.2 (4) |
| 111 | 1-((3S,4S)-4-amino-1-(7-cyclopentylquinazolin-4-yl)pyrrolidin-3-yl)piperidin-2-one (400MHz, Methanol-d$_4$) δ 8.39(s, 1H), 8.21(d, 1H), 7.57(d, 1H), 7.42 (dd, 1H), 4.96-4.85(m, 1H), 3.43-4.22 (m, 1H), 4.12-3.94(m, 2H), 3.83-3.67 (m, 2H), 3.48-3.34(m, 2H), 3.23-3.07 (m, 1H), 2.54-2.35(m, 2H), 2.20-2.06 (m, 2H), 1.97-1.60(m, 10H). | H | H | cyclopentyl | H | 228 (4) |
| 112 | 1-((3S,4S)-4-amino-1-(quinazolin-4-yl)pyrrolidin-3-yl)piperidin-2-one trifluoroacetate 370.3; A; 1.0 | H | H | H | H | 133 (4) |
| 113 | 1-((3S,4S)-4-amino-1-(7-phenoxyquinazolin-4-yl)pyrrolidin-3-yl)piperidin-2-one (400MHz, Methanol-d$_4$) δ 8.31(s, 1H), 8.27(d, 1H), 7.48-7.38(m, 2H), 7.27-7.05(m 4H), 7.00(d, 1H), 4.96-4.84(m, 1H), 4.24(dd, 1H), 4.12-3.93 (m, 2H), 3.83-3.66(m, 2H), 3.52-3.34 (m, 2H), 2.56-2.31(m, 2H), 1.98-1.23 (m, 4H). | H | H | phenoxy | H | 72.5 (4) |
| 114 | 1-((3S,4S)-4-amino-1-(7-(benzyloxy)quinazolin-4-yl)pyrrolidin-3-yl)piperidin-2-one (400MHz, Methanol-d$_4$) δ 8.34(s, 1H), 8.20(d, 1H), 7.47(d, 2H), 7.37(t, 2H), 7.32(d, 1H), 7.18-7.11(m, 2H), 5.22(s, 2H), 4.96-4.84(m, 1H), 4.27-4.19(m, 1H), 4.11-3.93(m, 2H), 3.82-3.64(m, 2H), 3.44-3.35(m, 2H), 2.55-2.34(m, 2H), 1.96-1.74(m, 4H). | H | H | benzyloxy | H | 109 (8) |
| 115 | 1-((3S,4S)-4-amino-1-(7-isopropoxyquinazolin-4-yl)pyrrolidin-3-yl)piperidin-2-one (400MHz, Methanol-d$_4$) δ 8.33(s, 1H), 8.17(d, 1H), 7.07-7.03(m, 2H), 4.96-4.84(m, 1H), 4.76(hep, 1H), | H | H | isoproplyoxy | H | 29.7 (4) |

-continued

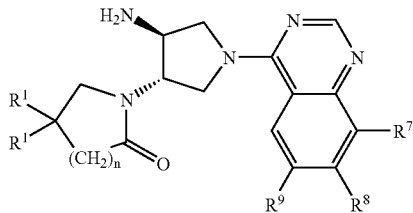

| Ex. | Compound Name and $^1$H NMR(Methanol-d$_4$) δ | R$^1$ | R$^7$ | R$^8$ | R$^9$ | DPP-IV Inhibition* (n-value) |
|---|---|---|---|---|---|---|
| | 4.29-4.18(m, 1H), 4.10-3.88(m, 2H), 3.78-3.63(m, 2H), 3.42-3.28(m, 2H), 2.55-2.32(m, 2H), 1.97-1.75(m, 4H), 1.38(dd, 6H). | | | | | |
| 116 | 1-((3S,4S)-4-amino-1-(7-isopropylquinazolin-4-yl)pyrrolidin-3-yl)piperidin-2-one (400MHz, Methanol-d$_4$) δ 8.39(s, 1H), 8.22(d, 1H), 7.55(s, 1H), 7.43 (dd, 1H), 4.97-4.88(m, 1H), 4.32-4.20 (m, 1H), 4.13-3.94(m, 2H), 3.83-3.66 (m, 2H), 3.49-3.34(m, 2H), 3.06(hep, 1H), 2.55-2.34(m, 2H), 1.98-1.75(m, 4H), 1.32(d, 6H). | H | H | isopropyl | H | 55.9 (8) |
| 117 | 1-((3S,4S)-4-amino-1-(7-(pentan-3-yl)quinazolin-4-yl)pyrrolidin-3-yl)piperidin-2-one | H | H | pentan-3-yl | H | 206 (8) |
| 118 | 3-(4-((3S,4S)-3-amino-4-(2-oxopiperidin-1-yl)pyrrolidin-1-yl)quinazolin-7-yl)propanenitrile (400MHz, Methanol-d$_4$) δ 8.42(s, 1H), 8.27(d, 1H), 7.64(d, 1H), 7.45 (dd, 1H), 4.97-4.85(m, 1H), 4.31-4.22 (m, 1H), 4.16-3.97(m, 2H), 3.84-3.69 (m, 2H), 3.46-3.40(m, 2H), 3.10(t, 2H), 2.86(t, 2H), 2.56-2.34(m, 2H), 1.97-1.75(m, 4H). | H | H | cyanoethylene | H | 85.2 (4) |
| 119 | 1-((3S,4S)-4-amino-1-(7-(cyclopentyloxy)quinazolin-4-yl)pyrrolidin-3-yl)piperidin-2-one (400MHz, Methanol-d$_4$) δ 8.35(s, 1H), 8.17(d, 1H), 7.07-7.00(m, 2H), 4.98-4.85(m, 2H), 4.27-4.19(m, 1H), 4.08-3.94(m, 2H), 3.81-3.63(m, 2H), 3.43-3.38(m, 2H), 2.55-2.38(m, 2H), 2.09-1.62(m, 12H). | H | H | cyclopentyloxy | H | 107 (4) |
| 120 | 1-((3S,4S)-4-amino-1-(7-(3-fluorophenoxy)quinazolin-4-yl)pyrrolidin-3-yl)piperidin-2-one formate (400MHz, Methanol-d$_4$) δ 8.56(1H, s), 8.40(1H, d), 7.5(1H, m), 7.36(1H, d), 7.14(1H, s), 7.16-6.96(3H, m), 5.2 (1H, m), 4.56(1H, m), 4.42-4.28(3H, c, m), 4.16(1H, m), 3.48(2H, c), 2.47 (2H, m), 1.92(2H, c), 1.86(2H, c). | H | H | ![3-fluorophenoxy] | H | 79.8 (4) |
| 121 | 6-(4-((3S,4S)-3-amino-4-(2-oxopiperidin-1-yl)pyrrolidin-1-yl)quinazolin-7-yloxy)nicotinonitrile (400MHz, Chloroform-d) d 8.54(s, 1H), 8.42(s, 1H), 8.14(d, 1H), 7.96 (dd, 1H), 7.56(d, 1H), 7.19(dd, 1H), 7.11(d, 1H), 5.04-4.91(m, 1H), 4.31-4.19(m, 2H), 4.16-4.03(m, 2H), 3.96-3.84(m, 1H), 3.75-3.60(m, 2H), 3.36-3.31(m, 2H), 2.57-2.36(m, 2H), 1.95-1.74(m, 4H). | H | H | ![pyridyloxy-CN] | H | 183 (4) |
| 122 | 1-((3S,4S)-4-amino-1-(7-(2,2,2-trifluoroethoxy)quinazolin-4-yl)pyrrolidin-3-yl)piperidin-2-one | H | H | —OCH$_2$CF$_3$ | H | 148 (4) |

-continued

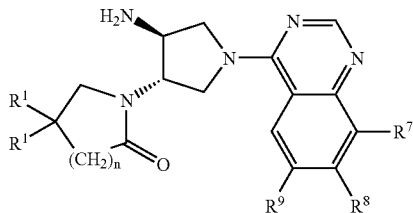

| Ex. | Compound Name and ¹H NMR(Methanol-d₄) δ | R¹ | R⁷ | R⁸ | R⁹ | DPP-IV Inhibition* (n-value) |
|---|---|---|---|---|---|---|
|  | (400MHz, Methanol-d₄) δ 8.38(s, 1H), 8.26(d, 1H), 7.22-7.14(m, 2H), 4.96-4.84(m, 1H), 4.71(q, 2H), 4.29-4.19(m, 1H), 4.10-3.94(m, 2H), 3.83-3.64(m, 2H), 3.46-3.31(m, 2H), 2.54-2.34(m, 2H), 1.98-1.74(m, 4H). |  |  |  |  |  |
| 123 | 1-((3S,4S)-4-amino-1-(7-hydroxyquinazolin-4-yl)pyrrolidin-3-yl)piperidin-2-one trifluoroacetate (400MHz Dimethyl sulfoxide-d₆) δ 8.75(s, 1H), 8.47-8.23(m, 2H), 7.17-7.10(m, 1H), 7.06(s, 1H), 5.21-5.03(m, 1H), 4.45-4.06(m, 4H), 3.95-3.68(m, 2H), 2.35-2.32(m, 2H), 1.90-1.61(m, 4H). | H | H | hydroxy | H | 113 (4) |
| 124 | 1-((3S,4S)-4-amino-1-(7-(difluoromethoxy)quinazolin-4-yl)pyrrolidin-3-yl)piperidin-2-one (400MHz, Chloroform-d) δ 8.57(s, 1H), 8.09(d, 1H), 7.46(s, 1H), 7.17-7.14(m, 1H), 6.68(t, 1H), 5.05-4.90(m, 1H), 4.27-4.20(m, 1H), 4.10(dd, 1H), 3.90(dd, 1H), 3.75-3.60(m, 2H), 3.35-3.25(m, 2H), 2.57-2.41(m, 2H), 1.97-1.70(m, 4H). | H | H | —OCHF₂ | H | 33.2 (4) |
| 125 | 1-((3S,4S)-4-amino-1-(7-cyclobutoxyquinazolin-4-yl)pyrrolidin-3-yl)piperidin-2-one (400MHz, Methanol-d₄) δ 8.33(s, 1H), 8.18(d, 1H), 7.03(dd, 1H), 6.95(d, 1H), 4.86-4.77(m, 1H), 4.76-4.54(m, 1H), 4.07-3.93(m, 3H), 3.82-3.64(m, 2H), 3.44-3.36(m, 2H), 2.59-2.35(4H), 2.25-2.10(m, 2H), 1.97-1.43(m, 6H). | H | H | cyclobutyloxy | H | 101 (4) |
| 126 | 1-((3S,4S)-4-amino-1-(7-(2-hydroxypropan-2-yl)quinazolin-4-yl)pyrrolidin-3-yl)piperidin-2-one (400MHz, Methanol-d₄) δ 8.40(s, 1H), 8.24(d, 1H), 7.83(s, 1H), 7.63(d, 1H), 5.00-4.85(m, 1H), 4.34-4.19(m, 1H), 4.14-3.94(m, 2H), 3.85-3.66(m, 2H), 3.52-3.34(m, 4H), 2.56-2.29(m, 2H), 1.98-1.72(m, 4H), 1.58(s, 6H). | H | H | —C(OH)(CH₃)₂ | H | 66.8 (4) |
| 127 | 1-((3S,4S)-4-amino-1-(7-(5-(trifluoromethyl)pyridin-2-yloxy)quinazolin-4-yl)pyrrolidin-3-yl)piperidin-2-one (400MHz Chloroform-d) d 8.57(s, 1H), 8.44(s, 1H), 8.15(d, 1H), 7.96(dd, 1H), 7.57(d, 1H), 7.22(dd, 1H), 7.13(d, 1H), 5.09-4.96(m, 1H), 4.34-4.29(m, 1H), 4.14-4.08(m, 1H), 3.96-3.87(m, 1H), 3.77-3.63(m, 2H), 3.37-3.56(m, 2H), 2.60-2.43(m, 2H), 1.97-1.76(m, 4H). | H | H | 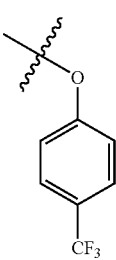 | H | 137 (4) |

-continued

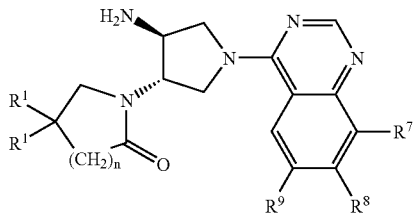

| Ex. | Compound Name and ¹H NMR(Methanol-d₄) δ | R¹ | R⁷ | R⁸ | R⁹ | DPP-IV Inhibition* (n-value) |
|---|---|---|---|---|---|---|
| 128 | 1-((3S,4S)-4-amino-1-(7-(4-fluorophenoxy)quinazolin-4-yl)pyrrolidin-3-yl)piperidin-2-one (400MHz, Methanol-d₄) δ 8.34(1H, s), 8.3(1H, d), 7.9(1H, s), 7.2(4H, m), 6.98(1H, d), 4.92(1H, m), 4.28 (1H, c), 4.14-3.99(2H, m), 3.86-3.68 (2H, m), 3.4(2H, c), 2.44(2H, c), 1.94 (1H, c), 1.85(3H, c). | H | H | 4-fluorophenoxy | H | 222 (4) |
| 129 | 1-((3S,4S)-4-amino-1-(7-(4-methoxyphenoxy)quinazolin-4-yl)pyrrolidin-3-yl)piperidin-2-one (400MHz, Methanol-d₄) δ 8.31(1H, s), 8.26(1H, d), 7.18(1H, m), 7.08 (2H, m), 7.01(2H, m), 6.93(1H, d), 4.92(1H, m), 4.25(1H, m), 4.04(2H, m), 3.82(3H, s), 3.75(2H, m), 3.42 (2H, c), 2.45(2H, c), 1.92(1H, c), 1.84(3H, c). | H | H | 4-hydroxyphenoxy | H | 61.5 (4) |
| 130 | 1-((3S,4S)-4-amino-1-(7-(3-fluorophenylthio)quinazolin-4-yl)pyrrolidin-3-yl)piperidin-2-one formate (400MHz, Methanol-d₄) δ 8.43(1H, s), 8.22(1H, s), 8.20(1H, d), 7.50 (1H, m), 7.42-7.26(3H, m), 7.22(1H, m), 5.18(1H, m), 4.4(1H, m), 4.28-4.14(3H, m), 3.96(1H, m) 3.44(2H, c), 2.48(2H, c), 1.9(2H, c), 1.86(2H, c). | H | H | 3-fluorophenylthio | H | 60.5 (4) |
| 131 | 1-((3S,4S)-4-amino-1-(7-(4-(trifluoromethoxy)phenoxy)quinazolin-4-yl)pyrrolidin-3-yl)piperidin-2-one formate (400MHz, Methanol-d₄) δ 8.46(1H, s), 8.21(1H, d), 7.7(2H, m), 7.43(2H, m), 7.36(2H, m), 5.18(1H, m), 4.44 (1H, m), 4.28(3H, m), 3.99(1H, m), 3.45(2H, c), 2.46(2H, c), 1.92(2H, c), 1.84(2H, c). | H | H | 4-(trifluoromethoxy)phenylthio | H | 189 (4) |
| 132 | 1-((3S,4S)-4-amino-1-(7-(2-(methylthio)phenylthio)quinazolin-4-yl)pyrrolidin-3-yl)piperidin-2-one | H | H | 4-(methylthio)phenylthio | H | 720 (4) |

-continued

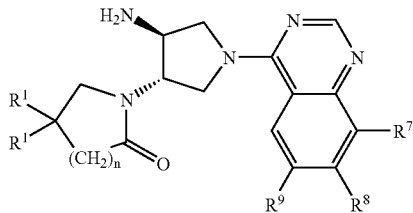

| Ex. | Compound Name and $^1$H NMR(Methanol-$d_4$) δ | $R^1$ | $R^7$ | $R^8$ | $R^9$ | DPP-IV Inhibition* (n-value) |
|---|---|---|---|---|---|---|
| 133 | 1-((3S,4S)-4-amino-1-(7-(4-(trifluoromethoxy)phenoxy)quinazolin-4-yl)pyrrolidin-3-yl)piperidin-2-one (400MHz, Methanol-$d_4$) δ 8.52(1H, s), 8.38(1H, d), 7.43(2H, d), 7.34 (1H, m), 7.29(2H, m), 7.09(1H, d), 5.19(1H, m), 4.52(1H, m), 4.38-4.28 (3H, m), 4.04(1H, m), 3.48(2H, c), 2.47(2H, c), 1.92(2H, c), 1.86(2H, c). | H | H | ![](structure with O-phenyl-OCF$_3$) | H | 200 (4) |
| 134 | 4-((3S,4S)-3-amino-4-(2-oxopiperidin-1-yl)pyrrolidin-1-yl)quinazolin-7-yl ethanesulfonate (400MHz, Methanol-$d_4$) δ 8.46(1H, s), 8.38(1H, d), 7.62(1H, d), 7.43 (1H, m), 4.93(1H, m), 4.29(1H, m), 4.15-4.0(2H, m), 3.83-3.7(2H, m), 3.49(2H, q), 3.43(2H, c), 2.46(2H, c), 1.94(1H, c), 1.86(3H, c), 1.51 (3H, t) | H | H | O—SO$_2$-ethyl | H | 218 (4) |
| 135 | 4-((3S,4S)-3-amino-4-(2-oxopiperidin-1-yl)pyrrolidin-1-yl)quinazolin-7-yl methanesulfonate (400MHz, Methanol-$d_4$) δ 8.46(1H, s), 8.39(1H, d), 7.64(1H, d), 7.44 (1H, m), 4.91(1H, m), 4.29(1H, m), 4.14-3.98(2H, m), 3.77(2H, m), 3.42 (2H, c), 3.34(3H, s), 2.46(2H, c), 1.94(1H, c), 1.86(3H, c) | H | H | O—SO$_2$-methyl | H | 128 (4) |
| 136 | 4-((3S,4S)-3-amino-4-(2-oxopiperidin-1-yl)pyrrolidin-1-yl)quinazolin-7-yl propane-2-sulfonate (400MHz, Methanol-$d_4$) δ 8.45(1H, s), 8.38(1H, d), 7.61(1H, d), 7.42 (1H, m), 4.93(1H, m), 4.29(1H, m), 4.14-4.0(2H, m), 3.85-3.65(3H, m), 3.42(2H, c), 2.45(2H, c), 1.94(1H, c), 1.86(3H, c), 1.55(6H, d) | H | H | O—SO$_2$-isopropyl | H | 135 (4) |
| 137 | 1-((3S,4S)-4-amino-1-(7-(isopropylthio)quinazolin-4-yl)pyrrolidin-3-yl)piperidin-2-one (400MHz, Methanol-$d_4$) δ 8.39(1H, s), 8.16(1H, d), 7.55(1H, d), 7.36(1H, m), 4.91(1H, m), 4.26(1H, m), 4.12-3.98(2H, m), 3.84-3.68(3H, m), 3.41 (2H, c), 2.45(2H, c), 1.92(1H, c), 1.86(3H, c), 1.40(6H, d). | H | H | S-isopropyl | H | 116 (4) |
| 138 | 1-((3S,4S)-4-amino-1-(7-(isopropylsulfonyl)quinazolin-4-yl)pyrrolidin-3-yl)piperidin-2-one trifluoroacetate | H | H | —S(O)$_2$-isopropyl | H | 24.1% (4) |
| 139 | 1-((3S,4S)-4-amino-1-(7-(ethylsulfonyl)quinazolin-4-yl)pyrrolidin-3-yl)piperidin-2-one | H | H | —S(O)$_2$-ethyl | H | 33.5% (4) |
| 140 | 1-((3S,4S)-4-amino-1-(7-(ethylthio)quinazolin-4-yl)pyrrolidin-3-yl)piperidin-2-one (400MHz, Methanol-$d_4$) δ 8.38(s, 1H), 8.15(d, 1H), 7.49(s, 1h), 7.34(d, 1H), 4.97-4.87(m, 1H), 4.31-4.23(m, | H | H | S-ethyl | H | 55 (4) |

-continued

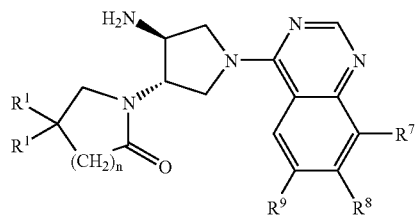

| Ex. | Compound Name and ¹H NMR(Methanol-d₄) δ | R¹ | R⁷ | R⁸ | R⁹ | DPP-IV Inhibition* (n-value) |
|---|---|---|---|---|---|---|
| | 1H), 4.13-3.96(m, 2H), 3.84-3.67(m, 2H), 3.48-3.37(m, 2H), 3.12(q, 2H), 2.56-2.36(m, 2H), 1.98-1.74(m, 4H), 1.40(t, 3H). | | | | | |
| 141 | 4-((3S,4S)-3-amino-4-(2-oxopiperidin-1-yl)pyrrolidin-1-yl)quinazolin-7-yl 4-(methylsulfonyl)benzenesulfonate | H | H | [4-(methylsulfonyl)phenylsulfonate] | H | 278 |
| 142 | 4-Fluoro-benzenesulfonic acid 4-[(3 S,4S)-3-amino-4-(2-oxo-piperidin-1-yl)-pyrrolidin-1-yl]-quinazolin-7-yl ester | H | H | [4-fluorophenylsulfonate] | H | 47/3% (4) |
| 143 | 4-((3S,4S)-3-amino-4-(2-oxopiperidin-1-yl)pyrrolidin-1-yl)quinazolin-7-yl 2,4-difluorobenzenesulfonate (400MHz, Methanol-d₄) δ 8.42(1H, s), 8.33(1H, d), 7.89(1H, m), 7.4(2H, m), 7.28(1H, m), 7.17(1H, m), 4.9 (1H, m), 4.26(1H, m), 4.12-3.98(2H, m), 3.78(1H, m), 3.72(1H, m), 3.41 (2H, c), 2.44(2H, c), 1.93(1H, c), 1.86(3H, c). | H | H | [2,4-difluorophenylsulfonate] | H | 280 (4) |
| 144 | 4-((3S,4S)-3-amino-4-(2-oxopiperidin-1-yl)pyrrolidin-1-yl)quinazolin-7-yl 3,4-difluorobenzenesulfonate | H | H | [3,4-difluorophenylsulfonate] | H | 41% (4) |

*IDPP-IV C₅₀ (nM) or Percent Inhibition at 300 nM

EXAMPLES 145-152

The following examples were prepared using the method previously described herein.

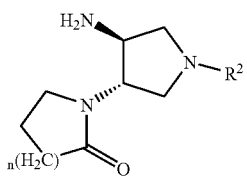

| Ex. | Compound Name and $^1$H NMR(Methanol-$d_4$) δ | n | R$^2$ | DPP-IV IC$_{50}$ (nM) (n-value) |
|---|---|---|---|---|
| 145 | 1-((3S,4S)-4-amino-1-(phthalazin-1-yl)pyrrolidin-3-yl)piperidin-2-one trifluoroacetate (400MHz, Methanol-d$_4$) δ 9.19(s, 1H), 8.72-8.68(m, 1H), 8.36-8.30(m, 1H), 8.29-8.13(m, 2H), 5.27-5.16(m, 1H), 4.60-4.28(m, 4H), 4.24-4.10(m, 1H), 3.56-3.41(m, 2H), 2.55-2.36(m, 2H), 2.03-1.76(m, 4H). | 2 | phthalazin-1-yl | 224 (4) |
| 146 | 1-((3S,4S)-4-amino-1-(6-methoxyphthalazin-1-yl)pyrrolidin-3-yl)piperidin-2-one (400MHz Chloroform-d) δ 8.88(s, 1H), 8.03(d, 1H), 7.32(dd, 1H), 7.06(d, 1H), 5.13-5.01(m, 1H), 4.18-4.10(m, 1H), 3.99(d, 2H), 3.95(s, 3H), 3.79-3.60(m, 2H), 3.41-3.26(m, 2H), 2.57-2.37(m, 2H), 2.06-1.75(m, 4H). | 2 | 6-methoxyphthalazin-1-yl | 46.2 (4) |
| 147 | 1-[(3S,4S)-4-Amino-1-(4,6-dimethoxy-[1,3,5]triazin-2-yl)-pyrrolidin-3-yl]-piperidin-2-one trifluoroacetate HPLC Method A; RT 1.1, MS(M+1) 323.3 | 2 | 4,6-dimethoxy-[1,3,5]triazin-2-yl | 133 (4) |
| 148 | 1-[(3S,4S)-4-Amino-1-(9H-purin-6-yl)-pyrrolidin-3-yl]-piperidin-2-one hydrochloride HPLC Method A; RT 0.8, MS(M+1) 302.3 | 2 | 9H-purin-6-yl | 415 (4) |
| 149 | 1-{(2S,4S)-4-Amino-1-[9-(2,2,2-trifluoro-ethyl)-9H-purin-6-yl]-pyrrolidin-3-yl}-piperidin-2-one hydrochloride HPLC Method A; RT 1.3, MS(M+1) 384.3 | 2 | 9-(2,2,2-trifluoro-ethyl)-9H-purin-6-yl | 497 (4) |

-continued

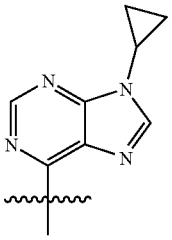

| Ex. | Compound Name and <sup>1</sup>H NMR(Methanol-d<sub>4</sub>) δ | n | R<sup>2</sup> | DPP-IV IC$_{50}$ (nM) (n-value) |
|---|---|---|---|---|
| 150 | 1-[(3S,4S)-4-Amino-1-(9-cyclopropyl-9H-purin-6-yl)-pyrrolidin-3-yl]-piperidin-2-one hydrochloride HPLC Method A; RT 1.1, MS(M+1) 342.4 | 2 | 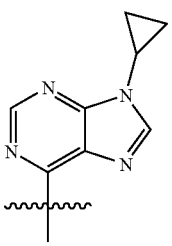 | 189 (4) |
| 151 | 1-((3S,4S)-4-Amino-1-(9-cyclopropyl-9H-purin-6-yl)pyrrolidin-3-yl)pyrrolidin-2-one hydrochloride 1H NMR(D2O, 400MHz) δ 8.29(s, 1H), 8.14(s, 1H), 4.83(m, 1H), 3.8-4.10(m, 6H), 3.20-3.60 (m, 2H), 2.35(m, 2H), 2.05(m, 2H), 1.01(m, 4H) | 1 | 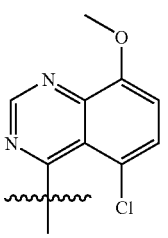 | >3000 |
| 152 | 1-((3S,4S)-4-amino-1-(5-chloro-8-methoxyquinazolin-4-yl)pyrrolidin-3-yl)piperidin-2-one trifluoroacetate | | 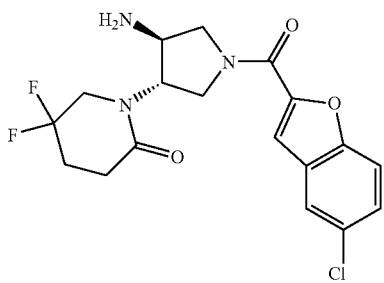 | >30000 |

EXAMPLE 153

1-((3S,4S)-4-amino-1-(5-chlorobenzofuran-2-carbonyl)pyrrolidin-3-yl)-5,5-difluoropiperidin-2-one The compound 1-((3S,4S)-4-amino-1-(6-(6-methoxypyridin-3-yl)pyrimidin-4-yl)pyrrolidin-3-yl)-5,5-difluoropiperidin-2-one trifluoroacetate, shown above, was prepared as follows.

To a solution of the product from Preparation 1 (16.0 mg, 0.05 mmol), 5-chlorobenzofuran-2-carboxylic acid (9.8 mg, 0.05 mol) and triethylamine (20.2 mg, 0.20 mmol) in ethyl acetate (3.0 mL) was added propanephosphonic acid cyclic anhydride (50% solution in ethyl acetate, 29.8 µL; 0.05 mmol). The reaction was heated to reflux for overnight, cooled to room temperature and diluted with ethyl acetate (20 mL) and water (10 mL). The organic phase was separated and washed with saturated sodium carbonate solution, dried over sodium sulfate and concentrated to provide the crude amide coupling product. This product was dissolved in a 2:1 dichloromethane and trifluoroacetic acid mixture (3.0 mL) and was stirred at room temperature for 1 hour. The reaction was concentrated and the residue was separated by HPLC (Shimadzu preparative HLPC; Gemini 5u AXIA 30×50 mm C18 Phenomenex column; 60 ml/min flow rate; 210 nm UV detector; 5% to 60% gradient eluting with acetonitrile/water modified with 0.1% trifluoroacetic acid). The collected fraction was basified with saturated sodium carbonate solution (30 mL) and extracted with dichloromethane (2×30 mL). The combined organic extracts were dried over sodium sulfate and concentrated to provide 6.4 mg (32%) of the title compound as a solid. (400 MHz, Methanol-$d_4$) d 7.74 (m, 1H), 7.57 (d, 1H), 7.47 (s, 1H), 7.46-7.40 (m, 1H), 4.89-4.79 (m, 1H), 4.44-3.49 (m, 6.5H), 3.35-3.24 (m, 0.5H), 2.74-2.53 (m, 2H), 2.48-2.23 (m, 2H). DPP-IV $IC_{50}$=78.6 nM (n=4).

EXAMPLE 154

1-[(3S,4S)-4-Amino-1-[(5-chloro-1-benzofuran-2-yl)carbonyl]-pyrrolidin-3-yl]-piperidin-2-one hydrochloride

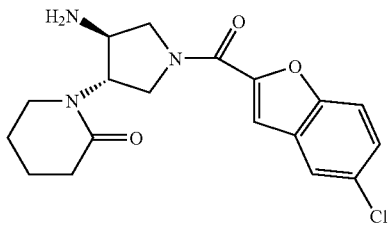

Step 1

The title compound of Preparation 4 (56.7 mg, 0.2 mmol), 5-chloro-1-benzofuran-2-carboxylic acid (39.3 mg, 0.2 mmol), and DIPEA (77.6 mg, 0.6 mmol) were dissolved in 3.0 ml of anhydrous DMF and HATU (95.1 mg, 0.25 mmol) was added. After stirring at RT overnight, the solvent was evaporated. Sodium hydroxide solution (1 N, 25 ml) was added and the residue was extracted with EtOAc. The organic layer washed with 25 ml of 4% magnesium sulfate solution, 25 ml of brine, dried over anhydrous sodium sulfate, filtered, and concentrated. The residue was purified by chromatography (Biotage 25S, 5% MeOH/EtOAc) to afford 66.8 mg (66% yield) of a white solid. MS m/z 462.3 (MH$^+$).

Step 2

The product of Step 1 (66.8 mg, 0.15 mmol) was treated with 4N HCl in dioxane (3 ml). After stirring overnight at RT, the mixture was evaporated, the residue triturated with petroleum ether, and dried under high vacuum to provide 57.3 mg (99% yield) of the title compound as a white solid. MS m/z 362.3 (MH$^+$). DPP-IV $IC_{50}$=92.3 nM (n=4)

EXAMPLE 155

1-((3S,4S)-4-amino-1-(5-methoxybenzofuran-2-carbonyl)pyrrolidin-3-yl)-5,5-difluoropiperidin-2-one

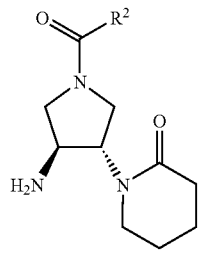

The corn pound 1-((3S,4S)-4-amino-1-(5-methoxybenzofuran-2-carbonyl)pyrrolidin-3-yl)-5,5-difluoropiperidin-2-one, shown above, was prepared using the method of Example 151 and the appropriate acid fragment. (400 MHz, Methanol-$d_4$) d 7.45 (d, 1H), 7.43 (s, 1H), 7.20-7.16 (m, 1H), 7.07-7.02 (m, 1H), 4.89-4.76 (m, 1H), 4.45-3.49 (m, 6.5H), 3.82 (s, 3H), 3.35-3.23 (m, 0.5H), 2.74-2.53 (m, 2H), 2.50-2.23 (m, 2H). DPP-IV $IC_{50}$=102 nM (n=4).

Using appropriate starting materials, the salts of Examples 156-162, disclosed in the following table below, were prepared in a manner analogous to that described in Examples 153-155.

| | | | |
|---|---|---|---|
| 156 | 1-[(3S,4S)-4-Amino-1-(benzofuran-2-carbonyl)-pyrrolidin-3-yl]-piperidin-2-one hydrochloride HPLC Method A; RT 1.9, MS(M+1) 328.4 | 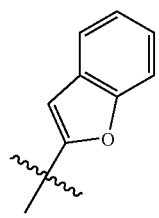 | 187 (4) |

-continued

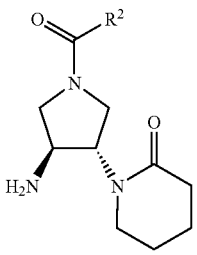

| | | | |
|---|---|---|---|
| 157 | 1-((3S,4S)-4-amino-1-(5-chlorobenzofuran-2-carbonyl)pyrrolidin-3-yl)piperidin-2-one trifluoroacetate | 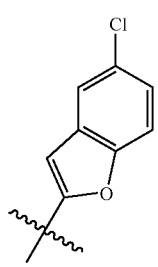 | 212 (4) |
| 158 | 1-((3S,4S)-4-amino-1-(6-chlorobenzofuran-2-carbonyl)pyrrolidin-3-yl)piperidin-2-one trifluoroacetate 362.1; A; 1.5 | 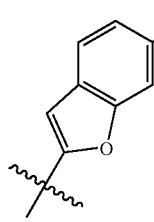 | 231 (4) |
| 159 | 1-[(3S,4S)-4-Amino-1-(5-methoxy-benzofuran-2-carbonyl)-pyrrolidin-3-yl]-piperidin-2-one hydrochloride MS(M+1) 358.5 | 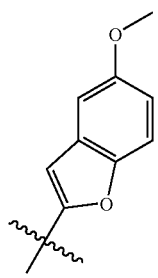 | 79.3 (4) |
| 160 | 1-[(3S,4S)-4-Amino-1-(benzo[b]thiophene-2-carbonyl)-pyrrolidin-3-yl]-piperidin-2-one hydrochloride MS(M+1) 344.4 | 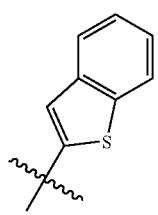 | 317 (4) |
| 161 | 1-[(3S,4S)-4-Amino-1-(5-chloro-1H-indole-2-carbonyl)-pyrrolidin-3-yl]-piperidin-2-one hydrochloride MS(M+1) 361.4 | 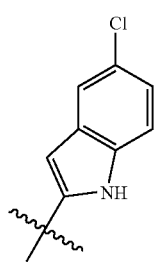 | 1160 (4) |

-continued

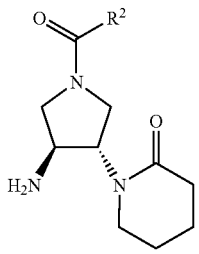

| 162 | 1-[(3S,4S)-4-Amino-1-(5-methoxy-1H-indole-2-carbonyl)-pyrrolidin-3-yl]-piperidin-2-one hydrochloride MS(M+1) 357.5 | 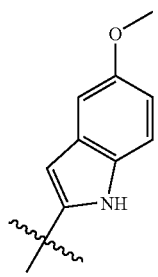 | 1460 (4) |

Biological Protocols

The utility of the compounds of formula (1), the pharmaceutically acceptable salts of the compounds, and the solvates of the compounds or salts, in the treatment of diseases (such as are detailed herein) in animals, particularly mammals (e.g., humans) may be demonstrated by the activity thereof in conventional assays known to one of ordinary skill in the relevant art, including the in vitro and in vivo assays described below. Such assays also provide a means whereby the activities of the compounds of formula (1) can be compared with the activities of other known compounds.

In Vitro Assay for Dipeptidyl Peptidase Inhibition

The dipeptidyl peptidase inhibition may be demonstrated in vitro by the following assay, which is adapted from published methods for the measurement of DPP-IV activity (Assay of dipeptidyl peptidase IV in serum by fluorimetry of 4-methoxy-2-naphthylamide. (1988) Scharpe, S., DeMeester, I., Vanhoof, G., Hendriks, D., Van Sande, M., Van Camp, K. and Yaron, A. Clin. Chem. 34:2299-2301; Dipeptidyl peptidases of human lymphocytes (1988) Lodja, Z. Czechoslovak Medicine, 11: 181-194.). 150 µL of an enzyme-substrate solution is pipetted into microtiter wells of a polystyrene 96-well plate, and maintained at 4° C. The enzyme-substrate solution comprises 50 µM Gly-Pro-4-methoxy B naphthylamide HCl in 50 mM Tris assay buffer pH 7.3 containing 0.1 M sodium chloride, 0.1% (v/v) Triton and 50 µU/mL DPP-IV (Enzyme Systems Products Cat#SPE-01, DPP-IV 5 mU/mL stock). 5 µL/well of compounds of formula (1) are added, bringing the final compound of formula (1) concentrations to 3 µM-10 nM per well.

Controls. Enzyme is omitted from four (4) wells, as a reagent blank. 5 µL of 3 mM Diprotin A is added to four wells as a positive quality control, providing a final Diprotin A concentration of 100 µM. To measure total enzyme activity (i.e. a negative control), without the influence of any compounds of formula (1), 5 µL of distilled water is added to four wells.

The entire assay is incubated overnight (about 14-18 hours) at 37° C. The reaction is quenched by adding 10 µL of Fast Blue B solution (0.5 mg/mL Fast Blue B in a buffer comprising 0.1 M sodium acetate pH 4.2 and 10% (v/v) Triton X-100 to each well, followed by shaking for approximately 5 minutes at room temperature. The plates may be analyzed on a Spectramax spectrophotometer, or equivalent equipment, (absorption maximum at 525 nm). $IC_{50}$ data for compounds may be obtained by measuring the activity of DPP-IV over a range of compound concentrations from 1 nM to 3000 nM.

The compounds of the present invention, as exemplified in Examples 1-162 exhibit inhibitory activity against DPP-IV, expressed as $IC_{50}$'s or as percent inhibition at 300 nM, against DPP-IV, which are provided in the preceding examples.

In Vivo Assay for Glucose Lowering

The glucose lowering effects of the compound of Example 2 were exemplified in 4-6 week old KK/H1J mice (Jackson Labs) in the context of an oral glucose tolerance test.

Oral glucose tolerance tests ("OGTT") have been in use in humans since, at least, the 1930s, Pincus et al., Am. J. Med. Sci, 188: 782 (1934), and are routinely used in the diagnosis of human diabetes, though not to evaluate the efficacy of therapeutic agents in patients.

KK mice have been used to evaluate glitazones (Fujita et al. Diabetes 32:804-810 (1983); Fujiwara et al., Diabetes 37: 1549-48 (1988); Izumi et al. Biopharm Durg. Dispos. 18:247-257 (1997)), metformin (Reddi et al. Diabet. Metabl. 19:44-51 (1993)), glucosidase inhibitors (Hamada et al. Jap. Pharmacol. Ther. 17:17-28 (1988); Matsuo et al. Am. J. Clin. Nutr. 55:314 S-317S (1992)), and the extra-pancreatic effects of sulfonylureas (Kameda et al Arzenim. Forsch./Drug Res. 32:39044 (1982); Muller et al. Horm. Metabl. Res. 28:469-487 (199)).

KK mice are derived from an inbred line first established by Kondo et al. (Kondo et al. Bull. Exp. Anim. 6:107-112 (1957)). The mice spontaneously develop a hereditary form of polygenic diabetes that progresses to cause renal, retinal and neurological complications analogous to those seen in human diabetic subjects, but they do not require insulin or other medication for survival. Another aspect of the invention is directed to the use of KK mice to evaluate the effects of insulin secretagogue agents in the context of an oral glucose tolerance test.

The mice were fasted overnight (about 14-18 hours), but allowed free access to water. After fasting, (time "t"=0), 25 μL of blood was drawn from the retro-orbital sinus and added to 0.025% heparinized saline (100 μL) on ice. The mice (10 per group) were then orally dosed with a solution of a compound of formula (1) in 0.5% methylcellulose (0.2 mL/mouse). Two controls groups received only 0.5% methylcellulose. At time=15 minutes, the mice were bled, as described above, and then dosed with 1 mg/kg glucose in distilled water (0.2 mL/mouse). The first control group was dosed with glucose. The second control group was dosed with water. At time=45 minutes, the mice were again bled, as described above. The blood samples were centrifuged, the plasma collected and analyzed for glucose content on a Roche-Hitachi 912 glucose analyzer. The percent (%) inhibition of glucose excursion relative to the two control groups (i.e. the glucose level in the animals receiving glucose but no test compound representing 0% inhibition and the glucose concentration in the animals receiving only water representing 100% inhibition) was found to be 39.8%.

We claim:

1. A compound having the formula

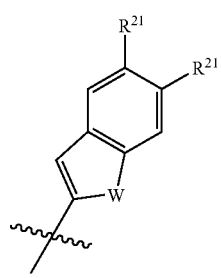

or a pharmaceutically acceptable salt thereof, wherein:
each $R^1$ is independently selected from H or F;
n is 1 or 2;
$R^2$ is

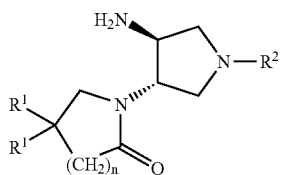

wherein W is O, N or S and $R^{21}$ is halo, —($C_1$-$C_6$)alkyl, or —($C_1$-$C_6$)alkoxy, or $R^2$ is a heteroaryl, wherein said heteroaryl is optionally substituted with one $R^3$ and is optionally substituted with one to two $R^4$;
$R^3$ is heterocycloalkyl, heteroaryl, benzyl-O—, phenyl, phenyl-O—, phenyl-S— or phenyl-S(O)$_2$O—, wherein $R^3$ is optionally, independently substituted independently with one to four hydroxy, cyano, halo, nitro, —($C_1$-$C_6$)alkyl, —($C_1$-$C_6$)haloalkyl, —($C_1$-$C_6$)haloalkoxy, —($C_1$-$C_6$)alkoxy, —NH(CO)($C_1$-$C_6$)alkyl, —S(O)$_T$($C_1$-$C_6$)alkyl, —S(O)$_2$—NR$^5$R$^6$, —NH(CO)($C_1$-$C_6$)haloalkyl, oxo or $R^7$-E-, wherein $R^7$ is phenyl or pyridinyl and E is —O— or a covalent bond and wherein said $R^7$ is optionally, independently substituted with —($C_1$-$C_3$)alkyl, halo, cyano, OH or methoxy;

T is 0 or 2;
each $R^4$ is independently cyano, halo, nitro, —($C_1$-$C_6$)alkyl, —($C_1$-$C_6$)alkyl-OH, —($C_1$-$C_6$)haloalkyl, —($C_3$-$C_6$)cycloalkyl, —($C_1$-$C_6$)alkyl-CN, —OR$^5$, —SR$^5$, —OS(O)$_2$R$^5$ or —NR$^5$R$^6$; and
$R^5$ and $R^6$ are each independently hydrogen, —($C_1$-$C_6$)alkyl, —($C_1$-$C_6$)haloalkyl, or —($C_3$-$C_6$)cycloalkyl.

2. A compound of claim 1, or a pharmaceutically acceptable salt thereof, wherein n is 2.

3. A compound of claim 2, or a pharmaceutically acceptable salt thereof, wherein $R^2$ is pyrimidinyl, quinazolinyl, triazinyl or phthalazinyl which is optionally substituted with one $R^3$ and optionally substituted with one to two $R^4$.

4. A compound of claim 3, or a pharmaceutically acceptable salt thereof, wherein $R^3$ is pyrrolidinyl, piperidinyl, pyridinyl, phenyl, dihdyroisoindolinyl, dihydroisoquinolinyl, 6,7-dihydroisoxazolo[4,3-c]pyridin-5(4H)-yl, benzyl-O—, phenyl, phenyl-O—, phenyl-S—, phenyl-S(O)$_2$O—, wherein $R^3$ is optionally substituted with one to four halo, —S(O)$_T$($C_1$-$C_6$)alkyl, —S(O)$_2$—NR$^5$R$^6$ or $R^7$-E-.

5. A compound of claim 4 having the formula

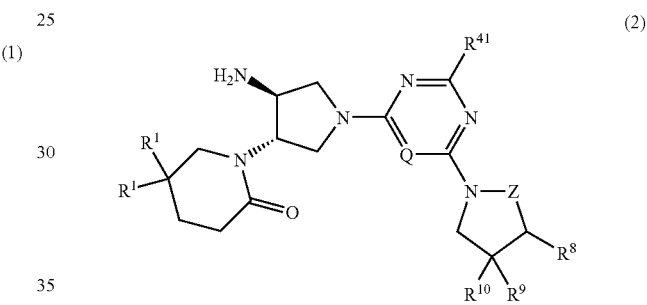

or a pharmaceutically acceptable salt thereof, wherein
$R^1$ is H or F;
Q is —N—, —CH— or —CF—;
$R^{41}$ is H or —($C_1$-$C_3$)alkyl, —($C_1$-$C_3$)haloalkyl, —S—($C_1$-$C_3$)alkyl or cyclopropyl;
Z is —CH$_2$— or —(CH$_2$)$_2$—; and
each $R^8$, $R^9$ and $R^{10}$ is independently H or F.

6. A compound of claim 5, or a pharmaceutically acceptable salt thereof, wherein Z is —CH$_2$—.

7. A compound of claim 6, or a pharmaceutically acceptable salt thereof, wherein $R^9$ and $R^{10}$ are each F.

8. A compound of claim 7, or a pharmaceutically acceptable salt thereof, wherein $R^{41}$ is H.

9. A compound of claim 8, or a pharmaceutically acceptable salt thereof, wherein each $R^1$ is F.

10. A compound of claim 9, or a pharmaceutically acceptable salt thereof, wherein Q is —N—.

11. 1-((3S,4S)-4-amino-1-(4-(3,3-difluoropyrrolidin-1-yl)-1,3,5-triazin-2-yl)pyrrolidin-3-yl)-5,5-difluoropiperidin-2-one or a pharmaceutically acceptable salt thereof.

12. A compound of claim 9, or a pharmaceutically acceptable salt thereof, wherein Q is —CH—.

13. A pharmaceutical composition comprising:
(a) a compound of claim 1, or a pharmaceutically acceptable salt thereof; and
(b) a pharmaceutically acceptable carrier, vehicle, diluent or excipient.

14. A pharmaceutical composition of claim 13, comprising
(a) a compound of claim 5, or a pharmaceutically acceptable salt thereof; and
(b) a pharmaceutically acceptable carrier, vehicle, diluent or excipient.

15. A pharmaceutical composition comprising
(a) 1-((3S,4S)-4-amino-1-(4-(3,3-difluoropyrrolidin-1-yl)-1,3,5-triazin-2-yl)pyrrolidin-3-yl)-5,5-difluoropiperidin-2-one, or a pharmaceutically acceptable salt thereof; and
(b) a pharmaceutically acceptable carrier, vehicle, diluent or excipient.

16. A method of treating Type 2 diabetes in a mammal in need of such treatment comprising administering to said mammal a therapeutically effective amount of a compound of claim 1, or a pharmaceutically acceptable salt thereof.

17. A method of claim 16 comprising administering to said mammal a therapeutically effective amount of a compound of claim 5, or a pharmaceutically acceptable salt thereof.

18. A method of treating Type 2 diabetes in a mammal in need of such treatment comprising administering to said mammal a therapeutically effective amount of 1-((3S,4S)-4-amino-1-(4-(3,3-difluoropyrrolidin-1-yl)-1,3,5-triazin-2-yl)pyrrolidin-3-yl)-5,5-difluoropiperidin-2-one, or a pharmaceutically acceptable salt thereof.

19. The method of claim 18 wherein said mammal is a human.

* * * * *